(12) United States Patent
Caufield et al.

(10) Patent No.: US 7,495,027 B2
(45) Date of Patent: Feb. 24, 2009

(54) 3-ARYL-4-HYDROXYFURANONE COMPOUNDS AND THE HUMAN AND ANIMAL HEALTH USE THEREOF

(75) Inventors: Craig Eugene Caufield, New York, NY (US); Schuyler Adam Antane, West Windsor, NJ (US); Koi Michele Morris, Plainsboro, NJ (US); Shaughnessy McGrath Naughton, Point Pleasant, PA (US); Dominick Anthony Quagliato, Bridgewater, NJ (US); Patrick Michael Andrae, Jamesburg, NJ (US); Annmarie Enos, Cranbury, NJ (US); John F. Chiarello, Newtown, PA (US)

(73) Assignee: Wyeth, Madison, NJ (US)

( * ) Notice: Subject to any disclaimer, the term of this patent is extended or adjusted under 35 U.S.C. 154(b) by 570 days.

(21) Appl. No.: 10/915,637

(22) Filed: Aug. 9, 2004
(Under 37 CFR 1.47)

(65) Prior Publication Data

US 2005/0054721 A1 Mar. 10, 2005

Related U.S. Application Data

(60) Provisional application No. 60/494,330, filed on Aug. 11, 2003.

(51) Int. Cl.
*A61K 31/341* (2006.01)
(52) U.S. Cl. .................................................. 514/474
(58) Field of Classification Search ................ 514/474; 549/313, 315
See application file for complete search history.

(56) References Cited

U.S. PATENT DOCUMENTS

| | | | |
|---|---|---|---|
| 3,676,464 A | 7/1972 | Foden et al. | |
| 3,714,173 A | 1/1973 | Sutton | |
| 3,752,829 A | 8/1973 | Sutton | |
| 3,772,341 A | 11/1973 | Sutton | |
| 3,780,065 A | 12/1973 | Sutton | |
| 3,818,048 A | 6/1974 | Foden et al. | |
| 3,944,571 A | 3/1976 | Sutton et al. | |
| 5,698,585 A | 12/1997 | Yamakoshi et al. | |

FOREIGN PATENT DOCUMENTS

| | | |
|---|---|---|
| GB | 1239266 A | 7/1971 |
| JP | 60 228471 A | 11/1985 |
| JP | 2000 086649 A | 3/2000 |
| WO | WO 99/20793 A | 4/1999 |

OTHER PUBLICATIONS

R. Ramage et al., Journal of the Chemical Society: Perkin Transactions 1, 1984, 1539-1545.
A. C. Campbell et al., Journal of the Chemical Society: Perkin Transactions 1, 1985, 1567-1576.
K. Rehse and J. Lehmke, Archiv Der Pharmazie, 1985, 318, 11-14 (English Abstract).

*Primary Examiner*—Taofiq A Solola
(74) *Attorney, Agent, or Firm*—Joel Silver; Barbara Renda; Andrea Dorigo

(57) ABSTRACT

The present invention provides a compound of formula I and the use thereof for the inhibition of bacterial cell wall biosynthesis and for the therapeutic treatment of bacterial infection or disease in a patient in need thereof. The present invention also provides the use of the formula I compound for the control of ecto- or endoparasites in homeothermic animals

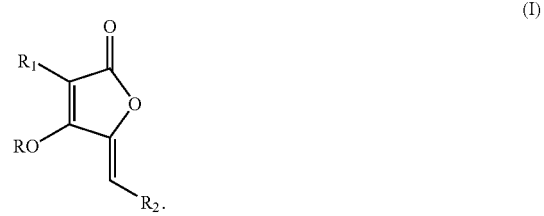

(I)

17 Claims, No Drawings

3-ARYL-4-HYDROXYFURANONE COMPOUNDS AND THE HUMAN AND ANIMAL HEALTH USE THEREOF

This application claims the benefit under 35 U.S.C. §119 (e) to co-pending U.S. provisional application No. 60/494,330, filed Aug. 11, 2003, which is hereby incorporated by reference in its entirety.

BACKGROUND OF THE INVENTION

In the human pharmaceutical arts, the rapidly developing resistance of known bacterial strains to currently prescribed pharmaceuticals has initiated a vigorous search for new classes of antibacterial agents having alternative modes of action. For example, methicillin resistant *S. aureus* (MRSA), vancomycin resistant *Enterococcus* (VRE) and penicillin resistant *S. pneumo* (PRSP) are bacterial strains which do not respond well to current clinical drug therapies.

Peptidoglycan is an essential cell wall polymer which forms a sacculus around the bacterial cell. The biosynthesis of peptidoglycan provides a unique and selective target for antibacterial activity. Peptidoglycan biosynthesis requires ten specific enzymes to perform as many synthetic transformations. These enzymes include MurA, MurB, MurC, MurD, MurE, MurF, MurG, MraY and the transglycosylase and transpeptidase families of enzymes. Inhibition of any one of these essential enzymes leads to loss of cell shape and integrity followed by bacterial death. This applies to both Gram positive and Gram negative microorganisms (Bugg, T. D. et al., Natural Products Reports 1992 199-215). Of these ten essential enzymes, β-lactam antibiotics inhibit transpeptidases, vancomycin inhibits transglycosylases and fosfomycin inhibits MurA.

In the animal health arts, virtually all commercial and most companion animals are affected by ecto-and endoparasites. The outcome associated with said parasitic infection or infestation in said animals is generally clinical disease and subclinical conditions that decrease performance. Insects, such as Phthiraptera (lice) and Diptera (flies), are among the most economically important ectoparasites in animal production. Insects, such as Siphonáptera (fleas), are highly pesteriferous to companion animals. Helminths, such as *Trichostrongylus colubriformis, Haemonchus contortus*, or the like, are among the most economically important endoparasites in animal production. Nematodes are highly pesteriferous to companion animals. Ecto- and endoparasitic infections and infestations not only seriously effect the economies of raising livestock for meat, wool, hides and milk, but are also a source of great concern for companion animals. New, economic alternative methods and compositions for the prevention, treatment and control of ecto- or endoparasites in warm-blooded animals are constantly being sought.

Therefore, it is an object of this invention to provide compounds which inhibit the Mur family of enzymes and are useful as antibacterial agents, particularly against resistant strains of bacteria.

It is another object of this invention to provide therapeutic methods and pharmaceutical compositions for the treatment of bacterial infection or disease.

It is also an object of this invention to provide an effective method for the prevention, treatment or control of ecto- or endoparasitic infection or infestation in homeothermic animals.

It is a further object of this invention to provide an ecto- or endoparasiticidal composition suitable for use on animals and humans.

It is a feature of this invention that the compounds provided herein act as effective inhibitors of bacterial cell wall biosynthesis via the Mur enzyme pathway.

Other objects and features of the invention will become more apparent by the detailed description set forth hereinbelow.

SUMMARY OF THE INVENTION

The present invention provides a compound of formula I

(I)

wherein
R is H;
R$_1$ is phenyl optionally substituted with one, two or three halogen, CN, OR$_3$, COR$_4$, SO$_2$R$_5$, NR$_6$SO$_2$R$_7$, NR$_8$COR$_9$, NR$_{10}$R$_{11}$, C$_1$-C$_6$haloalkyl or a C$_1$-C$_6$alkyl, C$_3$-C$_6$cycloalkyl, C$_2$-C$_6$alkenyl or C$_2$-C$_6$alkynyl group each optionally substituted,
  biphenyl optionally substituted with one, two or three halogen, CN, OR$_3$, COR$_4$, SO$_2$R$_5$, NR$_6$SO$_2$R$_7$, NR$_8$COR$_9$, NR$_{10}$R$_{11}$, C$_1$-C$_6$haloalkyl or a C$_1$-C$_6$alkyl, C$_3$-C$_6$cycloalkyl, C$_2$-C$_6$alkenyl or C$_2$-C$_6$alkynyl group each optionally substituted,
  naphthyl optionally substituted with one, two or three halogen, CN, OR$_3$, COR$_4$, SO$_2$R$_5$, NR$_6$SO$_2$R$_7$, NR$_8$COR$_9$, NR$_{10}$R$_{11}$, C$_1$-C$_6$haloalkyl or a C$_1$-C$_6$alkyl, C$_3$-C$_6$cycloalkyl, C$_2$-C$_6$alkenyl or C$_2$-C$_6$alkynyl group each optionally substituted, or
  heteroaryl optionally substituted with one, two or three halogen, CN, OR$_3$, COR$_4$, SO$_2$R$_5$, NR$_6$SO$_2$R$_7$, NR$_8$COR$_9$, NR$_{10}$R$_{11}$, C$_1$-C$_6$haloalkyl or a C$_1$-C$_6$alkyl, C$_3$-C$_6$cycloalkyl, C$_2$-C$_6$alkenyl or C$_2$-C$_6$alkynyl group each optionally substituted;
R$_2$ is phenyl optionally substituted with one, two or three halogen, CN, OR$_{12}$, COR$_{13}$, SO$_2$R$_{14}$, NR$_{15}$SO$_2$R$_{16}$, NR$_{17}$COR$_{18}$, NR$_{19}$R$_{20}$, C$_1$-C$_6$haloalkyl or a C$_1$-C$_6$alkyl, C$_3$-C$_6$cycloalkyl, C$_2$-C$_6$alkenyl, C$_2$-C$_6$alkynyl or heteroaryl group each optionally substituted with the proviso that only one of R$_1$ or R$_2$ may be an optionally substituted phenyl group;
  biphenyl optionally substituted with one, two or three halogen, CN, OR$_{12}$, COR$_{13}$, SO$_2$R$_{14}$, NR$_{15}$SO$_2$R$_{16}$, NR$_{17}$COR$_{18}$, NR$_{19}$R$_{20}$, C$_1$-C$_6$haloalkyl or a C$_1$-C$_6$alkyl, C$_3$-C$_6$cycloalkyl, C$_2$-C$_6$alkenyl or C$_2$-C$_6$alkynyl group each optionally substituted;
  naphthyl optionally substituted with one, two or three halogen, CN, OR$_{12}$, COR$_{13}$, SO$_2$R$_{14}$, NR$_{15}$SO$_2$R$_{16}$, NR$_{17}$COR$_{18}$, NR$_{19}$R$_{20}$, C$_1$-C$_6$haloalkyl or a C$_1$-C$_6$alkyl, C$_3$-C$_6$cycloalkyl, C$_2$-C$_6$alkenyl or C$_2$-C$_6$alkynyl group each optionally substituted;
  heteroaryl optionally substituted with one, two or three halogen, CN, OR$_{12}$, COR$_{13}$, SO$_2$R$_{14}$, NR$_{15}$SO$_2$R$_{16}$, NR$_{17}$COR$_{18}$, NR$_{19}$R$_{20}$, C$_1$-C$_6$haloalkyl or a C$_1$-C$_6$alkyl, C$_3$-C$_6$cycloalkyl, C$_2$-C$_6$alkenyl, C$_2$-C$_6$alkynyl, phenyl or heteroaryl group each optionally substituted; or $C_3$-$C_6$cycloalkyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_3$, $R_4$, $R_9$, $R_{12}$, $R_{13}$ and $R_{18}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_5$, $R_7$, $R_{14}$ and $R_{16}$ are each independently a $C_1$-$C_6$alkyl, $C_3$-$C_6$cycloalkyl, $C_2$-$C_6$alkenyl, $C_2$-$C_6$alkyl, benzyl, aryl or heteroaryl group each optionally substituted;

$R_6$, $R_8$, $R_{15}$ and $R_{17}$ are each independently H or an optionally substituted $C_1$-$C_6$alkyl group; and $R_{10}$, $R_{11}$, $R_{19}$ and $R_{20}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted or $R_{10}$ and $R_{11}$ or $R_{19}$ and $R_{20}$ may be taken together with the atom to which they are attached to form an optionally substituted 5- to 7-membered ring optionally containing one or two additional heteroatoms selected from N, O or S; or a stereoisomer thereof, a tautomer thereof or a pharmaceutically acceptable salt thereof.

The present invention also provides methods and compositions useful for the treatment of a bacterial infection or disease in a patient in need thereof.

The present invention further provides a method for the prevention, amelioration or control of ecto- or endoparasitic infection or infestation in a homeothermic animal which comprises administering to said animal a prophylactically, therapeutically or pharmaceutically effective amount of a compound of formula I

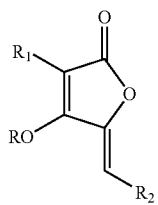

(I)

wherein

R is H, $COR_4$ or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_1$ is phenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, biphenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, naphthyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, or heteroaryl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_2$ is phenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl or heteroaryl group each optionally substituted;

biphenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

naphthyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

heteroaryl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl, phenyl or heteroaryl group each optionally substituted; or $C_3$-$C_6$cycloalkyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_3$, $R_4$, $R_9$, $R_{12}$, $R_{13}$ and $R_{18}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_5$, $R_7$, $R_{14}$ and $R_{16}$ are each independently a $C_1$-$C_6$alkyl, $C_3$-$C_6$cycloalkyl, $C_2$-$C_6$alkenyl, $C_2$-$C_6$alkyl, benzyl, aryl or heteroaryl group each optionally substituted;

$R_6$, $R_8$, $R_{15}$ and $R_{17}$ are each independently H or an optionally substituted $C_1$-$C_6$alkyl group; and $R_{10}$, $R_{11}$, $R_{19}$ and $R_{20}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted or $R_{10}$ and $R_{11}$ or $R_{19}$ and $R_{20}$ may be taken together with the atom to which they are attached to form an optionally substituted 5- to 7-membered ring optionally containing one or two additional heteroatoms selected from N, O or S; or a stereoisomer thereof, a tautomer thereof or a pharmaceutically acceptable salt thereof.

The present invention further provides an ecto- or endoparasiticidal composition which comprises a pharmaceutically acceptable carrier and an ecto- or endoparasiticidally effective amount of a compound of formula I.

DETAILED DESCRIPTION OF THE INVENTION

Many known antibiotics such as the cephalosporins, the penicillins and vancomycin inhibit the biosynthesis of peptidoglycan, an essential cell wall component of both Gram positive and Gram negative bacteria. These antibiotics inhibit membrane-bound enzymes involved in the crosslinking of the cell wall, i.e., the transpeptidation step. Earlier steps in bacterial cell wall biosynthesis have not been the target of action for current commercial antibiotics, with the exception of fosfomycin. These earlier cytoplasmic steps involve biosynthetic conversions which require the MurA through MurF enzymes. Few inhibitors of the enzymes are known to possess antibacterial activity.

Surprisingly, it has now been found that 3-aryl-4-hydroxyfuranone compounds of formula I inhibit bacteria cell wall biosynthesis via the Mur enzyme pathway. Advantageously, said hydroxyfuranone compounds are effective therapeutic agents against bacterial infection or disease, particularly against infection or disease caused by resistant strains of bacteria. Accordingly, the present invention provides 3-aryl-4-hydroxyfuranone compounds of formula I

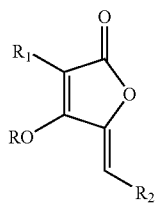

(I)

wherein

R is H;

$R_1$ is phenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, biphenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, naphthyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, or heteroaryl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_2$ is phenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl or heteroaryl group each optionally substituted with the proviso that only one of $R_1$ or $R_2$ may be an optionally substituted phenyl group;

biphenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

naphthyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

heteroaryl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl, phenyl or heteroaryl group each optionally substituted; or $C_3$-$C_6$cycloalkyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_3$, $R_4$, $R_9$, $R_{12}$, $R_{13}$ and $R_{18}$ are each independently H, $C_1$-$C_6$ haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_5$, $R_7$, $R_{14}$ and $R_{16}$ are each independently a $C_1$-$C_6$alkyl, $C_3$-$C_6$cycloalkyl, $C_2$-$C_6$alkenyl, $C_2$-$C_6$alkyl, benzyl, aryl or heteroaryl group each optionally substituted;

$R_6$, $R_8$, $R_{15}$ and $R_{17}$ are each independently H or an optionally substituted $C_1$-$C_6$alkyl group; and $R_{10}$, $R_{11}$, $R_{19}$ and $R_{20}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted or $R_{10}$ and $R_{11}$ or $R_{19}$ and $R_{20}$ may be taken together with the atom to which they are attached to form an optionally substituted 5- to 7-membered ring optionally containing one or two additional heteroatoms selected from N, O or S; or a stereoisomer thereof, a tautomer thereof or a pharmaceutically acceptable salt thereof.

As used in the specification and claims, the term halogen designates Br, Cl, I or F and the term aryl designates a carbocyclic aromatic ring system such as phenyl, naphthyl, anthracenyl or the like, preferably phenyl. The term heteroaryl, as used herein, designates a 5- to 10-membered aromatic ring system containing 1, 2 or 3 heteroatoms, which may be the same or different, selected from N, O or S. Such heteroaryl ring systems include pyrrolyl, azolyl, diazolyl, triazolyl, oxazolyl, thiazolyl, imidazolyl, furyl, thienyl, pyridyl, quinolinyl, isoquinolinyl, indolinyl, benzothienyl, benzofuranyl, benzodioxolyl, benzisoxazolyl or the like. The term haloalkyl as used herein designates $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

In the specification and claims, when the terms $C_1$-$C_6$alkyl, $C_3$-$C_{12}$cycloalkyl, fluorenyl, aryl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulfinyl, alkylsulfonyl, carbamoyl, alkylamido, phenyl, phenoxy, benzyl, benzyloxy, heteroaryl, cycloheteroalkyl or cycloalkyl groups, preferably halogen atoms, $C_1$-$C_4$ alkyl, halo($C_1$-$C_4$)alkyl or halo($C_1$-$C_4$)alkoxy groups.

Typically, 0-3 substituents, preferably 1 or 2, the same or different may be present. When any of the foregoing substituents represents or contains an alkyl substituent group, this may be linear or branched and may contain up to 12, preferably up to 6, more preferably up to 4 carbon atoms.

Pharmaceutically acceptable salts may be any salt formed by a compound of formula I and a pharmaceutically acceptable base such as organic or inorganic bases, e.g. alkali metal salts, (i.e., sodium, lithium, or potassium) alkaline earth metal salts, ammonium salts, alkylammonium salts, dialkylammonium or trialkylammonium salts or the like.

Compounds of the invention may exist as one or more stereoisomers or in enolic tautomeric forms. The various stereoisomers include enantiomers, diastereomers, atropisomers and geometric isomers. Tautomers include enols or ketones. One skilled in the art will appreciate that one stereoisomer or tautomer may be more active or may exhibit beneficial effects when enriched relative to the other stereoisomer(s) or tautomer or when separated from the other stereoisomer(s) or tautomer. Additionally, the skilled artisan knows how to separate, enrich or selectively prepare said stereoisomers or tautomers. Accordingly, the present invention comprises compounds of formula I, the stereoisomers thereof, the tautomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein $R_2$ is an optionally substituted biphenyl or naphthyl group. Another group of preferred compounds are those compounds of formula I wherein $R_1$ is phenyl substituted with one or two halogen or $C_1$-$C_6$haloalkyl groups. Further preferred compounds of the invention are those compounds of formula I wherein $R_1$ is an optionally substituted biphenyl group and $R_2$ is an optionally substituted phenyl group.

More preferred compounds of the invention are those compounds of formula I wherein $R_1$ is an optionally substituted phenyl group and $R_2$ is an optionally substituted biphenyl or naphthyl group. Another group of more preferred compounds are those compounds of formula I wherein $R_1$ is phenyl substituted with one or two halogen or $C_1$-$C_6$haloalkyl groups and $R_2$ is a biphenyl or naphthyl group optionally substituted with one or two halogen, $OR_{12}$, $COR_{13}$, $C_1$-$C_6$haloalkyl or $C_1$-$C_6$alkyl groups. Further more preferred compounds of the invention are those compounds of formula I wherein $R_1$ is a biphenyl group substituted with one or two halogen and $R_2$ is an optionally substituted phenyl group.

Among the preferred compounds of the invention are:
(5Z)-5-[(3',5'-dichloro-1,1'-biphenyl-3-yl)methylene]-3-(3,5-dichlorophenyl)-4-hydroxyfuran-2(5H)-one;
(5Z)-5-[(3',4'-dichloro-1,1'-biphenyl-2-yl)methylene]-3-(3,4-dichlorophenyl)-4-hydroxyfuran-2(5H)-one;
5-[(Z)-[1,1'biphenyl]-4-ylmethylidene]-3-(3-chlorophenyl)-4-hydroxy-2(5H)-furanone;
(5E)-5-[2'-chloro-2-methyl-1,1'-biphenyl-4-yl)methylene]-3-(3,5-dichloro-phenyl)-4-hydroxyfuran-2(5H)-one;
(5Z)-3-(3,5-dichlorophenyl)-4-hydroxy-5-{[2-methoxy-2'-(trifluoromethyl)-1,1'-biphenyl-4-yl]methylene}furan-2(5H)-one;
(5Z)-3-(3,5-dichlorophenyl)-5-[2,2'-dimethyl-1,1'-biphenyl-4-yl)methylene]-4-hydroxyfuran-2(5H)-one;
5-{[2-chloro-3-(trifluoromethyl)phenyl]methylene}-3-(3-fluoro-4-biphenyl)-4-hydroxyfuran-2(5H)-one;
3-(3-fluoro-4-biphenyl)-5-{[2-fluoro-5-(trifluoromethyl)phenyl]methylene}-4-hydroxyfuran-2(5H)-one;
(5Z)-3-(3,5-dichlorophenyl)-4-hydroxy-5-{[2-methyl-2'-(trifluoromethyl)-1,1'-biphenyl-4-yl]methylene}furan-2(5H)-one;
(5Z)-5-[3-(benzyloxy)benzylidene]-3-(3,5-dichlorophenyl)-4-hydroxyfuran-2(5H)-one;
(5Z)-5-[(2'-acetyl-2-methyl-1,1'-biphenyl-4-yl)methylene]-3-(3,5-dichloro-phenyl)-4-hydroxyfuran-2(5H)-one;
5-[(Z)-[1,1'-biphenyl]-4-ylmethylidene]-3-(3,4-dichlorophenyl)-4-hydroxy-2(5H)-furanone;
5-[Z)-[1,1'-biphenyl]-4-ylmethylidene]-3-(3,5-dichlorophenyl)-4-hydroxy-2(5H)-furanone;
3-(2-fluoro[1,1'-biphenyl]-4-yl)-4-hydroxy-5-{(Z)-[3-(trifluoromethyl)phenyl]-methylidene}furan -2(5H)-one;
5-[(Z)-[1,1'-biphenyl]-4-ylmethylidene]-3-[3,5-bis(trifluoromethyl)phenyl]-4-hydroxy-2(5H)-furanone;
(5Z)-3-(3,5-dichlorophenyl)-4-hydroxy-5-(1-naphthylmethylene)furan-2(5H)-one;
5-{[2-chloro-5-(trifluoromethyl)phenyl]methylene}-3-(3-fluoro-4-biphenyl)-4-hydroxyfuran-2(5H)-one;
5-{[2-chloro-5-(trifluoromethyl)phenyl]methylene}-3-(4'-ethoxy-4-biphenyl)-4-hydroxyfuran-2(5H)-one;
(5Z)-3-(3,5-dichlorophenyl)-4-hydroxy-5-{(4-methoxy-1-naphthyl)methylene]-furan-2(5H)-one;
(5Z)-3-(3-chlorophenyl)-4-hydroxy-5-{[2-methyl-2'-(trifluoromethyl)-1,1'-biphenyl-4-yl]methylene]furan-2 (5H)-one;
(5Z)-5-[(3'-4'-dichloro-1,1'-biphenyl-3-yl)methylene]-3-(3,4-dichlorophenyl)-4-hydroxyfuran-2(5H)-one;

a stereoisomer thereof;

a tautomer thereof; or a pharmaceutically acceptable salt thereof.

The compounds of the invention may be conveniently prepared using conventional synthetic methods and, if required, standard separation and isolation techniques. For example, compounds of formula I may be prepared by reacting a 3-bromo-4-alkoxy-furanone of formula II with an aldehyde of formula III to give the 5-hydroxyalkyl-furanone of formula IV; dehydrating the formula IV hydroxyalkylfuranone to give the corresponding 5-methylenefuranone of formula V; reacting the formula V compound with a boronic acid derivative of formula VI to give the 3-arylfuranone of formula VII; and hydrolyzing the formula VII compound to the desired 4-hydroxyfuranone of formula I.

Alternatively, the formula II compound may be reacted with tributyl tin chloride to give the compound of formula VII. The formula VII compound may then be sequentially reacted with the aldehyde of formula III and dehydrated to give the compound of formula X; and said formula X compound may be reacted with an aryl halide of formula XI to give the 4-alkoxy compound of formula VII. The formula VII compound may then be hydrolyzed as described hereinabove to give the desired compound of formula I. The reactions are shown in flow diagram I wherein R represents $C_1$-$C_6$alkyl, Hal represents Cl, Br or I and DMF designates dimethyl formamide.

similar to that described hereinabove in flow diagram I. The reaction is shown in flow diagram II wherein R is $C_1$-$C_6$alkyl.

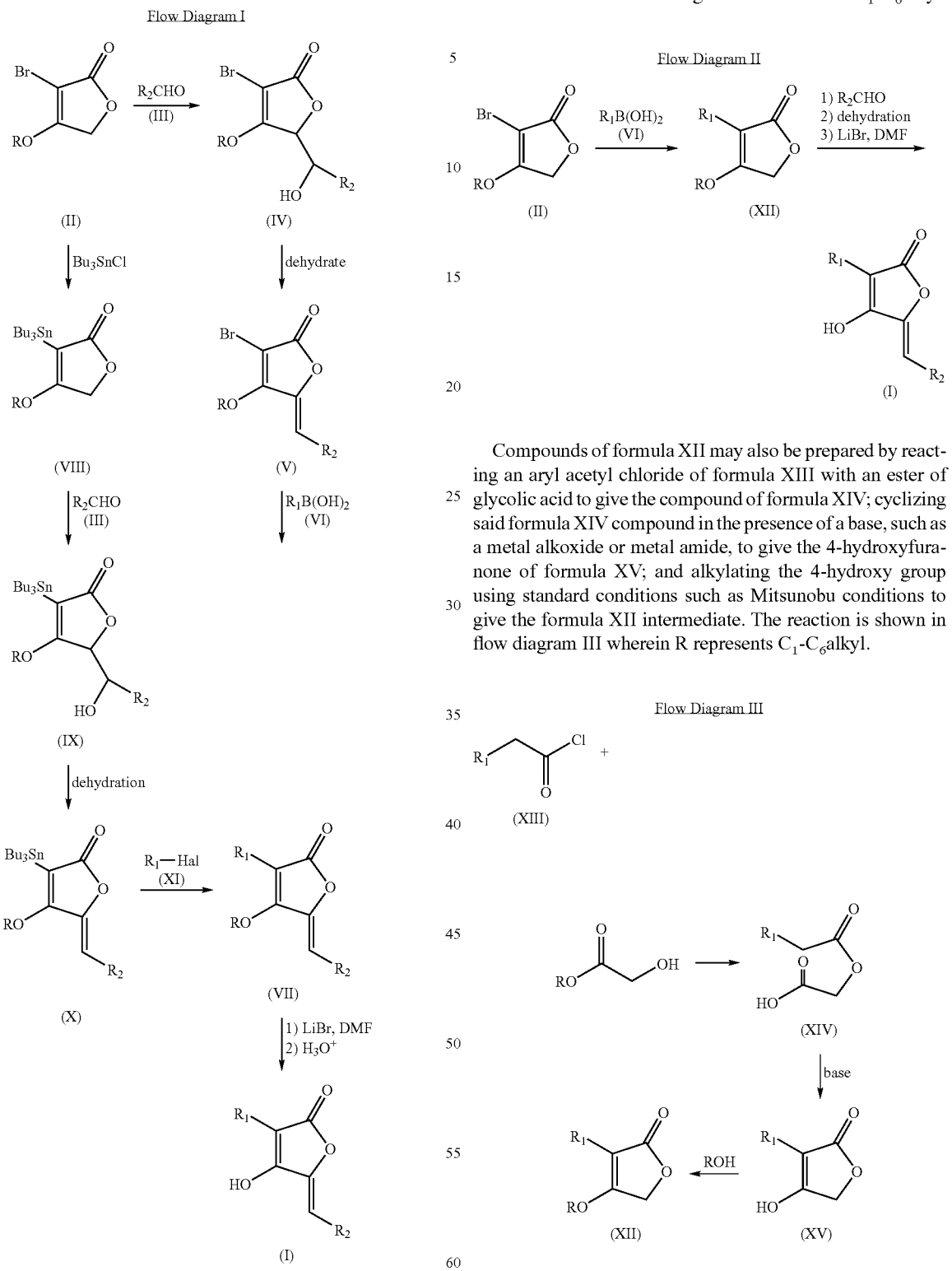

Compounds of formula XII may also be prepared by reacting an aryl acetyl chloride of formula XIII with an ester of glycolic acid to give the compound of formula XIV; cyclizing said formula XIV compound in the presence of a base, such as a metal alkoxide or metal amide, to give the 4-hydroxyfuranone of formula XV; and alkylating the 4-hydroxy group using standard conditions such as Mitsunobu conditions to give the formula XII intermediate. The reaction is shown in flow diagram III wherein R represents $C_1$-$C_6$alkyl.

Compounds of formula I may also be prepared by reacting the formula II 3-bromo-4-alkoxyfuranone with the boronic acid derivative of formula VI to give the 3-aryl-4-alkoxyfuranone of formula XII and converting said formula XII furanone to the desired compound of formula I in a manner Compounds of formula I may also be prepared by reacting a triphenylphosphine salt of formula XVI with an aldehyde in the presence of freshly prepared sodium ethoxide, as described in J. Chem Soc. Perkin Trans I, 1567, 1985. The reaction is shown in flow diagram IV wherein Ph represents phenyl.

Flow Diagram IV

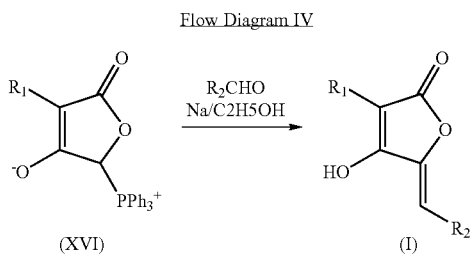

Compounds of formula I wherein R is other than H may be obtained by treatment of the 4-hydroxy compound of formula I with an amine base in the presence of an anhydride or acid chloride to give the corresponding ester or by treatment of said 4-hydroxy compound of formula I with an inorganic base such as potassium carbonate with in the presence of an alkyl, alkenyl, or benzyl halide to give the corresponding ether.

Advantageously, the formula I hydroxyfuranone compounds of the invention wherein R is H and only one of $R_1$ and $R_2$ may be an optionally substituted phenyl group are effective as antibacterial agents. Accordingly, in one embodiment of the invention, there is provided a method for the treatment of a bacterial infection or disease in a patient in need thereof which comprises providing to said patient a pharmacologically effective amount of a compound of formula I.

The term, providing, as used herein with respect to providing a compound or substance embraced by the invention, designates either directly administering such a compound or substance, or administering a prodrug, derivative or analog which forms an equivalent amount of the compound or substance within the body.

Bacterial infections include those infections caused by pathogenic bacteria such as the genera *Staphylococcus; Streptococcus; Mycobacterium; Echerichia; Bacillus; Clostridium; Pasteurella; Haemophilus; Bordetella;* or *Pseudomonas*; for example *S. aureus, E. Faecalis, E. coli, S. pneumo, Staphylococcus, Enterococcus*, or the like and resistant bacteria such as methicillin resistant *S. aureus*, vancomycin resistant *Enteroccocus*, penicillin resistant *S. pneumo*, or the like. Among the bacterial diseases which may be treated by the method of invention are: meningitis, pharyngitis, pertussis, pneumonia, bronchitis, endocarditis, cholecystus, peritonitis, enteritis, enterocolitis, gastroenteritis, urethritis, arthritis, tracheitis, bacteremia, tuberculosis, folliculitis, mastitis, dermatitis, osteomyelitis, or the like.

The antibacterial compound of formula I may be provided to a patient in need thereof by oral, parenteral, intravenous, or topical administration or in any common manner known to be an effective administration of an antibacterial agent.

The pharmacologically effective amount administered in the treatment of a specific bacterial disease may vary according to the specific disease being treated, the size, age and response pattern of the patient, the severity of the disease, the judgment of the attending physician or the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the formula I compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove wherein R is H and only one of $R_1$ or $R_2$ may be an optionally substituted phenyl group.

In this embodiment of the invention, solid carriers suitable for use in the pharmaceutical composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

Ecto- and endoparasiticidal infection and infestation are a constant problem in animal husbandry and in the care and raising of companion animals. Important agronomic and companion animals such as cattle, sheep, horses, goats, pigs, camels, water buffalo, donkeys, rabbits, fallow deer, reindeer, minks, chinchillas, racoons, chickens, geese, turkeys, ducks, dogs, cats or the like are prone to attack and infestation by biting and sucking ectoparasitic insects such as *Diptera, Muscidae* or Siphonáptera. Helminthiases is a widespread disease found in many farm and companion animals including cattle, sheep, swine, horses, poultry, fish, rabbits, goats, dogs, cats, or the like, as well as in humans. Among the helminths, which cause significant damage are trematodes such as *Faciola hepatica* or nematodes such as *Trichostrongylus colubriformis, Haemonchus contortus* and the like. Surprisingly, it has now been found that 3-aryl-4-hydroxyfuranone compounds of formula I wherein R is H, $COR_4$ or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted, may be used to control, prevent, ameliorate or effectively treat infection and infestation of ectoparasites such as *Diptera, Muscidae* or Siphonáptera, or endoparasites such as helminths, including nematodes in animals and humans. Advantageously, said hydroxyfuranone compounds may be particularly effective for controlling, preventing or treating infection or infestation of resistant strains of ecto- or endoparasites.

Accordingly, in another embodiment of the invention, there is provided a method for the prevention, amelioration or control of ecto- or endoparastic infection or infestation in a homeothermic animal which comprises administering to said animal a prophylactically, therapeutically, or pharmaceutically effective amount of a 3-aryl-4-hydroxyfuranone compound of formula I

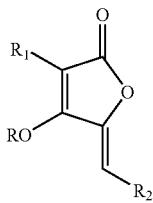

wherein

R is H, $COR_4$ or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_1$ is phenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, biphenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, naphthyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, or heteroaryl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_2$ is phenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl or heteroaryl group each optionally substituted;

biphenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

naphthyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

heteroaryl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl, phenyl or heteroaryl group each optionally substituted; or $C_3$-$C_6$cycloalkyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_3$, $R_4$, $R_9$, $R_{12}$, $R_{13}$ and $R_{18}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_5$, $R_7$, $R_{14}$ and $R_{16}$ are each independently a $C_1$-$C_6$alkyl, $C_3$-$C_6$cycloalkyl, $C_2$-$C_6$alkenyl, $C_2$-$C_6$alkyl, benzyl, aryl or heteroaryl group each optionally substituted;

$R_6$, $R_8$, $R_{15}$ and $R_{17}$ are each independently H or an optionally substituted $C_1$-$C_6$alkyl group; and $R_{10}$, $R_{11}$, $R_{19}$ and $R_{20}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted or $R_{10}$ and $R_{11}$ or $R_{19}$ and $R_{20}$ may be taken together with the atom to which they are attached to form an optionally substituted 5- to 7-membered ring optionally containing one or two additional heteroatoms selected from N, O or S; or a stereoisomer thereof, a tautomer thereof or a pharmaceutically acceptable salt thereof.

Preferred compounds of formula I useful in the animal health method of invention are those compounds of formula I wherein $R_2$ is phenyl substituted with one or two halogen, $C_1$-$C_6$haloalkyl or cyano groups. Also preferred are those compounds of formula I wherein $R_2$ is an optionally substituted biphenyl group. Another group of preferred compounds useful in the animal health method of the invention are those compounds of formula I wherein $R_1$ is phenyl substituted with one or two halogen, $C_1$-$C_6$haloalkyl or cyano groups. Further preferred compounds are those compounds of formula I wherein $R_1$ is an optionally substituted biphenyl group.

Among the preferred compounds of formula I useful in the animal health method of invention are:

5-(4-flurobenzylidene)-3-(4-chlorophenyl)-4-hydroxyfuran-2(5H)-one;

5-(4-fluorobenzylidene-3-(4-cyanophenyl)-4-hydroxyfuran-2(5H)-one;

5-(4-fluorobenzylidene-3-(4-trifluromethylphenyl)-4-hydroxyfuran-2(5H)-one;

5-(4-cyanobenzylidene)-3-(4-trifluromethylphenyl)-4-hydroxyfuran-2(5H)-one;

5-(4-trifluoromethylbenzylidene)-3-(4-trifluromethylphenyl)-4-hydroxyfuran-2(5H)-one;

5-(4-chlorobenzylidene)-3-(4-trifluromethylphenyl)-4-hydroxyfuran-2(5H)-one;

5-(4'-cyanobiphenyl-4-ylmethylene)-3-(4-trifluromethylphenyl)-4-hydroxyfuran-2(5H)-one;

5-(4-cyarobenzylidene)-3-(4-chlorophenyl)-4-hydroxyfuran-2(5H)-one;

(5Z)-(4'-cyanobiphenyl-4-ylmethylene)-3-(4-chlorophenyl)-4-hydroxyfuran-2(5H)-one;

5-(4'-chlorobiphenyl-4-ylmethylene)-3-(4-cyanophenyl)-4-hydroxyfuran-2(5H)-one;

5-(4-cyanobenzylidene)-3-(4-cyanophenyl)-4-hydroxyfuran-2(5H)-one;

5-(4-chlorbenzylidene)-3-(4-chlorophenyl)-4-hydroxyfuran-2(5H)-one;

(5E)-(4'-cyanobiphenyl-4-ylmethylene)-3-(4-cyanophenyl)-4-hydroxyfuran-2(5H)-one;

(5Z)-(2-trifluoromethylbenzylidene)-3-(4-cyanophenyl)-4-hydroxyfuran-2(5H)-one;

(5Z)-(4-chlorobenzylidene)-3-(4-chlorophenyl)-4-hydroxyfuran-2(5H)-one;

(5Z)-(1,1'-biphenyl]-4-ylmethylidene-3-[3,5-bis(trifluoromethyl)phenyl]-4-hydroxyfuran-2(5H)-one;

(5Z)-(1,1'-biphenyl]-4-ylmethylidene-3-[3,5-bis(chloro)phenyl]-4-hydroxyfuran-2(5H)-one;

(5Z)-(4'-chlorobiphenyl-4-ylmethylene)-3-(4-chlorophenyl)-4-hydroxyfuran-2(5H)-one;

(5Z)-(4'-cyanobiphenyl-4-ylmethylene)-3-(4-cyanophenyl)-4-hydroxyfuran-2(5H)-one;

Acetic acid 4-(4-chlorophenyl)-2-(4-cyanobenzylidene)-5-oxo-2,5-dihydrofuran-3-yl-ester;

2,2 Dimethylpropionic acid 4-(4-chlorophenyl)-2-(4-cyanobenzylidene)-5-oxo-2,5-dihydrofuran-3-yl-ester;

a stereoisomer thereof;

a tautomer thereof; or a pharmaceutically acceptable salt thereof.

Ectoparasitic insects which may be controlled, ameliorated or treated by the animal health method of invention include Diptera, Muscidae or Siphonáptera, in particular, Diptera: Muscidae such as Musca autumnalis (face flies), Haemtobia irritans (horn flies) Stomoxys calcitrans (stable flies), heel flies, tsetse flies, blow flies or the like. Said insects are breeders of filth and vectors of disease and are serious ectoparasitic pests of important agronomic animals such as cattle, horses and sheep. Further, Diptera: Hippoboscidae (louse flies) such as Melophagus ovinus (sheep ked), which is a serious parasite of sheep are problematic in animal production.

Among the Phthiraptera families known to be ectoparasites of animals are: Trichodectidae such as Bovicola bovis (important cattle-biting louse), B. ovis (sheep-biting louse) or B. equi (horsebiting louse); Haemopinidae such as Haematopinus suis (hog louse), or H. asini (horse sucking louse); Linognathidae such as Linognathus stenopsis (goat sucking louse) or L. vitali (long-nosed cattle louse); or the like.

One of the Siphonáptera families known to infest companion animals is Pulicidae such as Archaeopsyllniae (cat and dog fleas), Spilopsyllinae (rabbit fleas), or the like.

Endoparasitic infections which may be controlled, ameliorated or treated by the method of the invention include those Helminthiases infections caused by the class Trematoda, commonly known as flukes or flatworms or by the class Nematoda, commonly known as nematodes or roundworms. The method of the invention is particularly effective against infection caused by Trematoda, especially members of the genera Fasciola, Fascioloides, Paramphistomum, Dicrocoelium, Eurytrema, Ophisthorchis, Fascioiopsis, Echinostoma, or Paragonimus. The method of the invention is uniquely effective against trematodes and may provide significant control of the economically important Faciola hepatica, commonly known as liver fluke. Helminthiases infection is also caused by a group of worms referred to as nematodes. Nematodes cause serious damage to the walls and tissues of the organs in which they reside, including the intestinal tract, heart, lungs and blood vessels, and are a primary cause of anemia. If left untreated they may result in death to the infected host. The nematodes most commonly found to be the infecting agents of warm-blooded animals include Haemonchus, Ostertagia, Cooperia, Drofilaria, Oesphagastomum, Nematodirus and Dictyocaulus.

In addition to helmintic infection, the present method of invention is also useful for the control of endoparasitic arthropod infestations such as cattle grub. The method of invention is also effective against infection caused by nematodes such as, T. colubriformis, H. contortus, or the like.

Homeothermic animals suitable for use in the method of invention are all warm-blooded animals susceptible to ecto- or endoparasitic infection or infestation including farm animals such as cattle, sheep, swine, horses, poultry, rabbits, goats, or the like, preferably cattle, sheep, swine or horses; companion animals such as dogs, cats, gerbils, rabbits, birds or the like, preferably dogs or cats; or humans.

The effective amount of the formula I compound to be used in the animal health method of invention will vary according to the specific compound used, the mode of application used, the identity of the parasite to be controlled, the degree of infection or infestation, the extent of the parasite population, the nature of the target host, the weather conditions or the like. Effective dosages may range from 0.1 mg/kg to 100 mg/kg, preferably about 1.0 mg/kg to 50 mg/kg. Naturally, quantities of greater than effective amounts of said formula I compound may be administered, but are not required for the protection of the target animals from the ecto- or endoparasite.

Compounds of formula I may be administered to the target homeothermic animal orally, topically or parenterally, preferably orally. For example, the formula I 3-aryl-4-hydroxyfuranone compound may be administered to said animal in or with their drinking water or as a feed additive or in the form of a pill, tablet, bolus, implant, capsule or drench. The formula I compound may also be administered topically by applying said compound to the skin, hide or hair of the homeothermic animal. Parenteral administration, i.e., intramural, intramuscular or subcutaneous injection is also suitable for the inventive method.

In actual practice, the compounds of formula I are provided by administering the compound or a precursor thereof in a solid or liquid form, either neat or in combination with one or more conventional pharmaceutical carriers or excipients. Accordingly, the present invention provides an ecto- or endoparasiticidal composition which comprises a pharmaceutically acceptable carrier and an effective amount of a 3-aryl-4-hydroxyfuranone compound of formula I

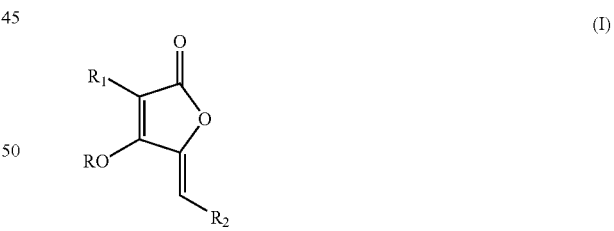

(I)

wherein

R is H, $COR_4$ or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_1$ is phenyl optionally substituted with one, two or three halogen, CN, $OR_3$, $COR_4$, $SO_2R_5$, $NR_6SO_2R_7$, $NR_8COR_9$, $NR_{10}OR_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, biphenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, naphthyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, or heteroaryl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_2$ is phenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl or heteroaryl group each optionally substituted;

biphenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

naphthyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

heteroaryl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl, phenyl or heteroaryl group each optionally substituted; or $C_3$-$C_6$cycloalkyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_3$, $R_4$, $R_9$, $R_{12}$, $R_{13}$ and $R_{18}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_5$, $R_7$, $R_{14}$ and $R_{16}$ are each independently a $C_1$-$C_6$alkyl, $C_3$-$C_6$cycloalkyl, $C_2$-$C_6$alkenyl, $C_2$-$C_6$alkyl, benzyl, aryl or heteroaryl group each optionally substituted;

$R_6$, $R_8$, $R_{15}$ and $R_{17}$ are each independently H or an optionally substituted $C_1$-$C_6$alkyl group; and $R_{10}$, $R_{11}$, $R_{19}$ and $R_{20}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted or $R_{10}$ and $R_{11}$ or $R_{19}$ and $R_{20}$ may be taken together with the atom to which they are attached to form an optionally substituted 5- to 7-membered ring optionally containing one or two additional heteroatoms selected from N, O or S; or a stereoisomer thereof, a tautomer thereof or a pharmaceutically acceptable salt thereof.

In this embodiment of the invention, solid carriers suitable for use in the ecto- or endoparasiticidal composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), dimethyl sulfoxide, alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Ecto- or endoparasiticidal compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

An ecto- or endoparasiticidal composition of the invention may be in the form of a pill, tablet, bolus, implant, capsule or drench, containing sufficient formula I compound to provide the treated animal with about 0.01 mg/kg to 100 mg/kg of animal body weight per day of the formula I compound. These dosage forms are prepared by intimately and uniformly mixing the active ingredient with suitable finely divided diluents, fillers, disintegrating agents and/or builders such as starch, lactose, talc, magnesium stearate, vegetable gums or the like. These unit dosage formulations may be varied according to the kind and size of the animal to be treated, the severity or type of infection encountered, the weight of the host animal, or the like.

For a parenteral composition, the formula I compound may be dispersed in a physiologically acceptable solvent for subcutaneous injection or it may be dispersed in a fat or wax or mixture thereof containing an oil, buffer, surfactant, stabilizer, preservative and salt. Components useful in these preparations include carbowax, aluminum monostearate gel, diethyl succinate, soya oil, glyercal dioleate, saline and capric/caprylic triglycerides.

The formula I compound may also be applied topically to the larger animals such as swine, sheep, cattle and horses and companion animals such as dogs and cats in the form of aqueous dips or sprays. For this inventive composition, the active compound is generally prepared as a wettable powder, emulsifiable concentrate, aqueous flowable or the like, which is mixed with water at the site of treatment and applied topically to the hide, skin or hair of the animal. Such sprays or dips usually contain about 0.5 ppm to 5000 ppm and preferably about 1 ppm to 3000 ppm of the compound.

Advantageously, the formula I compound may also be prepared as a pour-on formulation and poured on the backs of the animals such as swine, cattle, sheep, horses, poultry and companion animals. Such pour-on compositions are generally prepared by dissolving, dispersing or emulsifying the formula I compound in a suitable nontoxic pharmacologically acceptable diluent for pour-on and administration. The diluent must be compatible with the compound and should not be a source of irritation or damage to the animals hide, skin or hair. Such diluents include vegetable oils, spreading oils, polyhydric alcohols, aliphatic or aromatic hydrocarbons, esters of fatty acids and lower alkyl ketones.

A typical pour-on formulation includes about 0.5% to 30% by weight of the formula I compound, about 30% to 60% by weight of an aliphatic or aromatic hydrocarbon, mono or polyhydric alcohol, lower alkyl ketone or mixtures thereof 0.0 to about 20% by weight of a vegetable or mineral oil and about 0.5% to 30% by weight of a spreading oil. Another typical pour-on contains about 45% by weight of xylene about 15% by weight of the formula I hydroxy furanone compound, about 10% by weight of corn oil or mineral oil, about 25% by weight of cyclohexanone and about 5% by weight of other pharmacologically acceptable spreading agents, antifoam agents, surfactants or the like.

Surprisingly, the formula I compounds of the invention wherein R is H, $COR_4$ or a $C_1$-$C_6$alkyl, $C_3$-$C_6$cycloalkyl, $C_2$-$C_6$alkenyl, $C_2$-$C_6$alkynyl, benzyl, aryl or heteroary group each optionally substituted, are useful for the control of plant parasitic nematodes and nematodes living freely in soil. Accordingly, in a further embodiment of the invention, there is provided a method for the control of nematode pests or parasites which comprises contacting said pests or parasites, their food supply, habitat or breeding ground with a pesticidally or parasiticidally effective amount of a compound of formula I

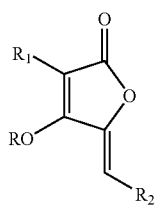

(I)

wherein

R is H, $COR_4$ or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_1$ is phenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, biphenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, naphthyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, or heteroaryl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_2$ is phenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl or heteroaryl group each optionally substituted;

biphenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

naphthyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

heteroaryl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl, phenyl or heteroaryl group each optionally substituted; or $C_3$-$C_6$cycloalkyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_3$, $R_4$, $R_9$, $R_{12}$, $R_{13}$ and $R_{18}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_5$, $R_7$, $R_{14}$ and $R_{16}$ are each independently a $C_1$-$C_6$alkyl, $C_3$-$C_6$cycloalkyl, $C_2$-$C_6$alkenyl, $C_2$-$C_6$alkyl, benzyl, aryl or heteroaryl group each optionally substituted;

$R_6$, $R_8$, $R_{15}$ and $R_{17}$ are each independently H or an optionally substituted $C_1$-$C_6$alkyl group; and $R_{10}$, $R_{11}$, $R_{19}$ and $R_{20}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted or $R_{10}$ and $R_{11}$ or $R_{19}$ and $R_{20}$ may be taken together with the atom to which they are attached to form an optionally substituted 5- to 7-membered ring optionally containing one or two additional heteroatoms selected from N, O or S; or a stereoisomer thereof, a tautomer thereof or a pharmaceutically acceptable salt thereof.

Plant parasitic nematodes include, but are not limited to, ectoparasites such as *Xiphinema* spp., *Longidorus* spp. and *Trichodorus* spp.; semi-parasites such as *Tylenchulus* spp.; migratory endoparasites such as *Pratylenchus* spp., *Radopholus* spp. or *Scutellonema* spp.; sedentary parasites such as *Heterodera* spp., *Globodera* spp. and *Meloidogyne* spp.; and stem and leaf endoparasites such as *Ditylenchus* sppp., *Aphelenchoides* spp. or *Hirshmaniella* spp.

In agronomic practice, generally about 0.1 ppm to 10,000 ppm, preferably about 1.0 ppm to 5,000 ppm, of a formula I compound dispersed in water or another liquid carrier, is effective when applied to plants or the soil or water in which the plants are growing or are to be grown to protect the plants from nematode attack or infestation. In this embodiment of the invention the compounds of formula I may be formulated as an emulsifiable concentrate, flowable concentrate, wettable powder, dilute spray, dry compacted granule, dust, suspension concentrate, microemulsion or any agronomic pesticidal composition which lends itself to seed, soil, water or foliage application and provides the requisite nematode control and plant protection.

Accordingly, in this further embodiment of the invention, there is provided a method for the protection of a growing or harvested plant from attack or infestation by nematode pests or parasites which comprises applying to the foliage of said plant or to the soil or water in which it is growing a pesticidally effective amount of a compound of formula I as described hereinabove and wherein R is H, $COR_4$ or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted.

When applied to the foliage of plants or to the soil or water in which the plants are growing or are to be grown, effective amounts may be that amount sufficient to provide about 0.1 kg/ha to 4.0 kg/ha of a compound of formula I.

For a more clear understanding, and in order to illustrate the invention more clearly, specific examples thereof are set forth hereinbelow. The following pxamples are merely illustrative and are not to be understood as limiting the scope and underlying principles of the invention in any way.

Unless otherwise stated, all parts are parts by weight. The term NMR designates nuclear magnetic resonance. The terms THF and EtOAc designate tetrahydrofuran and ethyl acetate, respectively. The term DMF designates dimethyl formamide and the term DMSO designates dimethylsulfoxide.

EXAMPLE 1

Preparation of 3-Bromo-5-(hydroxynaphthalen-1-ylmethyl)-4-methoxy-5H-furan-2-one

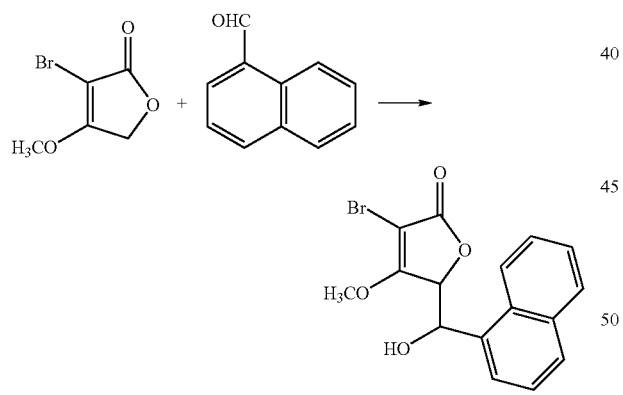

A solution of N-isopropylcyclohexylamine (3.62 g, 4.22 mL, 28.22 mmol) in THF at −78° C. is treated with n-butyl lithium (2.1M in hexane, 13.2 L), and stirred at −78° C. for 0.5 h. The resultant suspension is added dropwise to a suspension of 3-bromo-4-methoxy-5H-furan-2-one (4.95 g, 25.65 mmol) in THF at −78° C. The reaction mixture is stirred at −78° C. for 0.75 h, treated dropwise with a solution of 1-naphthylcarboxaldehyde (4.0 g, 25.65 mmol) in THF, stirred for 0.5 h at −78° C., allowed to warm to 0° C., quenched with saturated $NH_4Cl$ and extracted with EtOAc. The extracts are combined, dried over $MgSO_4$ and concentrated in vacuo. The resultant red oil residue is passed through a pad of silica gel using 100% hexanes and 80% EtOAc in hexanes as eluents to afford the title product as a yellow foam, 5.3 g (59% yield), identified by NMR and mass spectral analyses.

EXAMPLE 2

Preparation of 3-Bromo-4-methoxy-5[(Z)-1-naphthylmethylidene]furan-2(5H-one

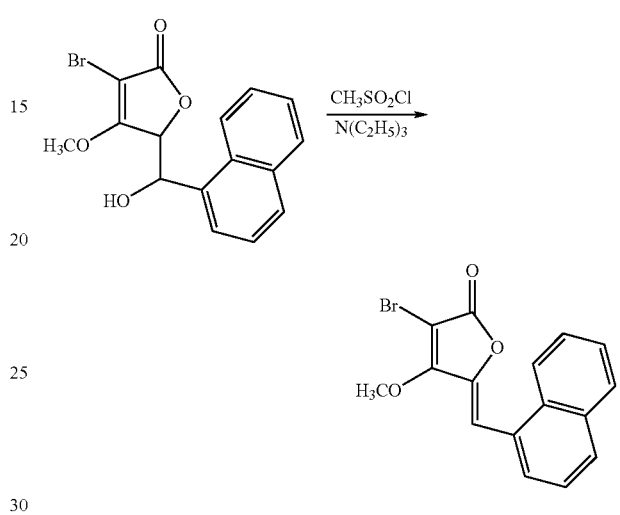

A solution of 3-bromo-5-(hydroxynaphthalen-1-ylmethyl)-4-methoxy-5H-furan-2-one (5.3 g, 15.17 mmol) and triethylamine (9.22 g, 12.7 mL, 91.1 mmol) in anhydrous $CH_2Cl_2$ at 0° C. is treated dropwise with methane sulfonyl chloride (6.96 g, 4.7 mL, 60.7 mmol), stirred for 0.5 h at 0° C., allowed to warm to room temperature, treated sequentially with additional triethylamine (4.64 g, 6.4 mL, 45.9 mmol) and methane sulfonyl chloride (3.55 g, 2.4 mL, 31 mmol), stirred until the disappearance of starting material and diluted with EtOAc and water. The phases are separated and the organic phase is dried over $Na_2SO_4$ and concentrated in vacuo. The resultant residue is flash chromatographed (silica gel, 25% EtOAc in hexanes as eluent) to afford the title product as a yellow solid, 4.0 g (80% yield), mp 143-148° C., identified by NMR and mass spectral analyses.

EXAMPLE 3

Preparation of 3-(4-Chlorophenyl)-4-methoxy-5-[(Z)-1-naphthylmethyl-idene]furan-2(5H)-one

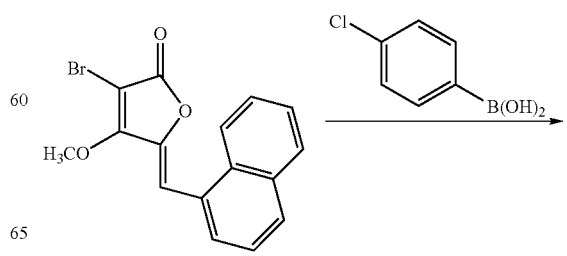

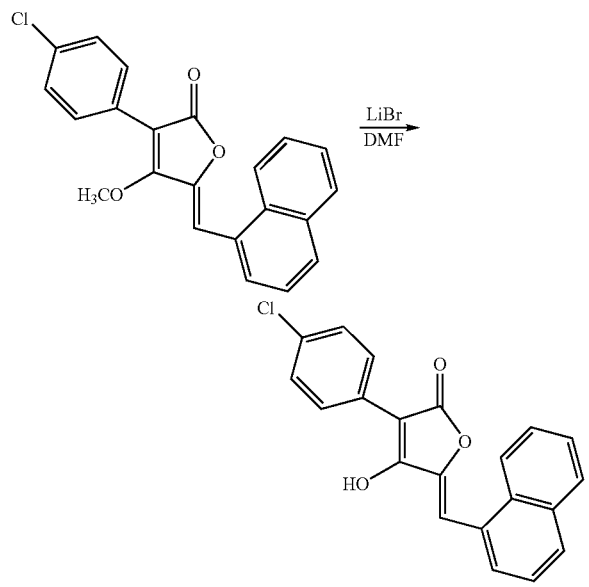

A stirred mixture of 4-chlorophenylboronic acid (259 mg, 166 mmol), $K_3PO_4$ (962 mg, 4.53 mmol) and $Pd(PPh_3)_4$ (52 mg, 45.3 µmol) under $N_2$ is treated sequentially with of 3-bromo-4-methoxy-5[(Z)-1-naphthylmethylidene]furan-2 (5H)-one (500 mg, 1.51 mmol) and 9.3 mL of a 2:1 v/v mixture of dioxane/THF, heated at 90° C. until the disappearance of starting material by thin layer chromatography, cooled to room temperature, diluted with water and extracted with EtOAc. The extracts are combined, dried over $MgSO_4$ and concentrated in vacuo. The resultant residue is purified by flash chromatography (silica gel, 25% EtOAc in hexanes as eluent) to afford the title product as a yellow solid, 380 mg (69% yield), identified by NMR and mass spectral analyses.

EXAMPLE 4

Preparation of 3-(4-Chlorophenyl)-4-hydroxy-5-[(Z)-1-naphthylmethylidene]-furan-2-(5H)-one A stirred mixture of 3-(4-chlorophenyl)-4-methoxy-5-[(Z)-1-naphthylmethyl-idene]furan-2(5H)-one (380 mg, 0.998 mmol) and LiBr (86.6 mg, 0.998 mmol) in DMF is heated at 150° C. for 10 min., cooled to room temperature, poured into 5 mL $H_2SO_4$, diluted with water and extracted with EtOAc. The extracts are combined, washed with water, dried over $Na_2SO_4$ and concentrated in vacuo. The resultant oil residue is passed through a silica gel pad, using a gradient elution of 100% EtOAc to 9:1 EtOAc:2.5% acetic acid in methanol, to afford the title product as a rust-yellow solid, 270 mg (78% yield), mp 220°-224° C., identified by NMR and mass spectral analyses.

EXAMPLES 5-96

Preparation of 3-Aryl-4-hydroxyfuranone Derivatives

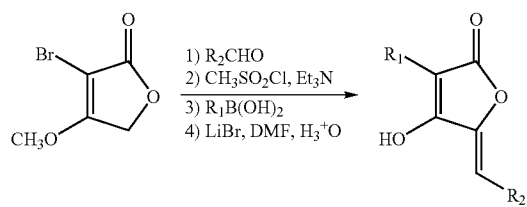

Using essentially the same procedures described in Examples 1-4 and employing a suitable arylcarboxaldehyde and the appropriate boronic acid derivative, the compounds shown on Table I are obtained and identified by NMR and mass spectral analyses. Unless otherwise noted, all compounds on Table I are the Z isomer.

TABLE I

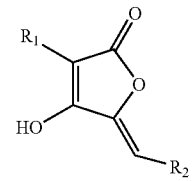

| Ex. No. | $R_1$ | $R_2$ | mp ° C. |
|---|---|---|---|
| 5 | 3-$CF_3$—$C_6H_4$ | 1-naphthyl | 100 (dec) |
| 6 | 4-$CH_3O$—$C_6H_4$ | 1-naphthyl | 218-222 |
| 7 | 4-$CH_3O$—$C_6H_4$ | 2-naphthyl | 257-258.5 |
| 8 | 3-$CF_3$—$C_6H_4$ | 2-naphthyl | 239-240.8 |
| 9 | 4-$CH_3O$—$C_6H_4$ | 4-biphenyl | 266-269 |
| 10 | 3-$CF_3$—$C_6H_4$ | 4-biphenyl | 240-241.5 |
| 11 | 3-$CF_3$—$C_6H_4$ | 4-biphenyl[a] | 230 |
| 12 | 3-$CF_3$—$C_6H_4$ | 5-methylthien-2-yl | 249-251 |
| 13 | 4-Cl—$C_6H_4$ | 5-methylthien-2-yl[a] | 257 (dec) |
| 14 | 4-Cl—$C_6H_4$ | 5-methylthien-2-yl[b] | 256-258 |
| 15 | 4-Cl—$C_6H_4$ | cyclohexyl | 200-205 |
| 16 | 3-$CF_3$—$C_6H_4$ | cyclohexyl[c] | 185-192 |
| 17 | 3-$CF_3$—$C_6H_4$ | cyclohexyl | 170-173.5 |
| 18 | 3-Cl—$C_6H_4$ | 4-(2'-Cl—2$CH_3O$-biphenyl) | 212-215 |
| 19 | 3,5-diCl—$C_5H_3$ | 4-(2,2'-di$CH_3O$-biphenyl) | 202-205 |
| 20 | 3,4-diCl—$C_6H_3$ | 4-(2,2'-di$CH_3O$-biphenyl) | 221-223 |
| 21 | 3,5-diCl—$C_6H_3$ | 4-(2'-Cl-2-$CH_3O$-biphenyl) | 223-225 |
| 22 | 3-Cl—$C_6H_4$ | 4-(2-$CH_3O$-2'-$CH_3$-biphenyl) | 176-180 |
| 23 | 3-Cl—$C_6H_4$ | 4-(2'-$CH_3O$-2-$CH_3$-biphenyl) | 223-224 |
| 24 | 3,5-diCl—$C_6H_3$ | 4-(2'-$CH_3O$-2-$CH_3$-biphenyl) | 215-219 |
| 25 | 3,5-diCl—$C_6H_3$ | 4-(2-$CH_3O$-2'-$CH_3$-biphenyl) | 140-150 |
| 26 | 3-Cl—$C_6H_4$ | 4-(2-$CH_3$-2'-$CF_3$-biphenyl) | 218-222 |
| 27 | 3,5-diCl—$C_6H_3$ | 4-(2-$CH_3$-2'-$CF_3$-biphenyl) | 223-228 |
| 28 | 3-Cl—$C_6H_4$ | 4-(2,2'-di-$CH_3$-biphenyl) | 219-222 |
| 29 | 3,5-diCl—$C_6H_3$ | 4-(2,2'-di-$CH_3$-biphenyl) | 228-231 |
| 30 | 3-Cl—$C_6H_4$ | 4-(2'-Cl-2-$CH_3$-biphenyl) | 211-215 (dec) |
| 31 | 3,5-diCl—$C_6H_3$ | 4-(2'-Cl-2-$CH_3$-biphenyl)[c] | 230-235 |

TABLE I-continued

| Ex. No. | R₁ | R₂ | mp °C. |
|---|---|---|---|
| 32 | 3-Cl—C₆H₄ | 4-(2-CH₃O-2'-CF₃-biphenyl) | 219-222 |
| 33 | 3,5-diCl—C₆H₃ | 4-(2-CH₃O-2'-CF₃-biphenyl) | 219-222 |
| 34 | 3,5-diCl—C₆H₃ | 4-[3-F-(4-morpholin-4-yl)phenyl] | 262-265 |
| 35 | 3-Cl—C₆H₄ | 1-(4-methoxynaphthyl)$^d$ | 233 (dec) |
| 36 | 3,5-di-Cl—C₆H₃ | 1-(4-methoxynaphthyl) | 276-278 |
| 37 | 3-Cl—C₆H₄ | 1-[(4-morpholin-4-yl)naphthyl] | 239-241 |
| 38 | 3,5-diCl—C₆H₃ | 1-[(4-morpholin-4-yl)naphthyl] | 253-256 |
| 39 | 3,5-diCl—C₆H₃ | 4-(2-CH₃-2'CH₃SO₃-biphenyl) | 221-229 |
| 40 | 3,5-diCl—C₆H₃ | 4-(2'-CH₃CO-2-CH₃-biphenyl) | 223-225 |
| 41 | 2-naphthyl | 5-methylthien-2-yl | 144-145 (dec) |
| 42 | 2-naphthyl | 3-CF₃—C₆H₄ | 185-189 |
| 43 | 2-naphthyl | 4-Cl—C₆H₄ | 243-250 |
| 44 | 2-naphthyl | 1-naphthyl | 205-207 |
| 45 | 2-naphthyl | 4-biphenyl | 200-203 (dec) |
| 46 | 1-naphthyl | 4-Cl—C₆H₄ | 235-237 |
| 47 | 1-naphthyl | 1-naphthyl | 216-218 |
| 48 | 1-naphthyl | 3-CF₃—C₆H₄ | 173-176 |
| 49 | 1-naphthyl | 3-CF₃—C₆H₄$^e$ | 224-226 |
| 50 | 1-naphthyl | 4-biphenyl | 249-253 |
| 51 | 2-naphthyl | Cyclohexyl | 205-208 |
| 52 | 2-naphthyl | 2-naphthyl | 285-290 |
| 53 | 4-Cl—C₆H₄ | 4-biphenyl | 282-285 |
| 54 | 4-Cl—C₆H₄ | 2-naphthyl | 284-286 |
| 55 | 3-CF₃—C₆H₄ | 4-(3'-CF₃-biphenyl) | 220-225 |
| 56 | 1-naphthyl | 2-naphthyl | 235-237 |
| 57 | 4-CH₃—C₆H₄ | 4-(4'-CH₃-biphenyl) | 261-265 |
| 58 | 2-F—C₆H₄ | 4-(2'-F-biphenyl) | 234-236 |
| 59 | 2-CN—C₆H₄ | 4-(3'-CN-biphenyl) | 259-263 |
| 60 | 2-CH₃—C₆H₄ | 4-(2'-CH₃-biphenyl) | 164-167 |
| 61 | 2-CF₃—C₆H₄ | 4-(2'-CF₃-biphenyl) | 210-213 |
| 62 | 4-CN—C₆H₄ | 4-(4'-CN-biphenyl) | 238-240 |
| 63 | 3,5-di-Cl—C₆H₃ | 4-(3',5'-di-Cl-biphenyl) | 236-240 |
| 64 | 4-Cl—C₆H₄ | 4-(4'-Cl-biphenyl) | 276-280 |
| 65 | 2,4-di-Cl—C₆H₄ | 4-biphenyl | 252-256 |
| 66 | 3,4-di-Cl—C₆H₄ | 4-biphenyl | 265-269 |
| 67 | 3,5-di-Cl—C₆H₃ | 4-biphenyl | 279-280 |
| 68 | 3,5-di-Cl—C₆H₃ | 4-biphenyl | 232-235 |
| 69 | 3-Cl—C₆H₄ | 4-biphenyl | 248-250 |
| 70 | 3,5-di-Cl—C₆H₃ | 1-naphthyl | 244-245 |
| 71 | 4-CF₃-C₆H₄ | 1-naphthyl | 245-247 |
| 72 | 3-CH₃O—C₆H₄ | 1-naphthyl | 214-216 |
| 73 | 4-[(1Z)CNOH—C₆H₄] | 1-naphthyl$^f$ | 209-211 |
| 74 | 4-CO₂CH₃—C₆H₄ | 1-naphthyl | 242-244 |
| 75 | 3-CO₂C₂H₅—C₆H₄ | 1-naphthyl$^g$ | 169-171 |
| 76 | 3-CHO—C₆H₄ | 1-naphthyl | 220-221 |
| 77 | 3-CNOH-C₆H₄ | 1-naphthyl | 213-215 |
| 78 | 4-Cl—C₆H₄ | 1-[(4-dimethylamino)naphthyl] | 228 |
| 79 | 3,5-di-Cl—C₆H₃ | 1-[(4-dimethylamino)naphthyl] | 168-194 |
| 80 | 3,5-di-Cl—C₆H₃ | 1-[(4-dimethylamino)naphthyl]$^h$ | 167-172 |
| 81 | 4-CF₃—C₆H₄ | 1-[(4-dimethylamino)naphthyl] | 234-237 |
| 82 | 3-CF₃—C₆H₄ | 3-CF₃—C₆H₄ | 221-224 |
| 83 | 4-Cl—C₆H₄ | 3-CF₃—C₆H₄ | 216-220 |
| 84 | 4-CH₃O—C₆H₄ | 3-CF₃—C₆H₄ | 200-226 (dec) |
| 85 | 4-Cl—C₆H₄ | 4-Cl—C₆H₄ | 261-264 |
| 86 | 3-CF₃—C₆H₄ | 4-Cl—C₆H₄ | 233-236 |
| 87 | 4-CH₃O—C₆H₄ | 4-Cl—C₆H₄ | 272-275 |
| 88 | 4-CH₃O—C₆H₄ | 4-CH₃O—C₆H₄ | 245 |
| 89 | 4-CH₃O—C₆H₄ | 4-CH₃O—C₆H₄$^a$ | 163-167 |
| 90 | 3-CF₃—C₆H₄ | 4-CH₃O—C₆H₄ | 221-225 |
| 91 | 3,5-diCl—C₆H₃ | 4-[3-F-(4-piperizin-4-yl-1-ethylcarboxylate)phenyl] | 246-249 |
| 92 | 3-Cl—C₆H₄ | 4-[3-F-(4-piperizin-4-yl-1-ethylcarboxylate)phenyl] | 226-228 |
| 93 | 3,5-diCl—C₆H₃ | 3-(benzyloxy)phenyl | 198-200 |
| 94 | 3,5-diCl—C₆H₃ | 2-(benzyloxy)phenyl | — |
| 95 | 3,5-diCl—C₆H₃ | 4-{3-Cl-[4-(2-Cl—C₆H₄)piperazin-1-yl]phenyl} | 259-261 |
| 96 | 3,5-diCl—C₆H₃ | 3-{[(2R)2-methylcarboxylate]-piperidinyl-1-carbonyl}phenyl | 226 |

$^a$4.25:1 E:Z isomer mixture
$^b$35:1 Z:E isomer mixture
$^c$E isomer
$^d$3:1 Z:E isomer mixture
$^e$7:1 E:Z isomer mixture
$^f$1:1.55 E:Z isomer mixture
$^g$E Z isomer mixture
$^h$1:1 E:Z isomer mixture

EXAMPLE 97

Preparation of 5-{Hydroxy-[2-(trifluoromethyl)phenyl]methyl}4-methoxy-5H-furan-2-one

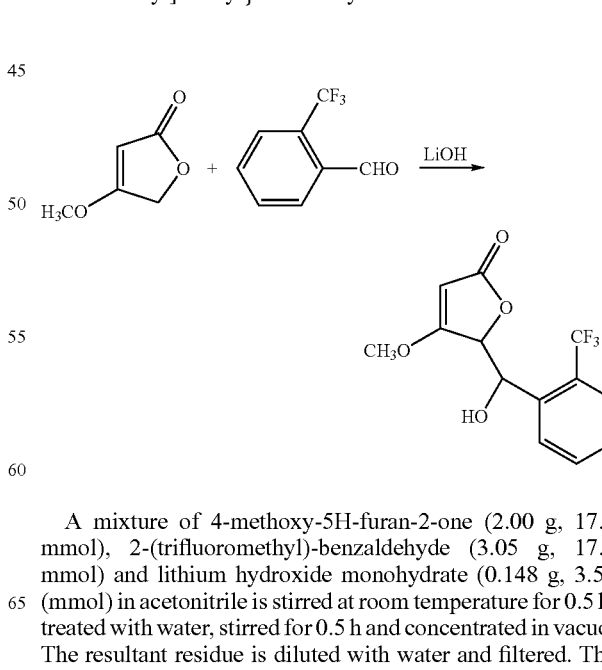

A mixture of 4-methoxy-5H-furan-2-one (2.00 g, 17.5 mmol), 2-(trifluoromethyl)-benzaldehyde (3.05 g, 17.5 mmol) and lithium hydroxide monohydrate (0.148 g, 3.53 mmol) in acetonitrile is stirred at room temperature for 0.5 h, treated with water, stirred for 0.5 h and concentrated in vacuo. The resultant residue is diluted with water and filtered. The filtercake is dried in vacuo to give the title product as a white solid, 3.00 g (59% yield), mp 126-128° C., identified by NMR and mass spectral analyses.

EXAMPLE 98

Preparation of 3-Bromo-4-methoxy-5-{(Z)-2-(trifluoromethyl)benzylidenel}-5H-furan-2-one

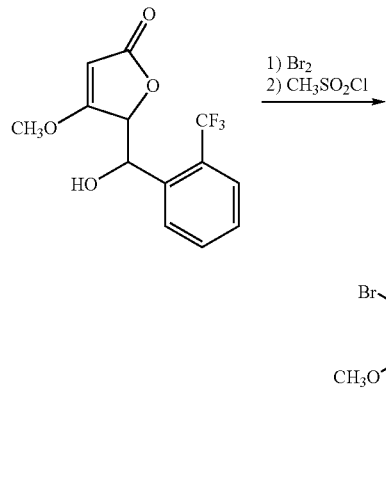

A stirred solution of 5-{hydroxy-[2-(trifluoromethyl)phenyl]methyl}-4-methoxy-5H-furan-2-one (2.9 g, 10.1 mmol) in acetonitrile at room temperature is treated dropwise with bromine (0.52 ml, 10.1 mmol), stirred for 24 h and concentrated in vacuo. The resultant residue is diluted with $CH_2Cl_2$ and triethylamine (4.25 ml), cooled in an ice bath, treated with methane sulfonyl chloride (1.6 ml), stirred for 0.5 h at ice bath temperatures, allowed to warm to room temperature for 2 h and diluted with EtOAc and water. The organic chase is separated, dried over $MgSO_4$ and concentrated in vacuo. This residue is flash chromatographed ($SiO_2$, hexane/EtOAc as eluent) to afford the title product as a white solid, 0.20 g (6% yield), mp 136-138° C., identified by NMR and mass spectral analyses.

EXAMPLE 99

Preparation of 3-[1.1'-Biphenyl]-4-yl-4-hydroxy-5-{(Z)-[2-(trifluoromethyl) benzylidene]}-5H-furan-2-one

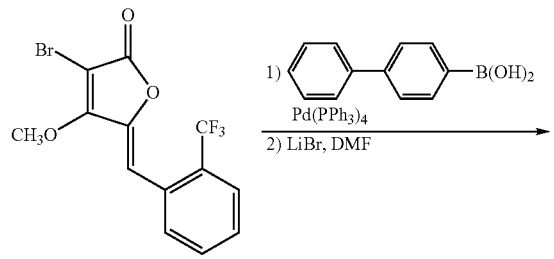

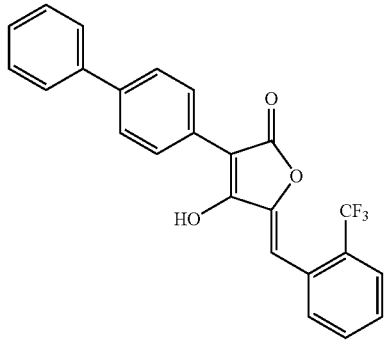

Using essentially the same procedures described in Examples 3 and 4 hereinabove and employing the 3-bromofuranone of Example 83 and 4-biphenylboronic acid as reagents, the title product is obtained as white solid, mp 228-230° C., identified by NMR and mass spectral analyses.

EXAMPLES 100-162

Preparation of 3-Aryl-4-hydroxyfuranone Derivatives

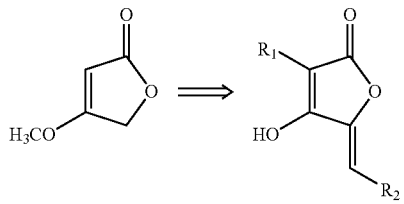

Using essentially the same procedures described in Examples 1-4 and 82-84 and employing a suitable arylcarboxaldehyde and appropriate boronic acid derivative, the compounds shown on Table II are obtained and identified by NMR and mass spectral analyses. Unless otherwise noted, all compounds on Table II are the Z isomer.

TABLE II

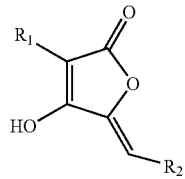

| Ex. No. | $R_1$ | $R_2$ | mp ° C. |
|---|---|---|---|
| 100 | 4-biphenyl | cyclohexyl | 204-207 |
| 101 | 4-biphenyl | 3-pyridyl | 252-255 |
| 102 | 4-biphenyl | 1-naphthyl | 226-230 |
| 103 | 4-biphenyl | 2-naphthyl | 266-270 |
| 104 | 4-biphenyl | 5-methylthien-2-yl | 235-240 |
| 105 | 4-biphenyl | 4-$CF_3$—$C_6H_4$ | 250-255 |
| 106 | 4-(2-F-biphenyl) | 3-$CF_3$—$C_6H_4$ | 222-226 |
| 107 | 4-(2-F-biphenyl) | 2-$CF_3$—$C_6H_4$ | 224-228 |
| 108 | 3-biphenyl | 3-$CF_3$—$C_6H_4$ | 210-212 |
| 109 | 3-biphenyl | 3-F-5-$CF_3$—$C_6H_3$ | — |
| 110 | 4-(2-F-biphenyl) | 3-F-5-$CF_3$—$C_6H_3$ | — |

TABLE II-continued

| Ex. No. | R₁ | R₂ | mp °C. |
|---|---|---|---|
| 111 | 4-(4'-propylbiphenyl) | 3-F-5-CF$_3$—C$_6$H$_3$ | — |
| 112 | 3-biphenyl | 3-F-5-CF$_3$—C$_6$H$_3$ | — |
| 113 | 4-biphenyl | 2-Cl-3-CF$_3$—C$_6$H$_3$ | — |
| 114 | 4-(2-F-biphenyl) | 2-Cl-3-CF$_3$—C$_6$H$_3$ | — |
| 115 | 4-(4'-propylbiphenyl) | 2-Cl-3-CF$_3$—C$_6$H$_3$ | — |
| 116 | 4-(4'-t-butylbiphenyl) | 2-Cl-3-CF$_3$—C$_6$H$_3$ | — |
| 117 | 4-(4'-C$_2$H$_5$O-biphenyl) | 2-Cl-3-CF$_3$—C$_6$H$_3$ | — |
| 118 | 4-biphenyl | 2-F-5-CF$_3$—C$_6$H$_3$ | — |
| 119 | 4-(2-F-biphenyl) | 2-F-5-CF$_3$—C$_6$H$_3$ | — |
| 120 | 4-(4'-t-butylbiphenyl) | 2-F-5-CF$_3$—C$_6$H$_3$ | — |
| 121 | 3-biphenyl | 2-F-5-CF$_3$—C$_6$H$_3$ | — |
| 122 | 4-(4'-C$_2$H$_5$O-biphenyl) | 2-F-5-CF$_3$—C$_6$H$_3$ | — |
| 123 | 4-(4'-t-butylbiphenyl) | 4-Cl-3-CF$_3$—C$_6$H$_3$ | — |
| 124 | 4-(4'-C$_2$H$_5$O-biphenyl) | 4-Cl-3-CF$_3$—C$_6$H$_3$ | — |
| 125 | 4-biphenyl | 2-Cl-5-CF$_3$—C$_6$H$_3$ | — |
| 126 | 4-(2-F-biphenyl) | 2-Cl-5-CF$_3$—C$_6$H$_3$ | — |
| 127 | 4-(4'-propylbiphenyl) | 2-Cl-5-CF$_3$—C$_6$H$_3$ | — |
| 128 | 4-(4'-t-butylbiphenyl) | 2-Cl-5-CF$_3$—C$_6$H$_3$ | — |
| 129 | 4-(4'-C$_2$H$_5$O-biphenyl) | 2-Cl-5-CF$_3$—C$_6$H$_3$ | — |
| 130 | 4-biphenyl | 3-CF$_3$—C$_6$H$_4$ | — |
| 131 | 4-(4'-propylbiphenyl) | 3-CF$_3$—C$_6$H$_4$ | — |
| 132 | 4-(4'-t-butylbiphenyl) | 3-CF$_3$—C$_6$H$_4$ | — |
| 133 | 4-(4'-C$_2$H$_5$O-biphenyl) | 3-CF$_3$—C$_6$H$_4$ | — |
| 134 | 3-Cl—C$_6$H$_4$ | 3-(3'-Cl-biphenyl) | 191-193 |
| 135 | 3,4-di-Cl—C$_6$H$_3$ | 3-(3',4'-di-Cl-biphenyl) | 214-216 |
| 136 | 3,5-di-Cl—C$_6$H$_3$ | 3-(3',5'-di-Cl-biphenyl) | 233-236 |
| 137 | 4-Cl—C$_6$H$_4$ | 2-(4'-Cl-biphenyl) | 230-232 |
| 138 | 4-(2-F-biphenyl) | 4-Cl—C$_6$H$_4$ | 255-258 |
| 139 | 4-biphenyl | 4-Cl—C$_6$H$_4$ | 280-282 |
| 140 | 3-Cl—C$_6$H$_4$ | 2-(3'-Cl-biphenyl) | 218-221 |
| 141 | 3,4-di-Cl—C$_6$H$_3$ | 2-(3',4'-di-Cl-biphenyl) | 237-239 |
| 142 | 4-[3-F-(4-morpholin-4-yl)-C$_6$H$_3$] | 2-Cl-5-CF$_3$—C$_6$H$_3$ | 232-234 |
| 143 | benzo[b]thiophen-3-yl | 4-biphenyl | 270 |
| 144 | thiophen-2-yl | 4-biphenyl | 213 (dec) |
| 145 | 4-CN—C$_6$H$_4$ | 2-CF$_3$—C$_6$H$_4$ | 147-150 |
| 146 | 4-F—C$_6$H$_4$ | 2-CF$_3$—C$_6$H$_4$ | 147-150 |
| 147 | 3-biphenyl | 3-CF$_3$—C$_6$H$_4$ | 210-212 |
| 148 | 2,5-di-CH$_3$—C$_6$H$_3$ | 2-Cl-5-CF$_3$—C$_6$H$_3$ | — |
| 149 | 3-CH$_3$—C$_6$H$_4$ | 2-Cl-5-CF$_3$—C$_6$H$_3$ | — |
| 150 | 4-isopropyl-C$_6$H$_4$ | 2-Cl-5-CF$_3$—C$_6$H$_3$ | — |
| 151 | 3-isopropyl-C$_6$H$_4$ | 2-Cl-3-CF$_3$—C$_6$H$_3$ | — |
| 152 | 4-C$_2$H$_5$—C$_6$H$_4$ | 2-Cl-3-CF$_3$—C$_6$H$_3$ | — |
| 153 | 4-CH$_3$—C$_6$H$_4$ | 2-Cl-3-CF$_3$—C$_6$H$_3$ | — |
| 154 | 3,4-di-CH$_3$—C$_6$H$_3$ | 2-Cl-3-CF$_3$—C$_6$H$_3$ | — |
| 155 | 3-CH$_3$—C$_6$H$_4$ | 2-Cl-3-CF$_3$—C$_6$H$_3$ | — |
| 156 | C$_6$H$_5$ | 3-CF$_3$—C$_6$H$_4$ | 224-226 |
| 157 | 3,5-di-Cl—C$_6$H$_3$ | 3-{[(S)-1-phenethyl]NHSO$_2$}-C$_6$H$_4$ | 175-178 |
| 158 | 3,5-di-Cl—C$_6$H$_3$ | 3-{[(R)-1-phenethyl]urea}-C$_6$H$_4$ | 195-198 |
| 159 | 3,5-di-Cl—C$_6$H$_3$ | 3-{[(S)-1-phenethyl]urea}-C$_6$H$_4$ | 210-212 |
| 160 | 3,5-di-Cl—C$_6$H$_3$ | 2-Cl-5-CF$_3$—C$_6$H$_3$ | 244-247 |
| 161 | 3,5-di-Cl—C$_6$H$_3$ | 4-benzyloxy-3-CH$_3$O—C$_6$H$_3$ | 105-110 |
| 162 | 3,5-di-Cl—C$_6$H$_3$ | 3-benzyloxy-4-CH$_3$O—C$_6$H$_3$ | 214 (dec) |

EXAMPLE 163

Preparation of (5E)-(4-cyanobenzylidine)-3-(4-cyanophenyl)-4-hydroxyfuran-2(5H)-one

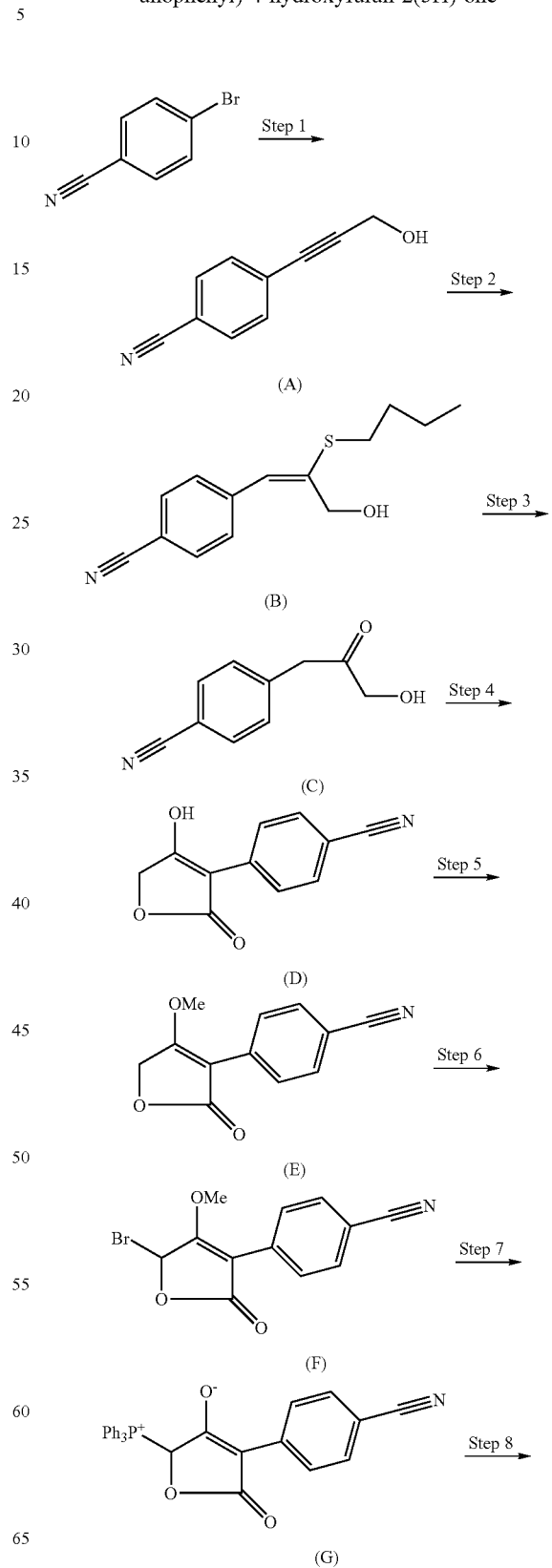

-continued

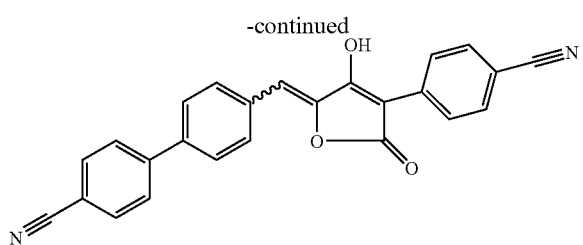

STEP 1: A solution of 4-bromobenzonitrile (9.22 grams, 50.7 mmol), copper(I) iodide (0.63 grams, 3.3 mmol), triphenylphoshine (2.0 grams, 7.6 mmol) and palladium acetate (0.56 grams, 2.5 mmol) in 30 ml of THF is purged with nitrogen, treated with 20 ml of N-butylamine (202.4 mmol), stirred for 10 minutes, treated with 3.0 ml of propargyl alcohol (50.7 mmol), stirred at ambient temperatures for 3 h, treated with silica gel (20 grams) and concentrated under reduced pressure. The residue is purified by flash column chromatography (50% ether in hexane) to afford the desired product A in 91% yield (7.30 grams).

Reference: U.S. Pat. No. 6,239,280

Step 2: A mixture of the product A from above (7.00 grams, 44.6 mmol) and KOH (0.5 grams, 8.9 mmol) in acetonitrile is treated dropwise over 30 minutes with n-butylthiol 5.9 ml, 55.3 mmol), stirred for an additional 30 minutes, treated with silica gel (15 grams) and concentrated under reduced pressure. The residue is purified by flash column chromatography (50% ether in hexane) to give the desired product B in 71% yield (7.85 grams).

Reference : Tetrahedron Lett., 41, 141, 2000.

Step 3: A solution of the product B from above (7.50 grams, 30.4 mmol) in ethanol and 20 ml of 1N sulfuric acid is heated at 75° C. for 48 hours, cooled to ambient temperature and diluted with a mixture of ethyl acetate and brine. The organic phase is separated and dried over anhydrous sodium sulfate. Silica gel (10 grams) is added and the resultant mixture is concentrated under reduced pressure. The residue is purified by flash column chromatography (100% $CH_2Cl_2$) to give the desired product C in 72% yield (3.85 grams).

Reference: Tetrahedron Lett., 41, 141, 2000.

Step 4: A 2 M solution of lithium diisopropylamine (LDA) (27. 5 ml, 55 mmol) is added to 100 ml of THF at −78° C. A solution of the product C from above (3.85 grams, 22 mmol) in 50 ml of THF is added to the LDA solution over 30 minutes at −78° C., stirred for another hour at −78° C., treated portionwise with carbonyl diimidazole (8.91 grams, 55 mmol) over 30 minutes, stirred for an additional 2 hours at −78° C., warmed to ambient temperature, stirred an additional hour, diluted with 60 ml of 3 M sulfuric acid and 100 ml of brine. The organic phase is separated and dried over anhydrous sodium sulfate. Silica gel (10 grams) is added and the mixture is concentrated under reduced pressure. Flash column chromatography (80% acetone in hexane) of the residue gives the desired product D in 37% yield (1.65 grams).

Reference: Tetrahedron Lett., 20, 4517, 1979.

Step 5: A solution of the product D from above (3.30 grams, 16.4 mmol) and potassium carbonate 2.04 grams, 14.8 mmol) in acetone is treated with dimethyl sulfate (3.5 ml), heated at reflux temperature for 1.5 hours, cooled to ambient temperature, treated with silica gel (5 grams) and concentrated under reduced pressure. Flash column chromatography (100% $CH_2Cl_2$) of the residue gives the desired product E in 64% yield (2.25 grams).

Reference: J. Chem. Soc. Perkin Trans. I, 1567, 1985.

Step 6: The product E from above (1.80 grams, 8.37 mmol) is dissolved in 1,2-dichloroethane heated to reflux temperature treated portionwise with N-bromo-succinimide (1.60 grams, 8.96 mmol) and AIBN (50 mg) over a 2 hour period, cooled and diluted with a mixture of $CH_2Cl_2$ and water. The organic phase is separated, dried over anhydrous sodium sulfate, treated with silica gel (5 grams) and concentrated under reduced pressure. Flash column chromatography (100% $CH_2Cl_2$) of the residue gives the desired product F in 67% yield (1.65 grams).

Reference: J. Chem. Soc. Perkin Trans. I, 1567, 1985.

Step 7: The product F from above (1.65 grams, 5.63 mmol) is dissolved in toluene and heated to 85° C., treated dropwise with a solution of triphenylphosphine (1.85 grams, 7.04 mmol) in toluene, stirred at 85° C. for 2 hours, cooled and filtered. The solid filtercake is dried under suction to give the desired product G in 85% yield (2.23 grams).

Reference: J. Chem. Soc. Perkin Trans. I, 1567, 1985.

Step 8: A solution of sodium (0.11 grams, 4.77 mmol) in ethanol is treated sequentially with 4'-cyano-4-phenyl benzaldehyde (1.03 grams, 4.96 mmol) and the product G from above(2.00 grams, 4.34 mmol), stirred at ambient temperature for 2 hours, and diluted with a mixture of water and toluene. The aqueous layer is separated, acidified to pH 1.0 with 4 N HCl and filtered. The solid filtercake is suction dried, washed twice with toluene and suction dried again to give the title product as a 7 to 1 mixture of Z to E isomers in 41% yield (0.68 grams). The two isomers may be separated by washing the E isomer out with chloroform.

Reference: J. Chem. Soc. Perkin Trans. I, 1567, 1985.

EXAMPLES 164-226

Preparation of 3-Aryl-4-hydroxyfuranone Derivatives

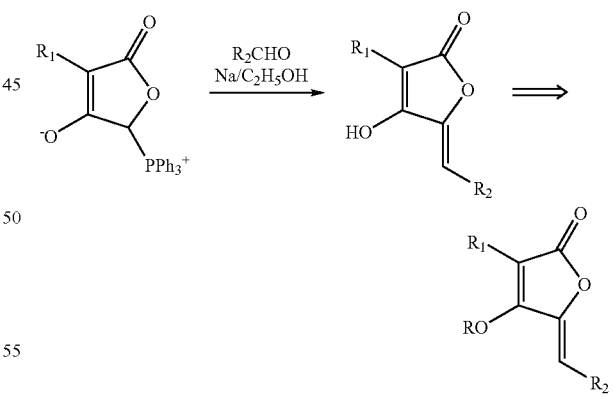

Using essentially the same procedures described in Example 163 hereinabove and employing a suitable arylcarboxaldehyde and appropriate Wittig reagent, and alkylating or acylating the 4-hydroxy group using conventional techniques, the compounds shown on Table III are obtained and identified by NMR and mass spectral analyses. Mass ions of the compounds are either M−H/M+H/M+ Na or M+ depending upon method used. Example 174 is M-$CO_2$ tBu. Unless otherwise noted, all compounds on Table III are the Z isomer.

TABLE III

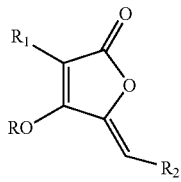

| Ex. No. | R | $R_1$ | $R_2$ | Mass Ion |
|---|---|---|---|---|
| 164 | H | 4-CN—$C_6H_4$* | 4-(4'-CN-biphenyl) | 389 |
| 165 | H | 4-CN—$C_6H_4$ | 4-Cl—$C_6H_4$ | 323 |
| 166 | H | 4-CN—$C_6H_4$ | 4-CN—$C_6H_4$ | 314 |
| 167 | H | 4-CN—$C_6H_4$ | 4-(4'-Cl-biphenyl) | 398 |
| 168 | H | 4-Cl—$C_6H_4$ | 4-(4'-CN-biphenyl) | 399 |
| 169 | H | 4-Cl—$C_6H_4$* | 4-(4'-CN-biphenyl) | 399 |
| 170 | H | 4-Cl—$C_8H_4$** | 4-CN—$C_6H_4$ | 323 |
| 171 | H | 4-Cl—$C_6H_4$ | 3-Cl—$C_6H_4$ | 332 |
| 172 | H | 3-$CF_3$—$C_6H_4$ | 4-Cl—$C_6H_4$ | *** |
| 173 | $CH_3$ | 4-Cl—$C_6H_4$ | 4-CN—$C_6H_4$ | 338 |
| 174 | $CO_2$t-Bu | 4-Cl—$C_6H_4$** | 4-CN—$C_6H_4$ | 322 |
| 175 | $CO_2C_6H_5$ | 4-Cl—$C_6H_4$** | 4-CN—$C_6H_4$ | 450 |
| 176 | $CO_2CH_3$ | 4-Cl—$C_6H_4$** | 4-CN—$C_6H_4$ | 388 |
| 177 | $CH_2CH=CH_2$ | 4-Cl—$C_6H_4$** | 4-CN—$C_6H_4$ | 364 |
| 178 | H | 4-$CF_3$—$C_6H_4$** | 4-CN—$C_6H_4$ | 356 |
| 179 | H | 4-$CF_3$—$C_6H_4$** | 4-Cl—$C_6H_4$ | 367 |
| 180 | H | 4-$CF_3$—$C_6H_4$** | 4-$CF_3$—$C_6H_4$ | 399 |
| 181 | H | 4-$CF_3$—$C_6H_4$** | 4-(4'-Cl-biphenyl) | 441 |
| 182 | H | 4-$CF_3$—$C_6H_4$** | 4-(4'-CN-biphenyl) | 432 |
| 183 | H | 4-$CF_3$—$C_6H_4$** | 4-F—$C_6H_4$ | 349 |
| 184 | H | 4-F—$C_6H_4$** | 4-CN—$C_6H_4$ | 306 |
| 185 | H | 4-F—$C_6H_4$** | 4-Cl—$C_6H_4$ | 315 |
| 186 | H | 4-F—$C_6H_4$** | 4-$CF_3$—$C_6H_4$ | 349 |
| 187 | H | 4-F—$C_6H_4$** | 4-F—$C_6H_4$ | 299 |
| 188 | H | 4-F—$C_6H_4$ | 4-(4'-CN-biphenyl) | 382 |
| 189 | H | 4-F—$C_6H_4$** | 4-(4'-Cl—biphenyl) | 391 |
| 190 | H | 3-Cl—$C_6H_4$** | 4-CN—$C_6H_4$ | 322 |
| 191 | H | 3-Cl—$C_6H_4$** | 4-Cl—$C_6H_4$ | 331 |
| 192 | H | 3-Cl—$C_6H_4$** | 4-$CF_3$—$C_6H_4$ | 365 |
| 193 | H | 3-Cl—$C_6H_4$** | 4-(4'-Cl-biphenyl) | 407 |
| 194 | H | 3-Cl—$C_6H_4$** | 4-(4'-CN-biphenyl) | 398 |
| 195 | H | 3-Cl—$C_6H_4$** | 4-F—$C_6H_4$ | 315 |
| 196 | H | 3-$CF_3$—$C_6H_4$** | 4-CN—$C_6H_4$ | 356 |
| 197 | H | 3-$CF_3$—$C_6H_4$** | 4-F—$C_6H_4$ | 349 |
| 198 | H | 3-$CF_3$—$C_6H_4$** | 4-$CF_3$—$C_6H_4$ | 399 |
| 199 | H | 3-$CF_3$—$C_6H_4$** | 4-(4'-Cl-biphenyl) | 441 |
| 200 | H | 3-$CF_3$—$C_6H_4$** | 4-(4'-CN-biphenyl) | 432 |
| 201 | H | 3-CN—$C_6H_4$** | 4-CN—$C_6H_4$ | 313 |
| 202 | H | 3-CN—$C_6H_4$** | 4-Cl—$C_6H_4$ | 322 |
| 203 | H | 3-CN—$C_6H_4$** | 4-$CF_3$—$C_6H_4$ | 356 |
| 204 | H | 3-CN—$C_6H_4$** | 4-(4'-Cl-biphenyl) | 398 |
| 205 | H | 3-CN—$C_6H_4$** | 4-(4'-CN-biphenyl) | 387 |
| 206 | H | 3-CN—$C_6H_4$** | 4-F—$C_6H_4$ | 306 |
| 207 | H | 4-CN—$C_6H_4$** | 4-$CF_3$—$C_6H_4$ | 356 |
| 208 | H | 4-CN—$C_6H_4$** | 3-$CF_3$—$C_6H_4$ | 356 |
| 209 | H | 4-CN—$C_6H_4$** | 4-(4'-$CF_3$-biphenyl) | *** |
| 210 | H | 4-CN—$C_6H_4$** | 4-F—$C_6H_4$ | 306 |
| 211 | H | 4-Cl—$C_6H_4$** | 4-$CF_3$—$C_6H_4$ | 365 |
| 212 | H | 4-Cl—$C_6H_4$** | 2-$CF_3$—$C_6H_4$ | 365 |
| 213 | H | 4-Cl—$C_6H_4$** | 4-(4'-$CF_3$-biphenyl) | 441 |
| 214 | H | 4-Cl—$C_6H_4$** | 4-F—$C_6H_4$ | 315 |
| 215 | H | 4-(4'-Cl-biphenyl)** | 4-$CF_3$—$C_6H_4$ | 441 |
| 216 | H | 4-(4'-Cl-biphenyl)** | 4-CN—$C_6H_4$ | 398 |
| 217 | H | 4-(4'-Cl-biphenyl)** | 4-Cl—$C_6H_4$ | 409 |
| 218 | H | 4-(4'-CN-biphenyl)** | 4-$CF_3$—$C_6H_4$ | 389 |
| 219 | H | 4-(4'-CN-biphenyl)** | 4-CN—$C_6H_4$ | 432 |
| 220 | H | 4-(4'-CN-biphenyl)** | 4-Cl—$C_6H_4$ | 398 |
| 221 | H | 4-Cl—$C_6H_4$** | 3,4-diCl—$C_6H_3$ | *** |
| 222 | H | 4-Cl—$C_6H_4$** | 2,4-diCl—$C_6H_3$ | *** |
| 223 | H | 4-Cl—$C_6H_4$** | 3-F-4-$CF_3$—$C_6H_3$ | *** |
| 224 | H | 4-CN—$C_6H_4$** | 3,4-diCl—$C_6H_3$ | *** |
| 225 | H | 4-CN—$C_6H_4$** | 2,4-diCl—$C_6H_3$ | *** |
| 226 | H | 4-CN—$C_6H_4$** | 3-F-4-$CF_3$—$C_6H_3$ | *** |
| 227 | H | 4-F—$C_6H_4$** | 4-$OCF_3$—$C_6H_4$ | *** |
| 228 | H | 4-CN—$C_6H_4$** | 4-$OCF_3$—$C_6H_4$ | *** |
| 229 | H | 4-CN—$C_6H_4$** | 4-$OCHF_2$—$C_6H_4$ | *** |
| 230 | H | 4-CN—$C_6H_4$** | 4-$OCF_2CHF_2$—$C_6H_4$ | *** |

TABLE III-continued

| Ex. No. | R | R₁ | R₂ | Mass Ion |
|---|---|---|---|---|
| 231 | H | 4-CN—$C_6H_4$** | 5-chlorothiophen-2-yl | *** |
| 232 | H | 4-CN—$C_6H_4$** | 2,2difluoro-1,3-dioxol-$C_6H_3$-5-yl | *** |
| 233 | H | 4-OCF₃—$C_6H_4$** | 3,5-diCl—$C_6H_3$ | 417 |
| 234 | H | 4-OCF₃—$C_6H_4$** | 3,4-dif—$C_6H_3$ | 384 |
| 235 | H | 4-OCF₃—$C_6H_4$** | 4-n-propoxy-$C_6H_4$ | 406 |
| 236 | H | 4-OCF₃—$C_6H_4$** | 3,4-diCl—$C_6H_3$ | 417 |
| 237 | H | 4-OCF₃—$C_6H_4$** | 3-F-4-CF₃—$C_6H_3$ | 434 |
| 238 | H | 4-OCF₃—$C_6H_4$** | 5-chlorothiophen-2-yl | 389 |
| 239 | H | 4-OCF₃—$C_6H_4$** | thiophen-2-yl | 354 |
| 240 | H | 4-OCF₃—$C_6H_4$** | 4-phenoxy-$C_6H_4$ | 440 |
| 241 | H | 4-OCF₃—$C_6H_4$** | pyridine-3-yl | 349 |
| 242 | H | 4-OCF₃—$C_6H_4$** | 4-OCF₃—$C_6H_4$ | 432 |
| 243 | H | 4-OCF₃—$C_6H_4$** | 4-F—$C_6H_4$ | 366 |
| 244 | H | 4-OCF₃—$C_6H_4$** | 4-CN—$C_6H_4$ | 373 |
| 245 | H | 4-OCF₃—$C_6H_4$** | 4-Cl—$C_6H_4$ | 383 |
| 246 | H | 4-OCF₃—$C_6H_4$** | 4-OCHF₂—$C_6H_4$ | 414 |
| 247 | H | 4-OCF₃—$C_6H_4$** | 2-F-5-CF₃—$C_6H_3$ | 434 |
| 248 | H | 4-OCF₃—$C_6H_4$** | 4-CF₃—$C_6H_4$ | 416 |
| 249 | H | 4-OCF₃—$C_6H_4$** | 3-F-5-CF₃—$C_6H_3$ | 434 |
| 250 | H | 4-OCF₃—$C_6H_4$** | 2-F-4-CF₃—$C_6H_3$ | 434 |
| 251 | H | 4-OCF₃—$C_6H_4$** | 4-OCF₂CHF₂—$C_6H_4$ | 464 |
| 252 | H | 4-OCF₃—$C_6H_4$** | 2,2difluoro-1,3-dioxol-$C_6H_3$-5-yl | 428 |
| 253 | H | 4-OCF₃—$C_6H_4$** | pyridine-4-yl | 349 |
| 254 | H | 4-OCF₃—$C_6H_4$** | pyridine-2-yl | 349 |
| 255 | H | 4-OCF₃—$C_6H_4$** | 3-Br-pyridine-2-yl | 428 |
| 256 | H | 4-OCF₃—$C_6H_4$** | 4-(4-F-phenyl)-pyridin-3-yl | 442 |
| 257 | H | 4-OCF₃—$C_6H_4$** | 4-(thiophen-2-yl)-pyridin-3-yl | 431 |
| 258 | H | 4-OCF₃—$C_6H_4$** | 4-(4-OCF₃-phenyl)-pyridin-3-yl | 509 |
| 259 | H | 4-OCF₃—$C_6H_4$** | 4-(5-Cl-thiophen-2-yl)-pyridin-3-yl | 465 |
| 260 | H | 4-OCF₃—$C_6H_4$** | 4-(4-Cl-phenyl)-pyridin-3-yl | 460 |
| 261 | H | 4-OCF₃—$C_6H_4$** | 4-(3-Cl-phenyl)-pyridin-3-yl | 460 |
| 262 | H | 4-OCF₃—$C_6H_4$** | 4-Br-pyridine-3-yl | 428 |
| 263 | H | 4-OCF₃—$C_6H_4$** | 3-Cl-pyridine-4-yl | 384 |
| 264 | H | 4-OCF₃—$C_6H_4$** | 4-cyclopropylmethoxy-$C_6H_4$ | 418 |
| 265 | H | 4-OCF₃—$C_6H_4$** | 4-(5-Cl-thiophen-2-yl)-$C_6H_4$ | 464 |
| 266 | H | 4-OCF₃—$C_6H_4$** | 2-methyl-1H-imidazol-4-yl | 352 |
| 267 | H | 4-OCF₃—$C_6H_4$** | 5-chloro-1,3-dimethyl-1H-pyrazol-4-yl | 401 |
| 268 | H | 4-OCF₃—$C_6H_4$** | 5-methyl-1-o-tolyl-1H-pyrazol-4-yl | 442 |
| 269 | H | 4-OCF₃—$C_6H_4$** | 2-phenyl-1H-imidazol-4-yl | 414 |
| 270 | H | 4-OCF₃—$C_6H_4$** | 2-Cl-pyridine-3-yl | 384 |
| 271 | H | 4-OCF₃—$C_6H_4$** | 4-chloro-1-methyl-1H-pyrazol-3-yl | 387 |
| 272 | H | 4-OCF₃—$C_6H_4$** | 5-(4-F-3-CF₃-phenyl)-furan-2-yl | 500 |
| 273 | H | 4-OCF₃—$C_6H_4$** | 5-chloro-1-methyl-3-trifluoromethyl-1H-imidazol-3-yl | 455 |
| 274 | H | 4-OCF₃—$C_6H_4$** | 5-bromo-1-methyl-1H-imidazol-3-yl | 431 |
| 275 | H | 4-OCF₃—$C_6H_4$** | 1-(4-methoxyphenyl)-5-methyl-1H-pyrazol-4-yl | 458 |
| 276 | H | 4-OCF₃—$C_6H_4$** | 1-(4-fluorophenyl)-5-methyl-1H-pyrazol-4-yl | 446 |
| 277 | H | 4-OCF₃—$C_6H_4$** | 1-(phenyl)-5-methyl-1H-pyrazol-4-yl | 428 |
| 278 | H | 4-OCF₃—$C_6H_4$** | 2-methanesulfanyl-nicotinonitrile | 406 |
| 279 | H | 4-OCF₃—$C_6H_4$** | 5-bromo-furan-2-yl | 417 |
| 280 | H | 4-OCF₃—$C_6H_4$** | 6-phenoxy-pyridin-3-yl | 441 |
| 281 | H | 4-OCF₃—$C_6H_4$** | 4-(1,2,4-triazol-1-yl)-$C_6H_4$ | 415 |

TABLE III-continued

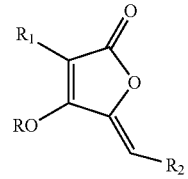

| Ex. No. | R | $R_1$ | $R_2$ | Mass Ion |
|---|---|---|---|---|
| 282 | H | 4-OCF$_3$—C$_6$H$_4$** | 5-(pyridine-2-yl)-thiphen-2-yl | 431 |
| 283 | H | 4-OCF$_3$—C$_6$H$_4$** | 5-(6-morpholino-4-yl)-pyridin-3-yl | 434 |
| 284 | H | 4-OCF$_3$—C$_6$H$_4$** | 4-(4-methyl-piperazin-1-yl)-C$_6$H$_4$ | 446 |
| 285 | H | 4-OCF$_3$—C$_6$H$_4$** | 4-(thiophen-2-yl)-C$_6$H$_4$ | 430 |
| 286 | H | 4-OCF$_3$—C$_6$H$_4$** | 4-(pyrrol-1-yl)-C$_6$H$_4$ | 413 |
| 287 | H | 4-OCF$_3$—C$_6$H$_4$** | 4-(4'-Cl-biphenyl) | 459 |
| 288 | H | 4-OCF$_3$—C$_6$H$_4$** | 4-(4'-CN-biphenyl) | 449 |
| 289 | H | 4-OCF$_3$—C$_6$H$_4$** | 2,5-dimethyl-2H-pyrazol-3-yl | 366 |
| 290 | H | thiophen-2-yl | 4-CN—C$_6$H$_4$ | 295 |
| 291 | H | thiophen-2-yl | 4-Cl—C$_6$H$_4$ | 305 |
| 292 | H | thiophen-2-yl | 4-CF$_3$—C$_6$H$_4$ | 338 |
| 293 | H | 5-chlorothiophen-2-yl | 4-Cl—C$_6$H$_4$ | 339 |
| 294 | H | 5-chlorothiophen-2-yl | 4-CN—C$_6$H$_4$ | 330 |
| 295 | H | 5-chlorothiophen-2-yl | 4-CF$_3$—C$_6$H$_4$ | 373 |
| 296 | H | 5-chlorothiophen-2-yl | 4-OCF$_3$—C$_6$H$_4$ | 389 |
| 297 | H | 5-chlorothiophen-2-yl | 4-OCHF$_2$—C$_6$H$_4$ | 371 |
| 298 | H | 5-chlorothiophen-2-yl | 3,4-diCl—C$_6$H$_3$ | 374 |
| 299 | H | 5-chlorothiophen-2-yl | 3,4-diF—C$_6$H$_3$ | 341 |
| 300 | H | 5-chlorothiophen-2-yl | 4-F-3-CF$_3$—C$_6$H$_3$ | 391 |
| 301 | H | 5-chlorothiophen-2-yl | 4-F—C$_6$H$_4$ | 323 |
| 302 | H | 5-chlorothiophen-2-yl | 3-F-4-CF$_3$—C$_6$H$_3$ | 391 |
| 303 | H | 5-chlorothiophen-2-yl | 4-(4'-Cl-biphenyl) | 415 |
| 304 | H | 5-chlorothiophen-2-yl | 4-cyclopropylmethoxy-C$_6$H$_4$ | 375 |
| 305 | H | 5-chlorothiophen-2-yl | 4-OCF$_2$CHF$_2$—C$_6$H$_4$ | 421 |
| 306 | H | 5-chlorothiophen-2-yl | 5-chlorothiophen-2-yl | 345 |
| 307 | H | 5-chlorothiophen-2-yl | 4-Br-pyridine-3-yl | 385 |
| 308 | H | 5-chlorothiophen-2-yl | 2,2difluoro-1,3-dioxol-C$_6$H$_3$-5-yl | 385 |
| 309 | H | 5-chlorothiophen-2-yl | 4-(4-Cl-phenyl)-pyridin-3-yl | 416 |
| 310 | H | 5-chlorothiophen-2-yl | 4-(4-F-phenyl)-pyridin-3-yl | 400 |
| 311 | H | 5-chlorothiophen-2-yl | 4-(4-OCF$_3$-phenyl)-pyridin-3-yl | 466 |
| 312 | H | 5-chlorothiophen-2-yl | 4-(5-Cl-thiophen-2-yl)-pyridin-3-yl | 422 |
| 313 | H | 5-chlorothiophen-2-yl | 4-(5-Cl-thiophen-2-yl)-C$_6$H$_4$ | 421 |
| 314 | H | 4-Cl—C$_6$H$_4$** | 4-cyclopropylmethoxy-C$_6$H$_4$ | *** |
| 315 | H | 4-Cl—C$_6$H$_4$** | 4-SCF$_3$—C$_6$H$_4$ | *** |
| 316 | H | 4-Cl—C$_6$H$_4$** | 2-methanesulfanyl-nicotinonitrile | *** |
| 317 | H | 4-Cl—C$_6$H$_4$** | 5-(4-F-3-CF$_3$-phenyl)-furan-2-yl | *** |
| 318 | H | 4-Cl—C$_6$H$_4$** | 6-phenoxy-pyridin-3-yl | *** |
| 319 | H | 4-Cl—C$_6$H$_4$** | 1-(4-fluorophenyl)-5-methyl-1H-pyrazol-4-yl | *** |
| 320 | H | 4-CN—C$_6$H$_4$** | 6-phenoxy-pyridin-3-yl | *** |
| 321 | H | 4-CN—C$_6$H$_4$** | 1-(4-fluorophenyl)-5-methyl-1H-pyrazol-4-yl | *** |
| 322 | H | 4-CN—C$_6$H$_4$** | 2-methanesulfanyl-nicotinonitrile | *** |

*E isomer
**Mixture of Z and E isomers
***NMR analysis only

EXAMPLE 323

Evaluation of the Inhibitory Activity of Test Compounds Against Enzymes which Catalyze Bacterial Cell Wall Biosynthesis S. aureus and E. coli UDP-N-acetylglucosamine enolpyruvoyl transferase, MurA Preparation of Enzyme Solution:

The enzyme solution is prepared by admixing the following: 50 mM Tris/HCl pH 8.0, 500 ml 1 M Tris, 5 mM DTT, 50 ml 1 M DTT, 20% Glycerol 4 ml 50% Glycerol, add water to 10 ml.

Preparation of Stop Solution:

The stop solution is prepared by mixing the following: 4.2% ammonium molybdate in 4N HCl, 8.4 g/200 ml 4N HCl, 0.045% malachite green, 90 mg/200 ml water, then stir 1 part ammonium molybdate with 2 parts malachite green for 30 min.

A procedure similar to that described by C. T. Walsh in Biochemistry 33, 10646-10651, is used to evaluate the inhibitory activity of test compounds against MurA, the enzyme which catalyzes the first step of bacterial cell wall biosynthesis. Experiments are performed by adding a solution of test compound (in a mixture of dimethylsulfoxide and water) and an enzyme solution to a well. After a pre-incubation period of 10 mintues at 37° C., Tris/BME buffer and assay buffer are added. A start point optical density ($OD_0$) reading is taken at 340 nm immediately following the addition of assay buffer. After incubation for 1 hr at 37° C., the stop solution is added and the color is allowed to develop for 30 minutes. An end point $OD_1$ reading at 660 nM is then taken. The % inhibition at a concentration of 25 µg/ml is calculated for each test compound using the formula:

$$\% \text{ inhibition} = 100 - \frac{OD_1 - OD_0 \text{ for test compound}}{OD_1 - OD_0 \text{ mean of control}} \times 100$$

Using these values, the concentration required to give 50% inhibition ($IC_{50}$) for each test compound is determined by linear regression analysis. The results are shown in Table III.

S. aureus and E. coli Enopyruvyl-UPD-N-acetylglucosamine reductase, Mur B

Preparation of Tris/BME buffer:

Dilute 17.5 uL of aqueous 5 mM BME (2-mercaptoethanol) to 50 mL with 50 mM Tris/HCl (pH 8.0).

Preparation of Enzyme Solution:

Dilute aqueous MurB stock solution (0.94 mg/mL) with 200 parts 50 mM Tris/2-BME buffer. The final MurB concentration is 4.7 µg/mL.

Synthesis of Substrate for MurB (MurA Product EP-UDP-GluNAc):

A mixture of 13 mg UDP-N-acetylglucosamine and 5.5 mg phosphoenolpyruvate are dissolved in 10 mL Tris/BME buffer forming 2 mM concentrations of each reagent in solution. The solution is incubated with 300 µg purified MurA at 37° C. overnight to give approximately 70-80% product yield.

Preparation of Assay Buffer:

The assay buffer is prepared in water from reagents with the following final concentrations: 100 mM Tris/HCl (pH 8.0), 200 µM NADPH, 100 µM MurB substrate, 10 µM 2-mercaptoethanol, and 10 µM KCl.

A procedure similar to that described by Dhalla et al., in Biochemistry 1995, 34, 5390, is used to evaluate the inhibitory activity of test compounds against MurB, the enzyme which catalyzes the second step of bacterial cell wall biosynthesis. Experiments are performed by adding 20 µL of a solution of test compound in a mixture of dimethylsulfoxide and water and 30 µL of enzyme solution to a well. After a pre-incubation period of 20 mins. at 23° C., 50 µL of Tris/BME buffer and 100 µL of assay buffer are added. A start point optical density ($OD_0$) reading is taken at 340 µM immediately following the addition of assay buffer using a Molecular Devices Spectra Max 250 with SoftMax software. After a 20 min. incubation period at 23° C., an endpoint $OD_1$ reading is taken at 340 µM. Controls are performed using the same procedure and employing 20 µL of a blank dimethylsulfonide and solvent mixture in place of the test compound solution. The % inhibition at concentrations of 10 µg/ml and 25 µg/ml are calculated using the formula:

$$\% \text{ inhibition} = 100 - \frac{\text{Sample } OD_1 - \text{Sample } OD_0}{\text{Control } OD_1 - \text{Control } OD_0} \times 100$$

Using these values, the $IC_{50}$ for each test compound is determined by linear regression analysis. The results are shown in Table III.

S. aureus and E. coli Uridine-diphosphate-N-acetvimuramoyl: L-alanine lipase, MurC Preparation of Buffer:

The buffer is prepared from aqueous reagents with the following final concentrations: 83 mM Tris/HCl (pH 8.0), 50 mM $MgC_{12}$, and 2 mM ATP.

Preparation of Enzyme Solution:

A 1 mg/mL stock solution of MurC is prepared in a buffer consisting of 20 mM Tris/HCl (pH 8.5) with 2.5 µM BME. The stock solution is further diluted with the buffer to give a final enzyme concentration of 100 µg/mL for the E. coli stock solution and 70 µg/mL for the S. aureus stock solution.

Preparation of Test Compound Solutions:

All test solutions are prepared in DMSO as 10 mg/mL, then diluted with 50 mM Tris/HCl (pH 8.5) to 100 µg/mL.

Preparation of Stop Solution:

The stop solution is prepared by stirring 1 part 4.2% ammonium molybdate in 4N HCl with 2 parts 0.045% malachite green for 30 min.

In this evaluation, the inhibitory activity of a test compound against MurC, the enzyme which catalyzes the third step of bacterial cell wall bioxynthesis is determined. Experiments are performed by adding 2.5 µl buffer, 2.5 µl 0.5M $NH_4SO_2$, 5 µl 2 µM L-Ala, 5 µl enzyme solution and 6.5 µl test compound solution to each well in a 96-well microplate. After a pre-incubation period of 10 mins. at 23° C., 3.75 µl of a 0.75 µM solution of UDP-MurNac is added to each well. Following an incubation period of 10 mins. at 37° C., 210 µl stop solution and 50 µl of a 34% w/v sodium citrate solution are added and color is allowed to develop for 10 mins. at 23° C. (Lanzetta et al., Analytical Biochemistry, 1979, 95) Optical density readings are taken at 660 nm using a Molecular Devices Spectra Max 250 with Soft Max software. Controls are performed using the same procedure and omitting the addition of UDP-MurNac. The % inhibition of a concentration of 25 µg/ml is calculated for each test compound using the formula:

$$\% \text{ inhibition} = 100 - \frac{\text{Sample } OD}{\text{mean Control } OD} \times 100$$

Using these values the $IC_{50}$ is determined by linear regression analysis. The results are shown in Table III.

*S. aureus* and *E. coli* Uridine-diphosphate-N-acetylmuramoyl-L-alanine: D-glutamate liease, MurD Preparation of Buffer:
The buffer is prepared from aqueous reagents with the following final concentrations: 83 mM Tris/HCl (pH 8.0), 50 mM $MgCl_2$, and 2 mM ATP.

Preparation of Enzyme Solution:
A 1 mg/mL stock solution of MurD is prepared in a buffer consisting of 20 mM Tris/HCl (pH 8.5) with 2.5 µM BME. The stock solution is further diluted with the buffer to give a final enzyme concentration of 22 µg/mL for the *E. coli* stock solution and 11.1 µg/mL for the *S. aureus* stock solution.

Preparation of Test Compound Solutions:
All test solutions are prepared in DMSO as 10 mg/mL, then diluted with 50 mM Tris/HCl (pH 8.5) to 100 µg/mL.

Preparation of Stop Solution:
The stop solution is prepared by stirring 1 part 4.2% ammonium molydbate in 4N HCl with 2 parts 0.045% malachite green for 30 min.

In this evaluation, the inhibitory activity of a test compound against MurD, the enzyme which catalyzes the fourth step of bacterial cell wall biosynthesis is determined. Using essentially the same procedure described hereinabove for evaluating MurC and employing MurD as the enyzme, the % inhibition at 25 µg/ml and the $IC_{50}$ for each test compound is determined. The results are shown in Table IV, wherein (E) designates *E. coli* and (S) designates *S. aureus*.

TABLE IV

| Ex. No. | MurA $IC_{50}$ (µg/mL) | MurB $IC_{50}$ (µg/mL) | MurC $IC_{50}$ (µg/mL) | MurD $IC_{50}$ (µg/mL) |
|---|---|---|---|---|
| 4 | >25 (E) | 10 (E); 10 (S) | 7 (E); 16 (S) | >25 (E); 24 (S) |
| 5 | >25 (E) | 8 (E); 6 (S) | 6 (E) | >25 (E) |
| 6 | >25 (E) | >25 (E); 21 (S) | 16 (E) | >25 (E) |
| 7 | >25 (E) | 21 (E) | 13 (E) | >25 (E) |
| 8 | >25 (E) | 11 (E) | 6 (E) | >25 (E) |
| 9 | >25 (E) | 16 (E) | >25 (E) | >25 (E) |
| 10 | 1 (E) | 6 (E) | 4 (E); 7 (S) | 21 (E); 13 (S) |
| 11 | 1 (E) | 6 (E) | 4 (E); 5 (S) | 21 (E); 11 (S |
| 12 | >25 (E) | >25 (E) | 15 (E) | >25 (E) |
| 13 | 0.5 (E) | 12 (E) | 4 (E); 15 (S) | >25 (E); 20 (S) |
| 14 | 5 (E) | >25 (E) | 13 (E); 22 (S) | >25 (E); >25 (S) |
| 15 | >25 (E) | >25 (E) | 17 (E); >25 (S) | >25 (E); >25 (S) |
| 16 | >25 (E) | >25 (E) | 7 (E); 22 (S) | >25 (E); >25 (S) |
| 17 | >25 (E) | >24 (E) | 10(E); >25(S) | >25 (E); >25 (S) |
| 18 | 6 (S) | 6 (E); 5 (S) | 10 (S) | 18 (S) |
| 19 | 17 (S) | 20 (E); 10 (S) | 6 (E); 19 (S) | >25 (E); 17 (S) |
| 20 | >25 (S) | 3 (E); 3 (S) | 11 (E); 15 (S) | >25 (E); 19 (S) |
| 21 | 5 (S) | 5 (E); 3 (S) | 20 (S) | 8 (S) |
| 22 | 9 (S) | 6 (E); 6 (S) | 12 (S) | 17 (S) |
| 23 | 14 (S) | 4 (E); 5 (S) | 12 (S) | 10 (S) |
| 24 | 7 (S) | 4 (E); 2 (S) | 12 (S) | 11 (S) |
| 25 | 5 (S) | 2 (E); 2 (S) | 12 (S) | 14 (S) |
| 26 | 4 (S) | 3 (E); 2 (S) | 6 (S) | 9 (S) |
| 27 | 2 (S) | 3 (E); 2 (S) | >25 (S) | 24 (S) |
| 28 | 10 (S) | 3 (E); 3 (S) | >25 (S) | >25 (S) |
| 29 | 2 (S) | 2 (E); 2 (S) | 24 (S) | 17 (S) |
| 30 | 3 (S) | 2 (E); 2 (S) | >25 (S) | >25 (S) |
| 31 | 2 (S) | 2 (E); 2 (S) | >25 (S) | 10 (S) |
| 32 | 10 (S) | 6 (E); 3 (S) | 12 (S) | 9 (S) |
| 33 | 4 (S) | 2 (E); 2 (S) | >25 (S) | >25 (S) |
| 34 | 22 (S) | 6 (S) | 21 (S) | >25 (S) |
| 35 | >25 (S) | 6 (S) | 8 (S) | 17 (S) |
| 36 | 6 (S) | 3 (S) | 5 (S) | 9 (S) |
| 37 | >25 (S) | 10 (S) | 10 (S) | 19 (S) |
| 38 | >25 (S) | 8 (S) | 7 (S) | 6 (S) |
| 39 | 15 (S) | 8 (E); 4 (S) | 8 (S) | 15 (S) |
| 40 | 14 (S) | — | 4 (S) | 7 (S) |
| 41 | >25 (E) | >25 (E) | 13 (E) | >25 (E) |
| 42 | 20 (E) | 10 (E) | 6 (E); 18 (S) | >25 (E); >25 (S) |
| 43 | 20 (E) | 6 (E); 5 (S) | 4 (E); 21 (S) | >25 (E); >25 (S) |
| 44 | 18 (E) | 7 (E) | 6 (E) | >25 (E) |
| 45 | >25 (E) | 2 (E) | 10 (E) | >25 (E); >25 (S) |
| 46 | >25 (E) | >25 (E) | 16 (E) | >25 (E) |
| 47 | >25 (E) | 23 (E); 10 (S) | 11 (E) | >25 (E); >25 (S) |
| 48 | >25 (E) | >25(E) | 13 (E) | >25 (E) |
| 49 | 17 (E) | 11 (E) | 9 (E) | >25 (E) |
| 50 | 16 (E) | >25 (E) | 9 (E) | >25 (E) |
| 51 | >25 (E) | >25 (E) | 9 (E); 20 (S) | >25 (E); >25 (S) |
| 52 | >25 (E) | >25 (E) | 17(E); >25(S) | 23 (E); 20 (S) |
| 53 | >25 (E) | 6 (E) | 5 (E); 7 (S) | 5 (E); 16 (S) |
| 54 | >25 (E) | 8 (E) | 5 (E); 11 (S) | >25 (E); >25 (S) |
| 55 | >25 (E) | 4 (E) | 11 (E); 22 (S) | 24 (E); 15 (S) |
| 56 | >25 (E) | >25 (E) | 5 (E); 11 (S) | >25 (E); 19 (S) |
| 57 | >25 (E) | 6 (E) | 20 (E) | 17 (E); 19 (S) |
| 58 | >25 (E) | >25 (E) | 14 (E) | >25 (E); >25 (S) |
| 59 | 17 (E) | 6 (E) | 6 (E) | 5 (E); 5 (S) |
| 60 | >25 (E) | >25 (E) | 14 (E) | >25 (E); 22 (S) |
| 61 | >25 (E) | >25 (E) | 14 (E) | >25 (E); 19 (S) |
| 62 | 7 (E) | 15 (E) | 5 (E) | 5 (E); >25 (S) |
| 63 | 1 (E) | 3 (E) | 17 (E); 23 (S) | 6 (E); >25 (S) |
| 64 | 6 (E) | 3 (E) | 12 (E) | 6 (E); 8 (S) |
| 65 | >25 (E) | 10 (E) | 3 (E) | 24 (E); 15 (S) |
| 66 | 3 (E) | 2 (E) | 3 (E) | 21 (E); 5 (S) |
| 67 | 3 (E) | 1 (E) | 6 (E); 18 (S) | 9 (E); 8 (S) |
| 68 | 3 (E) | 3 (E) | 9 (E) | 11 (E); 11 (S) |
| 69 | 8 (E) | 5 (E) | 5 (S) | 19 (E); 7 (S) |
| 70 | 15 (S) | 7 (E); 5 (S) | 5 (E); 8 (S) | 17 (E); 9 (S) |
| 71 | >25 (S) | 10 (E); 10 (S) | 11 (E); 20 (S) | >25 (E); 24 (S) |
| 72 | >25 (S) | 21 (E); 20 (S) | >25(E); >25(S) | >25 (E); >25 (S) |
| 73 | >25 (S) | >25 (E); 12 (S) | 19 (E); 23 (S) | >25 (E); >25 (S) |
| 74 | >25 (S) | 22 (E); 10 (S) | 19 (E); 18 (S) | >25 (E); >25 (S) |
| 75 | >25 (S) | >25 (E); 24 (S) | 18 (E); 20 (S) | >25 (E); >25 (S) |
| 76 | 6 (S) | 7 (E); 5 (S) | 5 (E); 18 (S) | 23 (E); >25 (S) |
| 77 | >25 (S) | 21 (E); 10 (S) | 9 (E); 15 (S) | >25 (S) |
| 78 | >25 (S) | 3 (E0; 13 (S) | 21 (S) | >25 (S) |
| 79 | 14 (S) | 6 (E); 1 (S) | 24 (S) | 14 (S) |
| 80 | 15 (S) | 3 (E); 1 (S) | 18 (S) | 13 (S) |
| 81 | >25 (S) | 23 (E); 15 (S) | 16 (S) | >25 (S) |
| 99 | 4 (E) | 6 (E) | 4 (E) | >25 (E) |
| 100 | >25 (E) | 24 (E) | 13 (E); 16 (S) | >25 (E); 24 (S) |
| 101 | 23 (E) | >25 (E) | 18 (E); 23 (S) | >25 (E); >25 (S) |
| 102 | 23 (E) | 5 (E); 10 (S) | 6 (E); 19 (S) | >25 (E); 15 (S) |
| 103 | >25 (E) | 6 (E) | 16 (E) | >25 (E) |
| 104 | >25 (E) | 24 (E) | 5 (E); 19 (S) | >25 (E); >25 (S) |
| 105 | 19 (E) | 6 (E) | 5 (E); 12 (S) | 12 (E); >25 (S) |
| 106 | 9 (E) | 12 (E) | 9 (E); 12 (S) | >25 (E); 16 (S) |
| 107 | 14 (E) | 4 (E) | 6 (E) | >25 (E); 17 (S) |
| 108 | 19 (E) | 10 (E) | 6 (E) | >25 (E); 15 (S) |
| 109 | 5 (E) | 4 (E) | 10 (E) | >25 (E) |
| 110 | 7 (E) | 5 (E) | 9 (E) | 19 (E) |
| 111 | >25 (E) | 11 (E) | >25 (E) | >25 (E) |
| 112 | 15 (E) | 5 (E) | 10 (E) | >25 (E) |
| 113 | 4 (E) | 3 (E) | >25 (E) | >25 (E) |
| 114 | 1 (E) | 1 (E) | 10 (E) | 16 (E) |
| 115 | 5 (E) | 5 (E) | >25 (E) | >25 (E) |
| 116 | 3 (E) | 4 (E) | >25 (E) | >25 (E) |
| 117 | 10 (E) | 7 (E) | >25 (E) | >25 (E) |
| 118 | 15 (E) | 18 (E) | 19 (E) | >25 (E) |
| 119 | 1 (E) | 1 (E) | 2 (E) | 6 (E) |
| 120 | 4 (E) | 5 (E) | 23 (E) | 16 (E) |
| 121 | 9 (E) | 7 (E) | 9 (E) | 25 (E) |
| 122 | 16 (E) | 14 (E) | >25 (E) | >25 (E) |

TABLE IV-continued

| Ex. No. | MurA IC$_{50}$ (μg/mL) | MurB IC$_{50}$ (μg/mL) | MurC IC$_{50}$ (μg/mL) | MurD IC$_{50}$ (μg/mL) |
|---|---|---|---|---|
| 123 | 21 (E) | 3 (E) | >25 (E) | >25 (E) |
| 124 | 14 (E) | 12 (E) | >25 (E) | >25 (E) |
| 125 | 4 (E) | 5 (E) | 1 (E) | 20 (E) |
| 126 | 3 (E) | 1 (E) | 5 (E) | 9 (E) |
| 127 | 4 (E) | 6 (E) | >25 (E) | >25 (E) |
| 128 | 4 (E) | 5 (E) | 24 (E) | >25 (E) |
| 129 | 2 (E) | 2 (E) | 7 (E) | 7 (E) |
| 130 | 17 (E) | 9 (E) | 8 (E) | >25 (E) |
| 131 | 4 (E) | 2 (E) | 18 (E) | 9 (E) |
| 132 | 3 (E) | 3 (E) | 24 (E) | 8 (E) |
| 133 | 20 (E) | 12 (E) | 22 (E) | 22 (E) |
| 134 | 5 (E) | 4 (E); 2 (S) | 5 (E); 21 (S) | 6 (E); 8 (S) |
| 135 | 2 (E) | 3 (E); 3 (S) | 6 (E) | 6 (S) |
| 136 | 1 (S) | 3 (E); 2 (S) | 11 (E); >25 (S) | 6 (E); 10 (S) |
| 137 | 13 (S) | 21 (E); 3 (S) | 17 (E); 23 (S) | 18 (S) |
| 138 | 7 (S) | 22 (E); 3 (S) | 5 (E); 8 (S) | 14 (S) |
| 139 | >25 (E) | 6 (E) | 16 (E) | >25 (E) |
| 140 | 11 (S) | 4 (E); 3 (S) | 8 (S) | 20 (S) |
| 141 | 3 (S) | 2 (E); 2 (S) | >25 (S) | 3 (S) |
| 142 | >25 (S) | 10 (E); 21 (S) | >25 (S) | >25 (S) |
| 143 | >25 (S) | 7 (E); 4 (S) | 5 (S) | 10 (S) |
| 144 | >25 (S) | 20 (E); 10 (S) | 10 (S) | 20 (S) |

EXAMPLE 324

Evaluation of the Minimum Inhibitory Concentration of Test Compounds Against A Variety of Bacterial Strains In this evaluation the minimal inhibitory concentration (MIC) of test compounds against Gram positive and Gram negative bacteria is performed using the microdilution broth method as recommended by the National Committee for Clinical Laboratory Standards (Approved Standards M7-A5 2000). Mueller-Hinton broth is used for the enterobacteriaceae, staphylococci and enterococci. Streptococci are also tested in Mueller-Hinton broth supplemented with 5% horse blood (LHB). Test organisms include recent clinical isolates that are resistant to methicillin, penicillin and/or vancomycin. Microtiter plates containing 50 μl per well of two-fold serial dilutions of the test compounds in the appropriate broth are inoculated with 50 μl of inoculum to a final concentration of 1-5×10$^5$ CFU/ml. The MIC is determined after incubation for 18-22 hours at 35° C. in ambient air. The results are shown in Table V.

TABLE V

| | MIC (μg/mL) | | | | |
|---|---|---|---|---|---|
| Ex. No. | S. aureus GC 1131 | S. aureus GC 4543 | E. faecalis GC 4555 | E. faecalis GC 2242 | S. pneumo GC 1894 |
| 4 | 16 | 16 | 32 | 8 | 1 |
| 5 | 8 | 8 | 16 | 8 | 0.5 |
| 6 | 32 | 64 | >128 | 32 | 8 |
| 7 | 32 | 64 | 64 | 32 | 2 |
| 8 | 8 | 8 | 16 | 4 | 0.25 |
| 9 | 32 | >128 | 64 | 8 | <0.125 |
| 10 | 4 | 2 | 8 | 1 | <0.125 |
| 11 | 4 | 2 | 8 | 1 | <0.125 |
| 12 | 64 | 64 | >128 | 64 | 2 |
| 13 | 64 | >128 | >128 | >128 | 2 |
| 14 | >128 | >128 | 4 | 64 | 64 |
| 15 | 64 | 64 | 64 | 32 | 0.5 |
| 16 | 64 | >128 | 64 | 64 | 0.5 |
| 17 | 32 | >128 | 64 | 32 | <0.125 |
| 18 | 4 | 4 | 16 | 8 | 0.5 |
| 19 | 2 | 2 | 8 | 8 | 0.5 |
| 20 | 4 | 4 | 16 | 16 | 0.5 |
| 21 | 1 | 0.5 | 4 | 2 | 0.5 |
| 22 | 4 | 4 | 16 | 8 | 1 |
| 23 | 8 | 4 | 8 | 8 | 1 |
| 24 | 2 | 1 | 4 | 4 | 0.5 |
| 25 | 1 | 0.5 | 4 | 2 | 0.25 |
| 26 | 2 | 1 | 4 | 2 | <0.125 |
| 27 | 0.5 | 0.5 | 2 | 1 | 0.5 |
| 28 | 1 | 0.5 | 4 | 2 | <0.125 |
| 29 | 0.5 | 0.5 | 2 | 0.5 | <0.125 |
| 30 | 2 | 1 | 4 | 4 | 0.25 |
| 31 | 0.5 | 0.25 | 2 | 1 | 0.25 |
| 32 | 2 | 2 | 8 | 4 | 0.5 |
| 33 | 0.5 | 0.5 | 2 | 1 | 0.5 |
| 34 | 32 | 32 | 64 | 64 | 4 |
| 35 | 8 | 8 | 16 | 8 | 2 |
| 36 | 4 | 4 | 8 | 4 | 1 |
| 37 | 16 | 16 | 32 | 16 | 8 |
| 38 | 8 | 8 | 32 | 16 | 1 |
| 39 | 2 | 4 | 8 | 4 | 1 |
| 40 | 1 | 1 | 2 | 2 | <0.125 |
| 41 | 32 | 64 | 64 | 32 | 32 |
| 42 | 8 | 8 | 32 | 8 | 8 |
| 43 | 8 | 8 | 16 | 4 | 1 |
| 44 | 4 | 8 | 16 | 8 | 1 |
| 45 | 16 | 4 | 8 | 4 | 2 |
| 46 | 64 | 32 | 32 | 64 | 16 |
| 47 | 16 | 32 | 64 | 32 | 16 |
| 48 | 32 | 64 | >128 | 32 | 8 |
| 49 | 8 | 8 | 32 | 8 | 0.5 |
| 50 | 8 | 4 | 32 | 8 | 4 |
| 51 | >128 | 16 | 32 | 8 | <0.125 |
| 52 | 16 | 16 | 8 | 4 | 0.5 |
| 53 | 16 | 16 | 8 | 4 | 0.5 |
| 54 | 8 | 16 | 32 | 4 | <0.125 |
| 55 | 4 | 1 | 4 | 1 | <0.125 |
| 56 | 16 | 32 | 32 | 8 | 4 |
| 57 | 32 | 4 | 8 | 2 | <0.125 |
| 58 | 8 | 16 | >128 | 16 | <0.125 |
| 59 | >128 | >128 | 8 | 8 | 32 |
| 60 | 16 | 16 | 32 | 8 | 8 |
| 61 | 16 | 16 | 32 | 16 | 8 |
| 62 | >128 | >128 | 64 | 32 | 64 |
| 63 | 4 | 0.5 | 1 | 0.5 | <0.125 |
| 64 | 16 | 8 | 8 | 2 | <0.125 |
| 65 | 8 | 8 | 16 | 4 | <0.125 |
| 66 | 2 | 1 | 2 | 0.5 | <0.125 |
| 67 | 1 | 0.5 | 2 | 0.5 | <0.125 |
| 68 | 2 | 2 | 2 | 1 | <0.125 |
| 69 | 2 | 1 | 0.5 | 0.5 | 0.25 |
| 70 | 2 | 1 | 2 | 2 | 0.5 |
| 71 | 8 | 8 | 8 | 4 | 0.5 |
| 72 | >128 | >128 | >128 | >128 | 32 |
| 73 | >128 | >128 | >128 | >128 | 64 |
| 74 | 64 | >128 | >128 | >128 | 32 |
| 75 | 64 | >128 | 64 | >128 | 32 |
| 76 | >128 | >128 | >128 | >128 | 64 |
| 77 | >128 | 64 | >128 | >128 | 64 |
| 78 | 32 | 32 | 64 | 64 | 2 |
| 79 | 2 | 1 | 8 | 4 | 0.5 |
| 80 | 2 | 1 | 8 | 4 | 1 |
| 81 | 8 | 8 | 32 | 16 | 1 |
| 99 | 4 | 2 | 16 | 4 | 0.25 |
| 100 | >128 | >128 | >128 | >128 | 64 |
| 101 | >128 | >128 | >128 | 64 | 64 |
| 102 | 8 | 4 | 16 | 4 | 1 |
| 103 | >128 | 64 | 64 | 32 | 0.5 |
| 104 | 16 | 32 | 64 | 32 | 0.5 |
| 105 | 8 | 8 | 8 | 2 | <0.125 |
| 106 | 2 | 2 | 1 | 0.25 | 0.25 |
| 107 | 4 | 2 | 8 | 2 | 0.25 |
| 108 | 2 | 2 | 8 | 2 | 1 |
| 109 | 2 | 2 | 4 | 1 | 0.25 |
| 110 | 2 | 2 | 4 | 1 | 0.25 |
| 111 | 32 | 16 | 16 | 1 | 0.25 |

TABLE V-continued

| | MIC (μg/mL) | | | | |
|---|---|---|---|---|---|
| Ex. No. | S. aureus GC 1131 | S. aureus GC 4543 | E. faecalis GC 4555 | E. faecalis GC 2242 | S. pneumo GC 1894 |
| 112 | 2 | 4 | 8 | 2 | 0.25 |
| 113 | 1 | 2 | 4 | 1 | 0.25 |
| 114 | 1 | 1 | 2 | 0.5 | 0.25 |
| 115 | 4 | 4 | 2 | 0.25 | 0.25 |
| 116 | 8 | 8 | 4 | 4 | <0.125 |
| 117 | 64 | 32 | 32 | 8 | 0.5 |
| 118 | 16 | 16 | 32 | 16 | 4 |
| 119 | 2 | 2 | 2 | 2 | 0.5 |
| 120 | 16 | 16 | 8 | 4 | 0.5 |
| 121 | 4 | 2 | 16 | 8 | 0.5 |
| 122 | 16 | 16 | 32 | 8 | 1 |
| 123 | 16 | 16 | 8 | 4 | 0.5 |
| 124 | 32 | 32 | 32 | 16 | 1 |
| 125 | 2 | 2 | 8 | 4 | 0.5 |
| 126 | 1 | 1 | 4 | 1 | 0.25 |
| 127 | 4 | 2 | 4 | 2 | 0.25 |
| 128 | 8 | 4 | 8 | 2 | 0.25 |
| 129 | 2 | 2 | 4 | 2 | 0.25 |
| 130 | 4 | 4 | 4 | 8 | 0.5 |
| 131 | 32 | 16 | 8 | 4 | 0.25 |
| 132 | 16 | 16 | 8 | 4 | 0.25 |
| 133 | 32 | 32 | 16 | 8 | 0.5 |
| 134 | >128 | 1 | 8 | 4 | 1 |
| 135 | 32 | 1 | 4 | 4 | 1 |
| 136 | 0.25 | 0.25 | 1 | 0.5 | 0.25 |
| 137 | 8 | 8 | 4 | 4 | 2 |
| 138 | 4 | 4 | 8 | 4 | 0.5 |
| 139 | 16 | 16 | 8 | 4 | 1 |
| 140 | 1 | 1 | 4 | 4 | 1 |
| 141 | 0.5 | 0.25 | 1 | 0.5 | <0.125 |
| 142 | 64 | >128 | >128 | >128 | 8 |
| 143 | 8 | 8 | 32 | 4 | 1 |
| 144 | 16 | 16 | >128 | 32 | 2 |

EXAMPLE 325

Comparative Evaluation of the Efficacy of a 3-Aryl-4-hydroxyfuranone Compound Against Blowfly Larvae In this evaluation, filter paper discs are treated with an acetone solution of test compound and allowed to dry. Bovine serum and newly emerged larvae of blowfly, *Lucilia sericata*, are added to the treated filter paper. Mortality is assessed at 24 h and 48 h. When more than one evaluation is performed, the data are averaged. The results, at a dose rate of 20 ppm, are shown in Table VI, wherein all test compounds are the Z isomers unless otherwise noted.

TABLE VI

| Test Compound | | | % Mortality | |
|---|---|---|---|---|
| R | R1 | R2 | 24 h | 48 h |
| H | 4-biphenyl | 1-naphthyl | 100 | 100 |
| H | 3,5-diCl—$C_6H_3$ | 4-(3-OMe-3'$CF_3$-biphenyl) | 0 | 0 |
| $CH_3$ | 3-$CF_3$—$C_6H_4$ | $C_6H_5$ | 0 | 0 |
| H | 4-CN—$C_6H_4$* | 4-(4'-CN-biphenyl) | 0 | 0 |
| H | 4-CN—$C_6H_4$** | 4-Cl—$C_6H_4$ | 25 | 100 |
| H | 4-CN—$C_6H_4$** | 4-CN—$C_6H_4$ | 40 | 100 |
| H | 4-CN—$C_6H_4$** | 4-(4'-Cl-biphenyl) | 0 | 100 |
| H | 4-Cl—$C_6H_4$ | 4-(4'-CN-biphenyl) | 0 | 0 |
| H | 4-Cl—$C_6H_4$* | 4-(4'-CN-biphenyl) | 0 | 100 |
| H | 4-Cl—$C_6H_4$** | 4-CN—$C_6H_4$ | 0 | 90 |
| H | 4-Cl—$C_6H_4$** | 3-Cl—$C_6H_4$ | 0 | 0 |
| $CH_3$ | 4-Cl—$C_6H_4$** | 4-CN—$C_6H_4$ | 0 | 0 |
| $CO_2$t-Bu | 4-Cl—$C_6H_4$** | 4-CN—$C_6H_4$ | 0 | 0 |
| $CO_2C_6H_5$ | 4-Cl—$C_6H_4$** | 4-CN—$C_6H_4$ | 0 | 0 |
| $CO_2CH_3$ | 4-Cl—$C_6H_4$** | 4-CN—$C_6H_4$ | 0 | 0 |
| $CH_2CH=CH_2$ | 4-Cl—$C_6H_4$** | 4-CN—$C_6H_4$ | 0 | 0 |
| H | 4-$CF_3$—$C_6H_4$** | 4-CN—$C_6H_4$ | 100 | 100 |
| H | 4-$CF_3$—$C_6H_4$** | 4-Cl—$C_6H_4$ | 100 | 100 |
| H | 4-$CF_3$—$C_6H_4$** | 4-$CF_3$—$C_6H_4$ | 100 | 100 |
| H | 4-$CF_3$—$C_6H_4$** | 4-(4'-Cl-biphenyl) | 0 | 65 |
| H | 4-$CF_3$—$C_6H_4$** | 4-(4'-CN-biphenyl) | 0 | 0 |
| H | 4-$CF_3$—$C_6H_4$** | 4-F—$C_6H_4$ | 100 | 100 |
| H | 4-F—$C_6H_4$** | 4-CN—$C_6H_4$ | 0 | 0 |
| H | 4-F—$C_6H_4$** | 4-Cl—$C_6H_4$ | 0 | 0 |
| H | 4-F—$C_6H_4$** | 4-$CF_3$—$C_6H_4$ | 0 | 0 |
| H | 4-F—$C_6H_4$** | 4-F—$C_6H_4$ | 0 | 0 |
| H | 4-F—$C_6H_4$** | 4-(4'-CN-biphenyl) | 0 | 0 |
| H | 4-F—$C_6H_4$** | 4-(4'-Cl-biphenyl) | 0 | 0 |
| H | 3-Cl—$C_6H_4$** | 4-CN—$C_6H_4$ | 0 | 0 |
| H | 3-Cl—$C_6H_4$** | 4-Cl—$C_6H_4$ | 0 | 0 |
| H | 3-Cl—$C_6H_4$** | 4-$CF_3$—$C_6H_4$ | 60 | 75 |
| H | 3-Cl—$C_6H_4$** | 4-(4'-Cl-biphenyl) | 0 | 0 |
| H | 3-Cl—$C_6H_4$** | 4-(4'-CN-biphenyl) | 0 | 0 |
| H | 3-Cl—$C_6H_4$** | 4-F—$C_6H_4$ | 0 | 0 |
| H | 3-$CF_3$—$C_6H_4$** | 4-CN—$C_6H_4$ | 20 | 20 |
| H | 3-$CF_3$—$C_6H_4$** | 4-F—$C_6H_4$ | 100 | 100 |
| H | 3-$CF_3$—$C_6H_4$** | 4-$CF_3$—$C_6H_4$ | 100 | 100 |
| H | 3-$CF_3$—$C_6H_4$** | 4-(4'-Cl-biphenyl) | 0 | 0 |
| H | 3-$CF_3$—$C_6H_4$** | 4-(4'-CN-biphenyl) | 0 | 0 |
| H | 3-CN—$C_6H_4$** | 4-CN—$C_6H_4$ | 0 | 0 |
| H | 3-CN—$C_6H_4$** | 4-Cl—$C_6H_4$ | 0 | 0 |
| H | 3-CN—$C_6H_4$** | 4-$CF_3$—$C_6H_4$ | 0 | 0 |
| H | 3-CN—$C_6H_4$** | 4-(4'-Cl-biphenyl) | 0 | 0 |
| H | 3-CN—$C_6H_4$** | 4-(4'-CN-biphenyl) | 20 | 20 |
| H | 3-CN—$C_6H_4$** | 4-F—$C_6H_4$ | 0 | 0 |
| H | 4-CN—$C_6H_4$** | 4-$CF_3$—$C_6H_4$ | 100 | 100 |
| H | 4-CN—$C_6H_4$** | 3-$CF_3$—$C_6H_4$ | 0 | 90 |
| H | 4-CN—$C_6H_4$** | 4-(4'-$CF_3$-biphenyl) | 0 | 25 |
| H | 4-CN—$C_6H_4$** | 4-F—$C_6H_4$ | 0 | 0 |
| H | 4-Cl—$C_6H_4$** | 4-$CF_3$—$C_6H_4$ | 100 | 100 |
| H | 4-Cl—$C_6H_4$** | 2-$CF_3$—$C_6H_4$ | 10 | 10 |
| H | 4-Cl—$C_6H_4$** | 4-(4'-$CF_3$-biphenyl) | 0 | 0 |
| H | 4-Cl—$C_6H_4$** | 4-F—$C_6H_4$ | 0 | 0 |
| H | 4-(4'-Cl-biphenyl)** | 4-$CF_3$—$C_6H_4$ | 0 | 0 |
| H | 4-(4'-Cl-biphenyl)** | 4-CN—$C_6H_4$ | 0 | 0 |
| H | 4-(4'-Cl-biphenyl)** | 4-Cl—$C_6H_4$ | 0 | 0 |
| H | $C_6H_5$ | 3-$CF_3$—$C_6H_4$ | 0 | 0 |
| H | 4-Cl—$C_6H_4$ | 4-OMe—$C_6H_4$ | 0 | 0 |
| H | 3-$CH_2$OH—$C_6H_4$ | 1-naphthyl | 0 | 0 |
| H | 3,5-diCl—$C_6H_3$ | 3-F-4-[1-(4-$CO_2C_2H_5$—piperazinyl)]-$C_6H_3$ | 0 | 0 |

TABLE VI-continued

| | Test Compound | | % Mortality | |
|---|---|---|---|---|
| R | R1 | R2 | 24 h | 48 h |
| H | 3,5-diCl—$C_6H_3$ | 3-Cl-4-{1-[4-(2-Cl—$C_{6}H_{4)}$-piperazinyl]}-$C_6H_3$ | 0 | 0 |
| H | 4-CN—$C_6H_4$ | 4-(4'-CN-biphenyl) | 0 | 0 |
| H | 3-$CH_2$OH—$C_6H_4$ | 4-(3'-$CH_2$OH-biphenyl) | 0 | 0 |
| H | 3,5-diCl—$C_6H_3$ | 4-(3',5'-diCl-biphenyl) | 0 | 0 |
| H | 4-Cl—$C_6H_4$ | 4-(4'-Cl-biphenyl) | 0 | 0 |
| H | 4-(4'-t-Bu-biphenyl) | 4-biphenyl | 0 | 0 |
| H | 4-(biphenyl) | 4-$CF_3$—$C_6H_4$ | 0 | 0 |
| H | 3-$CF_3$—$C_6H_4$ | 4-(3'-$CF_3$-biphenyl) | 0 | 0 |
| H | 3-$CF_3$—$C_6H_4$ | 4-(3-F-biphenyl) | 0 | 0 |
| H | 2-$CH_2$OH—$C_6H_4$ | 4-(2'-$CH_2$OH-biphenyl) | 0 | 0 |
| H | 3-N(COCH$_3$)$C_6H_4$ | 4-[3'-N(COCH$_3$)-biphenyl] | 0 | 0 |

*E isomer
**Mixture of Z and E isomers

EXAMPLE 326

Evaluation of the Efficacy of a 3-Aryl-4-Hydroxyfuranone Against Nematodes

In this evaluation, cultures of *C. elegans* are maintained on *E. coli* lawns on Nematode Growth Agar at 20° C. New cultures are established twice a week. Nematodes for testing are rinsed from plates using M9 Buffer. Test compounds are dissolved in DMSO to give a concentration of 10 mg/mL. One μL of this solution is added to each well of a 96 well plate. A mixture of *C. elegans* in M9 Buffer (100 μL) is added to each well, such that approximately 50 worms of mixed stages (L1, L2, L3, L4 and adults) are present in each well at a final concentration of 100 ppm, 150 ppm or 200 μM of test compound. Concentration of test compound may be varied by gradient dilution of the stock DMSO solution. Observations are made under a dissecting microscope at 4 h and 24 h postimmersion. A rating is based on the motility of the larvae and adults, using the rating system shown below. The results are shown in Table VII, wherein all test compounds are the Z isomer, unless otherwise noted.

| Rating | Description |
|---|---|
| 0 | no effect |
| 7 | reduced movement in 24 h |
| 8 | dead in 24 h |
| 9 | dead in 4 h |

TABLE VII

| | Test Compound | | | |
|---|---|---|---|---|
| R | R1 | R2 | Dose | Rating |
| H | 4-biphenyl | 4-$CF_3$—$C_6H_4$ | 150 ppm | 9 |
| H | 3-$CF_3$—$C_6H_4$ | 4-(3'-$CF_3$-biphenyl) | 150 ppm | 8 |
| H | 4-(3-F-biphenyl) | 3-$CF_3$—$C_6H_4$ | 150 ppm | 9 |
| H | 2-$CH_2$OH—$C_6H_4$ | 4-(2'-$CH_2$OH-biphenyl) | 150 ppm | 0 |
| H | 3-N(COCH$_3$)—$C_6H_4$ | 4-[3'-N(COCH$_3$)biphenyl] | 150 ppm | 0 |
| H | 4-CN—$C_6H_4$ | 4-(4'-CN-biphenyl) | 150 ppm | 8 |
| H | 3-$CH_2$OH—$C_6H_4$ | 4-(3'-$CH_2$OH-biphenyl) | 150 ppm | 0 |
| H | 3,5-diCl—$C_6H_3$ | 4-(3',5'-diCl-biphenyl) | 150 ppm | 7 |
| H | 4-Cl—$C_6H_4$ | 4-(4'-Cl-biphenyl) | 150 ppm | 9 |
| H | 4(4'-t-bu-biphenyl) | 4-biphenyl | 150 ppm | 0 |
| H | 4-biphenyl | 4-biphenyl | 150 ppm | 9 |
| H | 1-naphthyl | 4-biphenyl | 150 ppm | 9 |
| H | 4-$CH_3C_6H_4$ | 4-(4'-$CH_3$-biphenyl) | 150 ppm | 0 |
| H | 2-F—$C_6H_4$ | 4-(2'-F-biphenyl) | 150 ppm | 8 |
| H | 3-CN—$C_6H_4$ | 4-(3'-CN-biphenyl) | 150 ppm | 0 |
| H | 2-$CH_3$—$C_6H_4$ | 4-(2'-$CH_3$-biphenyl) | 150 ppm | 8 |
| H | 3,5-di$CF_3$—$C_6H_3$ | 4-(3',5'-di$CF_3$-biphenyl) | 150 ppm | 0 |
| H | 2,4-diCl—$C_6H_3$ | 4-biphenyl | 150 ppm | 9 |
| H | 3,4-diCl—$C_6H_3$ | 4-biphenyl | 150 ppm | 9 |
| H | 3,5-diCl—$C_6H_3$ | 4-biphenyl | 150 ppm | 9 |
| H | 3-Cl—$C_6H_4$ | 4-biphenyl | 150 ppm | 9 |
| H | 3,5-di$CF_3$—$C_6H_3$ | 4-biphenyl | 150 ppm | 9 |
| H | 2-$CF_3$—$C_6H_4$ | 4-biphenyl | 150 ppm | 8 |
| H | 3,5-diCl—$C_6H_3$ | 4-(3,2'-diOCH$_3$-biphenyl) | 150 ppm | 0 |
| H | 3-Cl—$C_6H_4$ | 4-(3-OCH$_3$-2'-Cl-biphenyl) | 150 ppm | 8 |

TABLE VII-continued

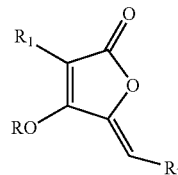

| | Test Compound | | | |
|---|---|---|---|---|
| R | R1 | R2 | Dose | Rating |
| H | 3,5-diCl—C$_6$H$_3$ | 4-(3-OCH$_3$-2'-Cl-biphenyl) | 150 ppm | 7 |
| H | 3-Cl—C$_6$H$_4$ | 4-(3-OCH$_3$-2'-CH$_3$-biphenyl) | 150 ppm | 7 |
| H | 3-Cl—C$_6$H$_4$ | 4-(3-CH$_3$-2'-OCH$_3$-biphenyl) | 150 ppm | 7 |
| H | 3-5-diCl—C$_6$H$_3$ | 4-(3-CH$_3$-2'-OCH$_3$-biphenyl) | 150 ppm | 0 |
| H | 3-5-diCl—C$_6$H$_3$ | 4-(3-OCH$_3$-2'-CH$_3$-biphenyl) | 150 ppm | 9 |
| H | 3-Cl—C$_6$H$_4$ | 4-(3-CH$_3$-2'-CF$_3$-biphenyl) | 150 ppm | 9 |
| H | 3-5-diCl—C$_6$H$_3$ | 4-(3-CH$_3$-2'-CF$_3$-biphenyl) | 150 ppm | 0 |
| H | 3-Cl—C$_6$H$_4$ | 4-(3,2'-diCH$_3$-biphenyl) | 150 ppm | 9 |
| H | 3,5-diCl—C$_6$H$_3$ | 4-(3-CH$_3$-2'-Cl-biphenyl) | 150 ppm | 7 |
| H | 3-Cl—C$_6$H$_4$ | 4-(3-CH$_3$-2'-Cl-biphenyl) | 150 ppm | 9 |
| H | 3,5-diCl—C$_6$H$_3$ | 4-(3,2'-diCH$_3$-biphenyl) | 150 ppm | 0 |
| H | 3,5-diCl—C$_6$H$_3$ | 4-(3-OCH$_3$-2'-CF$_3$-biphenyl) | 150 ppm | 0 |
| H | 3-Cl—C$_6$H$_4$ | 4-(3-OCH$_3$-2'-CF$_3$-biphenyl) | 150 ppm | 9 |
| H | 3,5-diCl—C$_6$H$_3$ | 4-(3-CH$_3$-2'-CH$_3$SO$_3$—biphenyl) | 150 ppm | 8 |
| H | 4-OCH$_3$—C$_6$H$_4$ | 4-biphenyl | 150 ppm | 9 |
| H | 3-CF$_3$—C$_6$H$_4$ | C$_6$H$_5$ | 150 ppm | 8 |
| H | 4-Cl—C$_6$H$_4$ | 3-CF$_3$—C$_6$H$_4$ | 150 ppm | 9 |
| H | C$_6$H$_5$ | 3-CF$_3$—C$_6$H$_4$ | 150 ppm | 0 |
| H | 2-naphthyl | 3-CF$_3$—C$_6$H$_4$ | 150 ppm | 9 |
| H | 2-naphthyl | 1-naphthyl | 150 ppm | 9 |
| H | 4-biphenyl | 4-Cl—C$_6$H$_4$ | 150 ppm | 9 |
| H | 4-Cl—C$_6$H$_4$ | 4-Cl—C$_6$H$_4$ | 150 ppm | 9 |
| H | 4-Cl—C$_6$H$_4$ | 1-naphthyl | 150 ppm | 9 |
| H | 3-CF$_3$—C$_6$H$_4$ | 3-CF$_3$—C$_6$H$_4$ | 150 ppm | 9 |
| H | 4-OCH$_3$—C$_6$H$_4$ | 2-naphthyl | 150 ppm | 0 |
| H | 4-OCH$_3$—C$_6$H$_4$ | 4-OCH$_3$—C$_6$H$_4$ | 150 ppm | 0 |
| H | 4-Cl—C$_6$H$_4$ | 4-OCH$_3$—C$_6$H$_4$ | 150 ppm | 0 |
| H | 4-OCH$_3$—C$_6$H$_4$ | 4-Cl—C$_6$H$_4$ | 150 ppm | 0 |
| H | 1-naphthyl | 4-Cl—C$_6$H$_4$ | 150 ppm | 0 |
| H | 3-CF$_3$—C$_6$H$_4$ | 2-naphthyl | 150 ppm | 9 |
| H | 1-naphthyl | 1-naphthyl | 150 ppm | 0 |
| H | 1-naphthyl | 3-CF$_3$—C$_6$H$_4$ | 150 ppm | 0 |
| H | 3-CF$_3$—C$_6$H$_4$ | 4-OCH$_3$—C$_6$H$_4$ | 150 ppm | 9 |
| H | 4-biphenyl | 2-CF$_3$—C$_6$H$_4$ | 150 ppm | 9 |
| H | 2-naphthyl | 2-naphthyl | 150 ppm | 9 |
| H | 4-biphenyl | 2-naphthyl | 150 ppm | 0 |
| H | 4-Cl—C$_6$H$_4$ | 2-naphthyl | 150 ppm | 9 |
| H | 1-naphthyl | 2-naphthyl | 150 ppm | 9 |
| H | 4-(3-F-biphenyl) | 2-CF$_3$—C$_6$H$_4$ | 150 ppm | 9 |
| H | 4-COCH$_3$—C$_6$H$_4$ | 2-CF$_3$—C$_6$H$_4$ | 150 ppm | 0 |
| H | 4-CN—C$_6$H$_4$ | 2-CF$_3$—C$_6$H$_4$ | 150 ppm | 7 |
| H | 4-F—C$_6$H$_4$ | 2-CF$_3$—C$_6$H$_4$ | 150 ppm | 0 |
| H | 3-biphenyl | 3-CF$_3$—C$_6$H$_4$ | 150 ppm | 0 |
| H | 3,5-diCl—C$_6$H$_3$ | 1-naphthyl | 150 ppm | 9 |
| H | 4-CF$_3$—C$_6$H$_4$ | 1-naphthyl | 150 ppm | 9 |
| H | 3-COCH$_3$—C$_6$H$_4$ | 1-naphthyl | 150 ppm | 8 |
| H | 4-(CH$_3$C=NOH)—C$_6$H$_4$ | 1-naphthyl | 150 ppm | 7 |
| H | 4-CO$_2$CH$_3$—C$_6$H$_4$ | 1-naphthyl | 150 ppm | 9 |
| H | 3,4-diCl—C$_6$H$_3$ | 4-(3',4'-diCl-biphenyl) | 150 ppm | 9 |
| H | 3-CHO—C$_6$H$_4$ | 1-naphthyl | 150 ppm | 0 |
| H | 3-CH$_2$OH—C$_6$H$_4$ | 1-naphthyl | 150 ppm | 0 |
| H | 3-(C=NOH)—C$_6$H$_4$ | 1-naphthyl | 150 ppm | 0 |
| H | 4-(3-F-biphenyl) | 4-Cl—C$_6$H$_4$ | 150 ppm | 9 |
| H | 4-Cl—C$_6$H$_4$ | 2-(4'-Cl-biphenyl) | 150 ppm | 0 |
| H | 4-(3-F-biphenyl) | 3,5-diCl—C$_6$H$_3$ | 150 ppm | 9 |
| H | 3-Cl—C$_6$H$_4$ | 2-(3'-Cl-biphenyl) | 150 ppm | 0 |
| H | 3-F-4-(1-morpholino)-C$_6$H$_3$ | 2-Cl-5-CF$_3$—C$_6$H$_3$ | 150 ppm | 0 |
| H | 4-Cl—C$_6$H$_4$ | 1-[(4-dimethylamino)-naphthyl] | 150 ppm | 0 |
| H | 3,5-diClC$_6$H$_3$ | 1-[(4-dimethylamino)-naphthyl] | 150 ppm | 0 |
| H | 4-CF$_3$—C$_6$H$_4$ | 1-[(4-dimethylamino)-naphthyl] | 150 ppm | 0 |

TABLE VII-continued

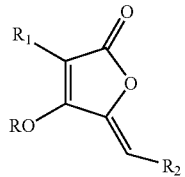

| | Test Compound | | | |
|---|---|---|---|---|
| R | R1 | R2 | Dose | Rating |
| H | 3-Cl—C$_6$H$_4$ | 3-F-4-[1-(4-CO$_2$C$_2$H$_5$-piperazinyl)]-C$_6$H$_3$ | 150 ppm | 7 |
| H | 4-CN—C$_6$H$_4$** | 4-(4'-Cl-biphenyl) | 150 ppm | 9 |
| H | 4-Cl—C$_6$H$_4$ | 4-(4'-CN-biphenyl) | 150 ppm | 9 |
| H | 4-Cl—C$_6$H$_4$* | 4-(4'-CN-biphenyl) | 150 ppm | 9 |
| H | 4-Cl—C$_6$H$_4$** | 4-CN—C$_6$H$_4$ | 150 ppm | 9 |
| H | 4-Cl—C$_6$H$_4$** | 3-Cl—C$_6$H$_4$ | 150 ppm | 9 |
| H | 3-CF$_3$—C$_6$H$_4$ | 4-Cl—C$_6$H$_4$ | 100 ppm | 9 |
| CH$_3$ | 4-Cl—C$_6$H$_4$** | 4-CN—C$_6$H$_4$ | 100 ppm | 0 |
| CO$_2$t-Bu | 4-Cl—C$_6$H$_4$** | 4-CN—C$_6$H$_4$ | 100 ppm | 9 |
| CO$_2$C$_6$H$_5$ | 4-Cl—C$_6$H$_4$** | 4-CN—C$_6$H$_4$ | 100 ppm | 9 |
| CO$_2$CH$_3$ | 4-Cl—C$_6$H$_4$** | 4-CN—C$_6$H$_4$ | 100 ppm | 9 |
| CH$_2$CH=CH$_2$ | 4-Cl—C$_6$H$_4$** | 4-CN—C$_6$H$_4$ | 100 ppm | 0 |
| H | 4-CF$_3$—C$_6$H$_4$** | 4-CN—C$_6$H$_4$ | 100 ppm | 9 |
| H | 4-CF$_3$—C$_6$H$_4$** | 4-Cl—C$_6$H$_4$ | 100 ppm | 9 |
| H | 4-CF$_3$—C$_6$H$_4$** | 4-CF$_3$—C$_6$H$_4$ | 100 ppm | 9 |
| H | 4-CF$_3$—C$_6$H$_4$** | 4-(4'-Cl-biphenyl) | 100 ppm | 9 |
| H | 4-CF$_3$—C$_6$H$_4$** | 4-(4'-CN-biphenyl) | 100 ppm | 9 |
| H | 4-CF$_3$—C$_6$H$_4$** | 4-F—C$_6$H$_4$ | 100 ppm | 9 |
| H | 4-F—C$_6$H$_4$** | 4-CN—C$_6$H$_4$ | 100 ppm | 9 |
| H | 4-F—C$_6$H$_4$** | 4-Cl—C$_6$H$_4$ | 100 ppm | 9 |
| H | 4-F—C$_6$H$_4$** | 4-CF$_3$—C$_6$H$_4$ | 100 ppm | 9 |
| H | 4-F—C$_6$H$_4$** | 4-F—C$_6$H$_4$ | 100 ppm | 9 |
| H | 4-F—C$_6$H$_4$** | 4-(4'-CN-biphenyl) | 100 ppm | 9 |
| H | 4-F—C$_6$H$_4$** | 4-(4'-Cl-biphenyl) | 100 ppm | 9 |
| H | 3-Cl—C$_6$H$_4$** | 4-CN—C$_6$H$_4$ | 100 ppm | 9 |
| H | 3-Cl—C$_6$H$_4$** | 4-Cl—C$_6$H$_4$ | 100 ppm | 9 |
| H | 3-Cl—C$_6$H$_4$** | 4-CF$_3$—C$_6$H$_4$ | 100 ppm | 9 |
| H | 3-Cl—C$_6$H$_4$** | 4-(4'-Cl-biphenyl) | 100 ppm | 9 |
| H | 3-Cl—C$_6$H$_4$** | 4-(4'-CN-biphenyl) | 100 ppm | 9 |
| H | 3-Cl—C$_6$H$_4$** | 4-F—C$_6$H$_4$ | 100 ppm | 9 |
| H | 3-CF$_3$—C$_6$H$_4$** | 4-CN—C$_6$H$_4$ | 100 ppm | 9 |
| H | 3-CF$_3$—C$_6$H$_4$** | 4-F—C$_6$H$_4$ | 100 ppm | 9 |
| H | 3-CF$_3$—C$_6$H$_4$** | 4-CF$_3$—C$_6$H$_4$ | 100 ppm | 9 |
| H | 3-CF$_3$—C$_6$H$_4$** | 4-(4'-Cl-biphenyl) | 100 ppm | 9 |
| H | 3-CF$_3$—C$_6$H$_4$** | 4-(4'-CN-biphenyl) | 100 ppm | 9 |
| H | 3-CN—C$_6$H$_4$** | 4-CN—C$_6$H$_4$ | 100 ppm | 9 |
| H | 3-CN—C$_6$H$_4$** | 4-Cl—C$_6$H$_4$ | 100 ppm | 9 |
| H | 3-CN—C$_6$H$_4$** | 4-CF$_3$—C$_6$H$_4$ | 100 ppm | 9 |
| H | 3-CN—C$_6$H$_4$** | 4-(4'-Cl-biphenyl) | 100 ppm | 9 |
| H | 3-CN—C$_6$H$_4$** | 4-(4'-CN-biphenyl) | 100 ppm | 9 |
| H | 3-CN—C$_6$H$_4$** | 4-F—C$_6$H$_4$ | 100 ppm | 7 |
| H | 4-CN—C$_6$H$_4$** | 4-CF$_3$-C$_6$H$_4$ | 100 ppm | 9 |
| H | 4-CN—C$_6$H$_4$** | 3-CF$_3$—C$_6$H$_4$ | 100 ppm | 9 |
| H | 4-CN—C$_6$H$_4$** | 4-(4'-CF$_3$-biphenyl) | 100 ppm | 9 |
| H | 4-CN—C$_6$H$_4$** | 4-F—C$_6$H$_4$ | 100 ppm | 9 |
| H | 4-Cl—C$_6$H$_4$** | 4-CF$_3$—C$_6$H$_4$ | 100 ppm | 9 |
| H | 4-Cl—C$_6$H$_4$** | 2-CF$_3$—C$_6$H$_4$ | 100 ppm | 9 |
| H | 4-Cl—C$_6$H$_4$** | 4-(4'-CF$_3$-biphenyl) | 100 ppm | 9 |
| H | 4-Cl—C$_6$H$_4$** | 4-F—C$_6$H$_4$ | 100 ppm | 9 |
| H | 4-(4'-Cl-biphenyl)** | 4-CF$_3$—C$_6$H$_4$ | 100 ppm | 9 |
| H | 4-(4'-Cl-biphenyl)** | 4-CN—C$_6$H$_4$ | 100 ppm | 9 |
| H | 4-(4'-Cl-biphenyl)** | 4-Cl—C$_6$H$_4$ | 100 ppm | 9 |
| H | 4-(4'-CN-biphenyl)** | 4-CF$_3$—C$_6$H$_4$ | 100 ppm | 9 |
| H | 4-(4'-CN-biphenyl)** | 4-CN—C$_6$H$_4$ | 100 ppm | 9 |
| H | 4-(4'-CN-biphenyl)** | 4-Cl—C$_6$H$_4$ | 100 ppm | 9 |
| H | 4-Cl—C$_6$H$_4$** | 3,4-diCl—C$_6$H$_4$ | 100 ppm | 9 |
| H | 4-Cl—C$_6$H$_4$** | 2,4-diCl—C$_6$H$_4$ | 100 ppm | 9 |
| H | 4-Cl—C$_6$H$_4$** | 3-F-4-CF$_3$—C$_6$H$_4$ | 100 ppm | 9 |
| H | 4-CN—C$_6$H$_4$** | 3,4-diCl—C$_6$H$_4$ | 100 ppm | 9 |
| H | 4-CN—C$_6$H$_4$** | 2,4-diCl—C$_6$H$_4$ | 100 ppm | 9 |
| H | 4-CN—C$_6$H$_4$** | 3-F-4-CF$_3$—C$_6$H$_4$ | 100 ppm | 9 |
| CH$_3$ | 3-CF$_3$—C$_6$H$_4$ | 3-CF$_3$—C$_6$H$_4$ | 150 ppm | 0 |
| CH$_3$ | 4-OCH$_3$—C$_6$H$_4$ | C$_6$H$_5$ | 150 ppm | 0 |
| CH$_3$ | 4-OCH$_3$—C$_6$H$_4$ | 3-CF$_3$—C$_6$H$_4$ | 150 ppm | 0 |

TABLE VII-continued

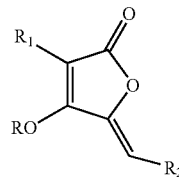

Test Compound

| R | R1 | R2 | Dose | Rating |
|---|---|---|---|---|
| $CH_3$ | 3-$CF_3$—$C_6H_4$ | $C_6H_5$ | 150 ppm | 0 |
| $CH_3$ | 4-Cl—$C_6H_4$ | $C_6H_5$ | 150 ppm | 0 |
| $CH_3$ | $C_6H_5$ | 3-$CF_3$—$C_6H_4$ | 150 ppm | 0 |
| H | 4-biphenyl | 3-F-5-$CF_3$—$C_6H_3$ | 200 μM | 9 |
| H | 4-(3-F-biphenyl) | 3-F-5-$CF_3$—$C_6H_3$ | 200 μM | 9 |
| H | 4-(4'-nBu-biphenyl) | 3-F-5-$CF_3$—$C_6H_3$ | 200 μM | 9 |
| H | 3-biphenyl | 3-F-5-$CF_3$—$C_6H_3$ | 200 μM | 9 |
| H | 4-(2-F-biphenyl) | 2-Cl-3-$CF_3$—$C_6H_3$ | 200 μM | 9 |
| H | 4-(4'-nPr-biphenyl) | 2-Cl-3-$CF_3$—$C_6H_3$ | 200 μM | 9 |
| H | 4-(4'-nBu-biphenyl) | 2-Cl-3-$CF_3$—$C_6H_3$ | 200 μM | 9 |
| H | 4-(4'-nPr-biphenyl) | 2-F-5-$CF_3$—$C_6H_3$ | 200 μM | 9 |
| H | 4-(4'-nBu-biphenyl) | 2-F-5-$CF_3$—$C_6H_3$ | 200 μM | 0 |
| H | 3-biphenyl | 2-F-5-$CF_3$—$C_6H_3$ | 200 μM | 9 |
| H | 4-(4'-$OC_2H_5$-biphenyl) | 2-F-5-$CF_3$—$C_6H_3$ | 200 μM | 9 |
| H | 4-biphenyl | 2-Cl-5-$CF_3$—$C_6H_3$ | 200 μM | 9 |
| H | 4-(4'-nPr-biphenyl) | 2-Cl-5-$CF_3$—$C_6H_3$ | 200 μM | 0 |
| H | 4-(4'-tBu-biphenyl) | 3-$CF_3$—$C_6H_4$ | 200 μM | 0 |
| H | 3-isopropyl-$C_6H_4$ | 2-Cl-5-$CF_3$—$C_6H_3$ | 200 μM | 0 |
| H | 4-($C_2H_5$)—$C_6H_4$ | 2-Cl-5-$CF_3$—$C_6H_3$ | 200 μM | 9 |
| H | 4-$CH_3$—$C_6H_4$ | 2-Cl-5-$CF_3$—$C_6H_3$ | 200 μM | 0 |
| H | 2,3-di-$CH_3$—$C_6H_3$ | 2-Cl-5-$CF_3$—$C_6H_3$ | 200 μM | 0 |
| H | 3,4-di-$CH_3$—$C_6H_3$ | 2-Cl-5-$CF_3$—$C_6H_3$ | 200 μM | 0 |
| H | 3,5-di-$CH_3$—$C_6H_3$ | 2-Cl-5-$CF_3$—$C_6H_3$ | 200 μM | 0 |
| H | 2,5-di-$CH_3$—$C_6H_3$ | 2-Cl-5-$CF_3$—$C_6H_3$ | 200 μM | 0 |
| H | 4-isopropyl-$C_6H_4$ | 2-Cl-3-$CF_3$—$C_6H_3$ | 200 μM | 9 |
| H | 4-$CH_3$—$C_6H_4$ | 2-Cl-3-$CF_3$—$C_6H_3$ | 200 μM | 9 |
| H | 3,4-di-$CH_3$—$C_6H_3$ | 2-Cl-3-$CF_3$—$C_6H_3$ | 200 μM | 9 |
| H | 4-biphenyl | 3-$CF_3$—$C_6H_4$ | 200 μM | 9 |
| H | 3,5-diCl—$C_6H_3$ | 3-F-4-[1-(4-$CO_2C_2H_5$-piperazinyl)]-$C_6H_3$ | 150 ppm | 0 |
| H | 3-Cl—$C_6H_4$ | 1-(4-$OCH_3$-naphthyl) | 150 ppm | 9 |
| H | 3,5-diCl—$C_6H_3$ | 1-(4-$OCH_3$-naphthyl) | 150 ppm | 0 |
| H | 3-Cl—$C_6H_4$ | 1-[4-(N-morpholino)-naphthyl)] | 150 ppm | 0 |
| H | 3,5-diCl—$C_6H_3$ | 1-[4-(N-morpholino)-naphthyl)] | 150 ppm | 0 |
| H | 3,5-diCl—$C_6H_3$ | 3-(benzyloxy)-$C_6H_4$ | 150 ppm | 0 |
| H | 3,5-diCl—$C_6H_3$ | 2-(benzyloxy)-$C_6H_4$ | 150 ppm | 0 |
| H | 3,5-diCl—$C_6H_3$ | 3-Cl-4-{1-[4-(2-Cl—$C_6H_4$)-piperazinyl]}-$C_6H_3$ | 150 ppm | 0 |
| H | 3,5-diCl—$C_6H_3$ | 3-($CONHCH_2CONHCH_2$—$CO_2C_2H_5$)—$C_6H_4$ | 150 ppm | 0 |
| H | 3,5-diCl—$C_6H_3$ | 3-($CONHCH_2CONHCH_2$—$CO2C_2H_5$)—$C_6H_4$ | 150 ppm | 0 |
| H | 3,5-diCl—$C_6H_3$ | 4-(3-$CH_3$-2-$COCH_3$-biphenyl) | 150 ppm | 0 |
| H | 4-CN—$C_6H_4$* | 4-(4'-CN-biphenyl) | 150 ppm | 9 |
| H | 4-CN—$C_6H_4$** | 4-Cl—$C_6H_4$ | 150 ppm | 9 |
| H | 4-CN—$C_6H_4$** | 4-CN—$C_6H_4$ | 150 ppm | 9 |
| H | 4-F—$C_6H_4$** | 4-$OCF_3$—$C_6H_4$ | 100 ppm | 9 |
| H | 4-CN—$C_6H_4$** | 4-$OCF_3$—$C_6H_4$ | 100 ppm | 9 |
| H | 4-CN—$C_6H_4$** | 4-$OCHF_2$—$C_6H_4$ | 100 ppm | 9 |
| H | 4-CN—$C_6H_4$** | 4-$OCF_2CHF_2$—$C_6H_4$ | 100 ppm | 9 |
| H | 4-CN—$C_6H_4$** | 5-chlorothiophen-2-yl | 100 ppm | 9 |
| H | 4-CN—$C_6H_4$** | 2,2difluoro-1,3-dioxol-$C_6H_3$-5-yl | 100 ppm | 9 |
| H | 4-$OCF_3$—$C_6H_4$** | 3,5-diCl—$C_6H_3$ | 100 ppm | 9 |
| H | 4-$OCF_3$—$C_6H_4$** | 3,4-diF—$C_6H_3$ | 100 ppm | 9 |
| H | 4-$OCF_3$—$C_6H_4$** | 4-n-propoxy-$C_6H_4$ | 100 ppm | 0 |
| H | 4-$OCF_3$—$C_6H_4$** | 3,4-diCl—$C_6H_3$ | 100 ppm | 9 |
| H | 4-$OCF_3$—$C_6H_4$** | 3-F-4-$CF_3$—$C_6H_3$ | 100 ppm | 9 |
| H | 4-$OCF_3$—$C_6H_4$** | 5-chlorothiophen-2-yl | 100 ppm | 9 |
| H | 4-$OCF_3$—$C_6H_4$** | thiophen-2-yl | 100 ppm | 0 |
| H | 4-$OCF_3$—$C_6H_4$** | 4-phenoxy-$C_6H_4$ | 100 ppm | 0 |
| H | 4-$OCF_3$—$C_6H_4$** | pyridine-3-yl | 100 ppm | 0 |

TABLE VII-continued

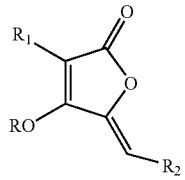

| | Test Compound | | | |
|---|---|---|---|---|
| R | R1 | R2 | Dose | Rating |
| H | 4-OCF$_3$—C$_6$H$_4$** | 4-OCF$_3$—C$_6$H$_4$ | 100 ppm | 9 |
| H | 4-OCF$_3$—C$_6$H$_4$** | 4-F—C$_6$H$_4$ | 100 ppm | 9 |
| H | 4-OCF$_3$—C$_6$H$_4$** | 4-CN—C$_6$H$_4$ | 100 ppm | 9 |
| H | 4-OCF$_3$—C$_6$H$_4$** | 4-Cl—C$_6$H$_4$ | 100 ppm | 9 |
| H | 4-OCF$_3$—C$_6$H$_4$** | 4-OCHF$_2$—C$_6$H$_4$ | 100 ppm | 9 |
| H | 4-OCF$_3$—C$_6$H$_4$** | 2-F-5-CF$_3$—C$_6$H$_3$ | 100 ppm | 9 |
| H | 4-OCF$_3$—C$_6$H$_4$** | 4-CF$_3$—C$_6$H$_4$ | 100 ppm | 9 |
| H | 4-OCF$_3$—C$_6$H$_4$** | 3-F-5-CF$_3$—C$_6$H$_3$ | 100 ppm | 9 |
| H | 4-OCF$_3$—C$_6$H$_4$** | 2-F-4-CF$_3$—C$_6$H$_3$ | 100 ppm | 9 |
| H | 4-OCF$_3$—C$_6$H$_4$** | 4-OCF$_2$CHF$_2$—C$_6$H$_4$ | 100 ppm | 9 |
| H | 4-OCF$_3$—C$_6$H$_4$** | 2,2difluoro-1,3-dioxol-C$_6$H$_3$-5-yl | 100 ppm | 9 |
| H | 4-OCF$_3$—C$_6$H$_4$** | pyridine-4-yl | 100 ppm | 0 |
| H | 4-OCF$_3$—C$_6$H$_4$** | pyridine-2-yl | 100 ppm | 0 |
| H | 4-OCF$_3$—C$_6$H$_4$** | 3-Br-pyridine-2-yl | 100 ppm | 0 |
| H | 4-OCF$_3$—C$_6$H$_4$** | 4-(4-F-phenyl)-pyridin-3-yl | 100 ppm | 9 |
| H | 4-OCF$_3$—C$_6$H$_4$** | 4-(thiophen-2-yl)-pyridin-3-yl | 100 ppm | 9 |
| H | 4-OCF$_3$—C$_6$H$_4$** | 4-(4-OCF$_3$-phenyl)-pyridin-3-yl | 100 ppm | 9 |
| H | 4-OCF$_3$—C$_6$H$_4$** | 4-(5-Cl-thiophen-2-yl)-pyridin-3-yl | 100 ppm | 9 |
| H | 4-OCF$_3$—C$_6$H$_4$** | 4-(4-Cl-phenyl)-pyridin-3-yl | 100 ppm | 9 |
| H | 4-OCF$_3$—C$_6$H$_4$** | 4-(3-Cl-phenyl)-pyridin-3-yl | 100 ppm | 9 |
| H | 4-OCF$_3$—C$_6$H$_4$** | 4-Br-pyridine-3-yl | 100 ppm | 9 |
| H | 4-OCF$_3$—C$_6$H$_4$** | 3-Cl-pyridine-4-yl | 100 ppm | 9 |
| H | 4-OCF$_3$—C$_6$H$_4$** | 4-cyclopropylmethoxy-C$_6$H$_4$ | 100 ppm | 0 |
| H | 4-OCF$_3$—C$_6$H$_4$** | 4-(5-Cl-thiophen-2-yl)-C$_6$H$_4$ | 100 ppm | 9 |
| H | 4-OCF$_3$—C$_6$H$_4$** | 2-methyl-1H-imidazol-4-yl | 100 ppm | 0 |
| H | 4-OCF$_3$—C$_6$H$_4$** | 5-chloro-1,3-dimethyl-1H-pyrazol-4-yl | 100 ppm | 0 |
| H | 4-OCF$_3$—C$_6$H$_4$** | 5-methyl-1-o-tolyl-1H-pyrazol-4-yl | 100 ppm | 0 |
| H | 4-OCF$_3$—C$_6$H$_4$** | 2-phenyl-1H-imidazol-4-yl | 100 ppm | 0 |
| H | 4-OCF$_3$—C$_6$H$_4$** | 2-Cl-pyridine-3-yl | 100 ppm | 9 |
| H | 4-OCF$_3$—C$_6$H$_4$** | 4-chloro-1-methyl-1H-pyrazol-3-yl | 100 ppm | 0 |
| H | 4-OCF$_3$—C$_6$H$_4$** | 5-(4-F-3-CF$_3$-phenyl)-furan-2-yl | 100 ppm | 9 |
| H | 4-OCF$_3$—C$_6$H$_4$** | 5-chloro-1-methyl-3-trifluoromethyl-1H-imidazol-3-yl | 100 ppm | 0 |
| H | 4-OCF$_3$—C$_6$H$_4$** | 5-bromo-1-methyl-1H-imidazol-3-yl | 100 ppm | 0 |
| H | 4-OCF$_3$—C$_6$H$_4$** | 1-(4-methoxyphenyl)-5-methyl-1H-pyrazol-4-yl | 100 ppm | 0 |
| H | 4-OCF$_3$—C$_6$H$_4$** | 1-(4-fluorophenyl)-5-methyl-1H-pyrazol-4-yl | 100 ppm | 0 |
| H | 4-OCF$_3$—C$_6$H$_4$** | 1-(phenyl)-5-methyl-1H-pyrazol-4-yl | 100 ppm | 0 |
| H | 4-OCF$_3$—C$_6$H$_4$** | 2-methanesulfanyl-nicotinonitrile | 100 ppm | 9 |
| H | 4-OCF$_3$—C$_6$H$_4$** | 5-bromo-furan-2-yl | 100 ppm | 9 |
| H | 4-OCF$_3$—C$_6$H$_4$** | 6-phenoxy-pyridin-3-yl | 100 ppm | 9 |
| H | 4-OCF$_3$—C$_6$H$_4$** | 4-(1,2,4-triazol-1-yl)-C$_6$H$_4$ | 100 ppm | 9 |
| H | 4-OCF$_3$—C$_6$H$_4$** | 5-(pyridine-2-yl)-thiphen-2-yl | 100 ppm | 9 |
| H | 4-OCF$_3$—C$_6$H$_4$** | 5-(6-morpholino-4-yl)-pyridin-3-yl | 100 ppm | 0 |
| H | 4-OCF$_3$—C$_6$H$_4$** | 4-(4-methyl-piperazin-1-yl)-C$_6$H$_4$ | 100 ppm | 0 |
| H | 4-OCF$_3$—C$_6$H$_4$** | 4-(thiophen-2-yl)-C$_6$H$_4$ | 100 ppm | 9 |
| H | 4-OCF$_3$—C$_6$H$_4$** | 4-(pyrrol-1-yl)-C$_6$H$_4$ | 100 ppm | 9 |
| H | 4-OCF$_3$—C$_6$H$_4$** | 4-(4'-Cl-biphenyl) | 100 ppm | 9 |

TABLE VII-continued

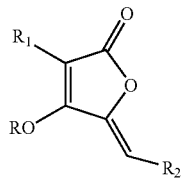

| | | Test Compound | | |
|---|---|---|---|---|
| R | R1 | R2 | Dose | Rating |
| H | 4-OCF$_3$—C$_6$H$_4$** | 4-(4'-CN-biphenyl) | 100 ppm | 9 |
| H | 4-OCF$_3$—C$_6$H$_4$** | 2,5-dimethyl-2H-pyrazol-3-yl | 100 ppm | 0 |
| H | thiophen-2-yl | 4-CN—C$_6$H$_4$ | 100 ppm | 0 |
| H | thiophen-2-yl | 4-Cl—C$_6$H$_4$ | 100 ppm | 7 |
| H | thiophen-2-yl | 4-CF$_3$—C$_6$H$_4$ | 100 ppm | 7 |
| H | 5-chlorothiophen-2-yl | 4-Cl—C$_6$H$_4$ | 100 ppm | 9 |
| H | 5-chlorothiophen-2-yl | 4-CN—C$_6$H$_4$ | 100 ppm | 9 |
| H | 5-chlorothiophen-2-yl | 4-CF$_3$—C$_6$H$_4$ | 100 ppm | 9 |
| H | 5-chlorothiophen-2-yl | 4-OCF$_3$—C$_6$H$_4$ | 100 ppm | 9 |
| H | 5-chlorothiophen-2-yl | 4-OCHF$_2$—C$_6$H$_4$ | 100 ppm | 9 |
| H | 5-chlorothiophen-2-yl | 3,4-diCl—C$_6$H$_3$ | 100 ppm | 9 |
| H | 5-chlorothiophen-2-yl | 3,4-diF—C$_6$H$_3$ | 100 ppm | 9 |
| H | 5-chlorothiophen-2-yl | 4-F-3-CF$_3$—C$_6$H$_3$ | 100 ppm | 9 |
| H | 5-chlorothiophen-2-yl | 4-F—C$_6$H$_4$ | 100 ppm | 9 |
| H | 5-chlorothiophen-2-yl | 4-cyclopropylmethoxy-C$_6$H$_4$ | 100 ppm | 9 |
| H | 5-chlorothiophen-2-yl | 5-chlorothiophen-2-yl | 100 ppm | 9 |
| H | 4-Cl—C$_6$H$_4$** | 4-cyclopropylmethoxy-C$_6$H$_4$ | 100 ppm | 7 |
| H | 4-Cl—C$_6$H$_4$** | 4-SCF$_3$—C$_6$H$_4$ | 100 ppm | 9 |

*E isomer
**Mixture of Z and E isomers

EXAMPLE 327

In Vivo Evaluation of the Efficacy of Test Compounds Against T. colubriformis In this evaluation, gerbils are infected with *Trichostrongylus columbriformis* infective larvae at a concentration of approximately 800 L$_3$/mL. Larvae for gerbil infections are cultured from feces from sheep previously infected with *T. colubriformis*. One week post infection, test compounds are administered by gavage as a single oral dose of 50 mg/kg of body weight. For each group of 3 gerbils, 10 mg of test compound are dissolved in 2 mL of PEG 400:DMSO (1:2 v/v) and each animal is administered the test solution at a rate of 0.1 mL/10 g of body weight. Treatments are randomly allocated to groups of 3 infected gerbils each; 35 groups are treated with test compounds; 4 groups are untreated (administered vehicle only) as a negative control; and one group is treated with a known endectoside, NEMADECTIN as a positive control. All animals are observed daily for morbidity and mortality. Four days post-treatment, all animals are weighed and necropsied. Worm counts are conducted with the use of stereoscopes and counters. The results are recorded as % mortality as compared to that of the negative control for the worms. Toxicity is indicated for those groups having one or more animals expired or demonstrating significant weight loss as compared to the negative control. The data are shown in Table VIII, wherein all test compounds are the Z isomer, unless otherwise noted.

TABLE VIII

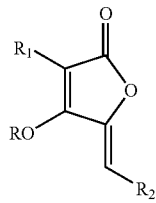

| | | Test Compound | | |
|---|---|---|---|---|
| R | R1 | R2 | Mortality | Toxicity |
| H | 4-biphenyl | 4-CF$_3$—C$_6$H$_4$ | 0.00 | − |
| H | 4-(3-F-biphenyl) | 3-CF$_3$—C$_6$H$_4$ | 20.60 | − |
| H | 4-CN—C$_6$H$_4$ | 4-(4'CN-biphenyl) | 88.60 | + |
| H | 4-Cl—C$_6$H$_4$ | 4-(4'-Cl-biphenyl) | 61.33 | + |

TABLE VIII-continued

[Structure: a furanone ring with R1 at position 3, RO- at position 4, and =CH-R2 exocyclic alkene at position 5, with C=O at position 2]

Test Compound

| R | R1 | R2 | Mortality | Toxicity |
|---|----|----|-----------|----------|
| H | 4-Cl—C₆H₄ | 4-biphenyl | 33.10 | + |
| H | 1-naphthyl | 4-biphenyl | 18.50 | − |
| H | 2-F—C₆H₄ | 4-(2'F-biphenyl) | 12.40 | − |
| H | 2-CH₃—C₆H₄ | 4-(2'-CH₃-biphenyl) | 21.30 | − |
| H | 2,4-diCl—C₆H₃ | 4-biphenyl | 24.50 | − |
| H | 3,5-diCl—C₆H₃ | 4-biphenyl | 52.60 | + |
| H | 3-Cl—C₆H₄ | 4-biphenyl | 19.40 | − |
| H | 3,5-diCF₃—C₆H₃ | 4-biphenyl | 60.80 | + |
| H | 2-CF₃—C₆H₄ | 4-biphenyl | 20.20 | − |
| H | 3-Cl—C₆H₄ | 4-(3-OCH₃—2'-Cl-biphenyl) | 0.00 | − |
| H | 3-Cl—C₆H₄ | 4-(3-CH₃—2'-OCH₃-biphenyl) | 0.00 | − |
| H | 3-Cl—C₆H₄ | 4-(3-CH₃—2'-CF₃-biphenyl) | 11.20 | − |
| H | 3-Cl—C₆H₄ | 4-(3,2'-diCH₃-biphenyl) | 10.80 | − |
| H | 3-Cl—C₆H₄ | 4-(3-CH₃—2'-Cl-biphenyl) | 16.90 | − |
| H | 3-Cl—C₆H₄ | 4-(3-OCH₃—2'-CF₃-biphenyl) | 29.50 | + |
| H | 4-OCH₃—C₆H₄ | 4-biphenyl | 44.90 | − |
| H | 4-(3-F-biphenyl) | 4-(3-F-biphenyl) | 17.00 | − |
| H | 3-CF₃—C₆H₄ | 2-naphthyl | 35.20 | − |
| H | 2-naphthyl | 1-naphthyl | 36.10 | − |
| H | 4-Cl—C₆H₄ | 4-Cl—C₆H₄ | 79.78 | + |
| H | 4-Cl—C₆H₄ | 4-Cl—C₆H₄ | 79.78 | + |
| H | 3-CF₃—C₆H₄ | 3-CF₃—C₆H₄ | 10.10 | − |
| H | 4-Cl—C₆H₄ | 4-OCH₃—C₆H₄ | 7.10 | − |
| H | 3-CF₃—C₆H₄ | 4-OCH₃—C₆H₄ | 3.10 | − |
| H | 4-biphenyl | 2-CF₃—C₆H₄ | 23.90 | − |
| H | 2-naphthyl | 2-naphthyl | 13.80 | − |
| H | 4-Cl—C₆H₄ | 2-naphthyl | 52.80 | − |
| H | 1-naphthyl | 2-naphthyl | 28.90 | − |
| H | 4-(3-F-biphenyl) | 2-CF₃—C₆H₄ | 51.60 | − |
| H | 4-CN—C₆H₄ | 2-CF₃—C₆H₄ | 69.78 | − |
| H | 3,5-diCl—C₆H₃ | 1-naphthyl | 0.00 | − |
| H | 3-COCH₃—C₆H₄ | 1-naphthyl | 10.70 | − |
| H | 3,4-diCl—C₆H₃ | 4-(3',4'-diCl-biphenyl) | 22.00 | − |
| H | 4-(3-F-biphenyl) | 4-Cl-C₆H₄ | 22.00 | − |
| H | 4-CN—C₆H₄* | 4-(4'-CN-biphenyl) | 88.07 | − |
| H | 4-CN—C₆H₄ | 4-Cl—C₆H₄ | 90.20 | + |
| H | 4-CN—C₆H₄ | 4-CN—C₆H₄ | 62.43 | + |
| H | 4-CN—C₆H₄ | 4-(4'-Cl-biphenyl) | 64.33 | + |
| H | 4-Cl—C₆H₄ | 4-(4'-CN-biphenyl) | 48.90 | + |
| H | 4-Cl—C₆H₄* | 4-(4'-CN-biphenyl) | 23.80 | − |
| H | 4-Cl—C₆H₄ | 4-CN—06H4 | 84.54 | + |
| H | 4-Cl—C₆H₄ | 3-Cl-C₆H₄ | 25.40 | − |
| H | 3,4-diCl—C₆H₃ | 4-biphenyl | 23.00 | − |
| H | 3,5-diCl—C₆H₃ | 4-(3-OCH₃—2'-Cl-biphenyl) | 41.00 | − |
| H | 3-biphenyl | 3-F-5-CF₃—C₆H₄ | 0.00 | − |
| H | 3-biphenyl | 2-F-5-CF₃—C₆H₄ | 38.40 | − |
| H | 4-biphenyl | 2-Cl—5-CF₃—C₆H₄ | 38.40 | − |
| H | 4-(C₂H₅)—C₆H₄ | 2-Cl—5-CF₃—C₆H₄ | 39.00 | − |
| H | 3,4-diCH₃—C₆H₄ | 2-Cl—3-CF₃—C₆H₄ | 36.50 | − |
| H | 2-CF₃—C₆H₄ | C₆H₅ | 34.60 | − |
| H | 4-biphenyl | 4-Cl—C₆H₄ | 44.70 | − |
| H | 4-Cl—C₆H₄ | 1-naphthyl | 0.00 | − |
| H | 3-CF₃—C₆H₄ | 4-Cl—C₆H₄ | 21.60 | − |
| CH₃ | 4-Cl—C₆H₄** | 4-CN—C₆H₄ | 0.00 | − |
| CO₂tBu | 4-Cl—C₆H₄** | 4-CN—C₆H₄ | 0.00 | − |
| CO₂C₆H₅ | 4-Cl—C₆H₄** | 4-CN—C₆H₄ | 0.00 | − |
| CO₂CH₃ | 4-Cl—C₆H₄** | 4-CN—C₆H₄ | 96.90 | − |
| CH₂CH=CH₂ | 4-Cl—C₆H₄** | 4-CN—C₆H₄ | 0.00 | − |
| H | 4-CF₃—C₆H₄** | 4-(4'-CN-biphenyl) | 91.50 | − |
| H | 4-CF₃—C₆H₄** | 4-F—C₆H₄ | 95.80 | + |
| H | 4-F—C₆H₄** | 4-CN—C₆H₄ | 14.70 | − |
| H | 4-F—C₆H₄** | 4-Cl—C₆H₄ | 0.00 | − |
| H | 4-F—C₆H₄** | 4-CF₃—C₆H₄ | 25.60 | − |
| H | 4-F—C₆H₄** | 4-F—C₆H₄ | 0.00 | − |

TABLE VIII-continued $$\text{structure with R}_1, \text{RO}, \text{R}_2 \text{ substituents on a furanone ring}$$

Test Compound

| R | R1 | R2 | Mortality | Toxicity |
|---|---|---|---|---|
| H | 4-F—C$_6$H$_4$** | 4-(4'-CN-biphenyl) | 31.80 | − |
| H | 4-F—C$_6$H$_4$** | 4-(4'-Cl-biphenyl) | 1.60 | − |
| H | 3-Cl—C$_6$H$_4$** | 4-CN—C$_6$H$_4$ | 43.70 | − |
| H | 3-Cl—C$_6$H$_4$** | 4-Cl—C$_6$H$_4$ | 18.80 | − |
| H | 3-Cl—C$_6$H$_4$** | 4-CF$_3$—C$_6$H$_4$ | 57.90 | − |
| H | 3-Cl—C$_6$H$_4$** | 4-(4'-Cl-biphenyl) | 37.60 | − |
| H | 3-Cl—C$_6$H$_4$** | 4-(4'-CN-biphenyl) | 32.00 | − |
| H | 3-Cl—C$_6$H$_4$** | 4-F—C$_6$H$_4$ | 3.00 | − |
| H | 3-CF$_3$—C$_6$H$_4$** | 4-CN—C$_6$H$_4$ | 0.00 | − |
| H | 3-CF$_3$—C$_6$H$_4$** | 4-F—C$_6$H$_4$ | 36.40 | − |
| H | 3-CF$_3$—C$_6$H$_4$** | 4-CF$_3$—C$_6$H$_4$ | 0.00 | − |
| H | 3-CF$_3$—C$_6$H$_4$** | 4-(4'-Cl-biphenyl) | 31.30 | − |
| H | 3-CF$_3$—C$_6$H$_4$** | 4-(4'-CN-biphenyl) | 47.50 | − |
| H | 3-CN—C$_6$H$_4$** | 4-CN—C$_6$H$_4$ | 25.50 | − |
| H | 3-CN—C$_6$H$_4$** | 4-Cl—C$_6$H$_4$ | 0.00 | − |
| H | 3-CN—C$_6$H$_4$** | 4-CF$_3$—C$_6$H$_4$ | 0.00 | − |
| H | 3-CN—C$_6$H$_4$** | 4-(4'-Cl-biphenyl) | 0.00 | − |
| H | 3-CN—C$_6$H$_4$** | 4-(4'-CN-biphenyl) | 30.30 | − |
| H | 3-CN—C$_6$H$_4$** | 4-F—C$_6$H$_4$ | 0.00 | − |
| H | 4-CN—C$_6$H$_4$** | 3-CF$_3$—C$_6$H$_4$ | 50.00 | − |
| H | 4-CN—C$_6$H$_4$** | 4-F—C$_6$H$_4$ | 82.10 | − |
| H | 4-Cl—C$_6$H4** | 4-(4'-CF$_3$-biphenyl) | 0.00 | − |
| H | 4-Cl—C$_6$H$_4$** | 4-F—C$_6$H$_4$ | 72.60 | + |
| H | 4-(4'-Cl-biphenyl)** | 4-CF$_3$—C$_6$H$_4$ | 21.30 | − |
| H | 4-(4'-Cl-biphenyl)** | 4-CN—C$_6$H$_4$ | 0.00 | − |
| H | 4-(4'-Cl-biphenyl)** | 4-Cl—C$_6$H$_4$ | 0.00 | − |
| H | 4-(4'-CN-biphenyl)** | 4-CF$_3$—C$_6$H$_4$ | 24.90 | − |
| H | 4-(4'-CN-biphenyl)** | 4-CN—C$_6$H$_4$ | 29.80 | − |
| H | 4-(4'-CN-biphenyl)** | 4-Cl—C$_6$H$_4$ | 13.10 | − |
| H | 4-Cl—C$_6$H$_4$** | 3,4-diCl—C$_6$H$_4$ | 58.0 | − |
| H | 4-Cl—C$_6$H$_4$** | 2,4-diCl—C$_6$H$_4$ | 91.40 | − |
| H | 4-F—C$_6$H$_4$** | 4-OCF$_3$—C$_6$H$_4$ | 51.60 | − |
| H | 4-CN—C$_6$H$_4$** | 4-OCF$_3$—C$_6$H$_4$ | 90.00 | + |
| H | 4-CN—C$_6$H$_4$** | 4-OCHF$_2$—C$_6$H$_4$ | 48.40 | − |
| H | 4-CN—C$_6$H$_4$** | 4-OCF$_2$CHF$_2$—C$_6$H$_4$ | 92.80 | − |
| H | 4-CN—C$_6$H$_4$** | 5-chlorothiophen-2-yl | 20.60 | − |
| H | 4-CN—C$_6$H$_4$** | 2,2difluoro-1,3-dioxol-C$_6$H$_3$-5-yl | 88.10 | − |
| H | 4-OCF$_3$—C$_6$H$_4$** | 3,5-diCl—C$_6$H$_3$ | 33.40 | − |
| H | 4-OCF$_3$—C$_6$H$_4$** | 3,4-diF—C$_6$H$_3$ | 100.0 | + |
| H | 4-OCF$_3$—C$_6$H$_4$** | 4-n-propoxy—C$_6$H$_4$ | 10.40 | − |
| H | 4-OCF$_3$—C$_6$H$_4$** | 3,4-diCl—C$_6$H$_3$ | 100.0 | + |
| H | 4-OCF$_3$—C$_6$H$_4$** | 3-F-4-CF$_3$—C$_6$H$_3$ | 44.20 | − |
| H | 4-OCF$_3$—C$_6$H$_4$** | 5-chlorothiophen-2-yl | 26.10 | − |
| H | 4-OCF$_3$—C$_6$H$_4$** | thiophen-2-yl | 0.00 | − |
| H | 4-OCF$_3$—C$_6$H$_4$** | 4-phenoxy-C$_6$H$_4$ | 0.00 | − |
| H | 4-OCF$_3$—C$_6$H$_4$** | pyridine-3-yl | 0.00 | − |
| H | 4-OCF$_3$—C$_6$H$_4$** | 4-OCF$_3$—C$_6$H$_4$ | 100.0 | + |
| H | 4-OCF$_3$—C$_6$H$_4$** | 4-F—C$_6$H$_4$ | 0.00 | + |
| H | 4-OCF$_3$—C$_6$H$_4$** | 4-CN—C$_6$H$_4$ | 88.90 | + |
| H | 4-OCF$_3$—C$_6$H$_4$** | 4-Cl—C$_6$H$_4$ | 100.0 | + |
| H | 4-OCF$_3$—C$_6$H$_4$** | 4-OCHF$_2$—C$_6$H$_4$ | 44.20 | − |
| H | 4-OCF$_3$—C$_6$H$_4$** | 2-F-5-CF$_3$—C$_6$H$_3$ | 29.50 | − |
| H | 4-OCF$_3$—C$_6$H$_4$** | 4-CF$_3$—C$_6$H$_4$ | 55.50 | + |
| H | 4-OCF$_3$—C$_6$H$_4$** | 3-F-5-CF$_3$ | | |
| H | 4-OCF$_3$—C$_6$H$_4$** | pyridine-2-yl | 0.00 | − |
| H | 4-OCF$_3$—C$_6$H$_4$** | 3-Br-pyridine-2-yl | 26.90 | − |
| H | 4-OCF$_3$—C$_6$H$_4$** | 4-(4-F-phenyl)-pyridin-3-yl | 12.80 | − |
| H | 4-OCF$_3$—C$_6$H$_4$** | 4-(thiophen-2-yl)-pyridin-3-yl | 12.80 | − |
| H | 4-OCF$_3$—C$_6$H$_4$** | 4-(4-OCF$_3$—phenyl)-pyridin-3-yl | 82.60 | − |
| H | 4-OCF$_3$—C$_6$H$_4$** | 4-(5-Cl—thiophen-2-yl)-pyridin-3-yl | 88.50 | − |

TABLE VIII-continued

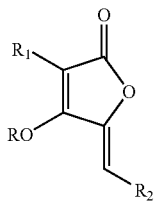

| Test Compound | | | | |
|---|---|---|---|---|
| R | R1 | R2 | Mortality | Toxicity |
| H | 4-OCF$_3$—C$_6$H$_4$** | 4-(4-Cl—phenyl)-pyridin-3-yl | 84.60 | – |
| H | 4-OCF$_3$—C$_6$H$_4$** | 4-(3-Cl—phenyl)-pyridin-3-yl | 66.80 | – |
| H | 4-OCF$_3$—C$_6$H$_4$** | 4-Br-pyridine-3-yl | 12.80 | – |

*E isomer
**Mixture of Z and E isomers

What is claimed is:

1. An ecto- or endoparasiticidal composition which comprises a pharmaceutically acceptable carrier and an effective amount of a compound of formula I

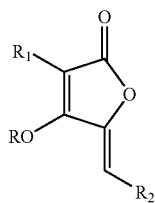

(I)

wherein
R is H, COR$_4$ or a C$_1$-C$_6$alkyl, C$_3$-C$_6$cycloalkyl, C$_2$-C$_6$alkenyl, C$_2$-C$_6$alkynyl, benzyl, aryl or heteroaryl group each optionally substituted;

R$_1$ is phenyl optionally substituted with one, two or three halogen, CN, OR$_3$, COR$_4$, SO$_2$R$_5$, NR$_6$SO$_2$R$_7$, NR$_8$COR$_9$, NR$_{10}$R$_{11}$, C$_1$-C$_6$haloalkyl or a C$_1$-C$_6$alkyl, C$_3$-C$_6$cycloalkyl, C$_2$-C$_6$alkenyl or C$_2$-C$_6$alkynyl group each optionally substituted, biphenyl optionally substituted with one, two or three halogen, CN, OR$_3$, COR$_4$, SO$_2$R$_5$, NR$_6$SO$_2$R$_7$, NR$_8$COR$_9$, NR$_{10}$R$_{11}$, C$_1$-C$_6$haloalkyl or a C$_1$-C$_6$alkyl, C$_3$-C$_6$cycloalkyl, C$_2$-C$_6$alkenyl or C$_2$-C$_6$alkynyl group each optionally substituted, or naphthyl optionally substituted with one, two or three halogen, CN, OR$_3$, COR$_4$, SO$_2$R$_5$, NR$_6$SO$_2$R$_7$, NR$_8$COR$_9$, NR$_{10}$R$_{11}$, C$_1$-C$_6$haloalkyl or a C$_1$-C$_6$alkyl, C$_3$-C$_6$cycloalkyl, C$_2$-C$_6$alkenyl or C$_2$-C$_6$alkynyl group each optionally substituted, or heteroaryl optionally substituted with one, two or three halogen, CN, OR$_3$, COR$_4$, SO$_2$R$_5$, NR$_6$SO$_2$R$_7$, NR$_8$COR$_9$, NR$_{10}$OR$_{11}$, C$_1$-C$_6$haloalkyl or a C$_1$-C$_6$alkyl, C$_3$-C$_6$cycloalkyl, C$_2$-C$_6$alkenyl or C$_2$-C$_6$alkynyl group each optionally substituted;

R$_2$ is a phenyl or biphenyl group substituted with one or two halogen, CN or CF$_3$ groups;

R$_3$, R$_4$, R$_9$, R$_{12}$, R$_{13}$ and R$_{18}$ are each independently H, C$_1$-C$_8$, haloalkyl, or a C$_1$-C$_6$alkyl, C$_3$-C$_6$cycloalkyl, C$_2$-C$_6$alkenyl, C$_2$-C$_6$alkynyl, benzyl, aryl or heteroaryl group each optionally substituted;

R$_5$, R$_7$, R$_{14}$ and R$_{16}$ are each independently a C$_1$-C$_6$alkyl, C$_3$-C$_6$cycloalkyl, C$_2$-C$_6$alkenyl, C$_2$-C$_6$alkyl, benzyl, aryl or heteroaryl group each optionally substituted;

R$_6$, R$_8$, R$_{15}$ and R$_{17}$ are each independently H or an optionally substituted C$_1$-C$_6$alkyl group; and R$_{10}$, R$_{11}$, R$_{19}$ and R$_{20}$ are each independently H, C$_1$-C$_6$, haloalkyl, or a C$_1$-C$_6$alkyl, C$_3$-C$_6$cycloalkyl, C$_2$-C$_6$alkenyl, C$_2$-C$_6$alkynyl, benzyl, aryl or heteroaryl group each optionally substituted or R$_{10}$ and R$_{11}$ or R$_{19}$ and R$_{20}$ may be taken together with the atom to which they are attached to form an optionally substituted 5- to 7-membered ring optionally containing one or two additional heteroatoms selected from N, O or S; or a stereoisomer thereof, a tautomer thereof or a pharmaceutically acceptable salt thereof.

2. An ecto- or endoparasiticidal composition which comprises a pharmaceutically acceptable carrier and an effective amount of a compound of formula I

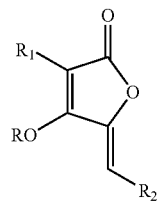

(I)

wherein
R is H, COR$_4$ or a C$_1$-C$_6$alkyl, C$_3$-C$_6$cycloalkyl, C$_2$-C$_6$alkenyl, C$_2$-C$_6$alkynyl, benzyl, aryl or heteroaryl group each optionally substituted;

R$_1$ is a phenyl or biphenyl group substituted with one or two halogen, CN or CF$_3$ groups;

R$_2$ is an optionally substituted phenyl or biphenyl group;

R$_3$, R$_4$, R$_9$, R$_{12}$, R$_{13}$ and R$_{18}$ are each independently H, C$_1$-C$_6$, haloalkyl, or a C$_1$-C$_6$alkyl, C$_3$-C$_6$cycloalkyl, C$_2$-C$_6$alkenyl, C$_2$-C$_6$alkynyl, benzyl, aryl or heteroaryl group each optionally substituted;

$R_5$, $R_7$, $R_{14}$ and $R_{16}$ are each independently a $C_1$-$C_6$alkyl, $C_3$-$C_6$cycloalkyl, $C_2$-$C_6$alkenyl, $C_2$-$C_6$alkyl, benzyl, aryl or heteroaryl group each optionally substituted;

$R_6$, $R_8$, $R_{15}$ and $R_{17}$ are each independently H or an optionally substituted $C_1$-$C_6$alkyl group; and $R_{10}$, $R_{11}$, $R_{19}$ and $R_{20}$ are each independently H, $C_1$-$C_6$, haloalkyl, or a $C_1$-$C_6$alkyl, $C_6$cycloalkyl, $C_2$-$C_6$alkenyl, $C_2$-$C_6$alkenyl, benzyl, aryl or heteroaryl group each optionally substituted or $R_{10}$ and $R_{11}$ or $R_{19}$ and $R_{20}$ may be taken together with the atom to which they are attached to form an optionally substituted 5- to 7-membered ring optionally containing one or two additional heteroatoms selected from N, O or S; or a stereolsomer thereof, a tautomer thereof or a pharmaceutically acceptable salt thereof.

3. A method for the treatment of bacterial infection or disease in a patient in need thereof which comprises providing to said patient a pharmacologically effective amount of a compound of formula I

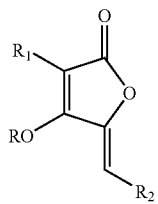

(I)

wherein

R is H;

$R_1$ is phenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, biphenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, naphthyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, or heteroaryl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_2$ is phenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl or heteroaryl group each optionally substituted with the proviso that only one of $R_1$ or $R_2$ may be an optionally substituted phenyl group;

biphenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

naphthyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

heteroaryl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl, phenyl or heteroaryl group each optionally substituted; or $C_3$-$C_6$cycloalkyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_3$, $R_4$, $R_9$, $R_{12}$, $R_{13}$ and $R_{18}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_5$, $R_7$, $R_{14}$ and $R_{16}$ are each independently a $C_1$-$C_6$alkyl, $C_3$-$C_6$cycloalkyl, $C_2$-$C_6$alkenyl, $C_2$-$C_6$alkyl, benzyl, aryl or heteroaryl group each optionally substituted;

$R_6$, $R_8$, $R_{15}$ and $R_{17}$ are each independently H or an optionally substituted $C_1$-$C_6$alkyl group; and $R_{10}$, $R_{11}$, $R_{19}$ and $R_{20}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted or $R_{10}$ and $R_{11}$ or $R_{19}$ and $R_{20}$ may be taken together with the atom to which they are attached to form an optionally substituted 5- to 7-membered ring optionally containing one or two additional heteroatoms selected from N, O or S; or the stereoisomers thereof, the tautomers thereof or the pharmaceutically acceptable salts thereof.

4. The method according to claim 3 wherein the bacterial infection is caused by one or more of the bacteria selected from the group consisting of the genera *Staphylococcus; Streptococcus; Mycobacterium; Escherichia; Bacillus; Clostridium; Pasteurella; Haemophilus; Bordetella*; and *Pseudomonas*.

5. The method according to claim 4 having the formula I compound wherein $R_1$ is phenyl substituted with one or two halogen or $CF_3$ groups and $R_2$ is an optionally substituted biphenyl group.

6. The method according to claim 4 having the formula I compound wherein $R_1$ is an optionally substituted biphenyl group and $R_2$ is phenyl substituted with one or two halogen or $CF_3$ groups.

7. A method for treating ecto- or endoparasitic infection in a homeothermic animal which comprises administering to said animal a prophylactically, effective amount of a compound of formula I

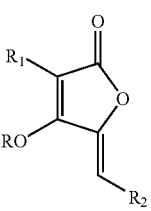

(I)

wherein

R is H, $COR_4$ or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_1$ is phenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, biphenyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, naphthyl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted, or heteroaryl optionally substituted with one, two or three halogen, CN, $OR_3$, $COR_4$, $SO_2R_5$, $NR_6SO_2R_7$, $NR_8COR_9$, $NR_{10}R_{11}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_2$ is phenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl or heteroaryl group each optionally substituted;

biphenyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

naphthyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

heteroaryl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl, $C_2$-$C_6$alkynyl, phenyl or heteroaryl group each optionally substituted; or $C_3$-$C_6$cycloalkyl optionally substituted with one, two or three halogen, CN, $OR_{12}$, $COR_{13}$, $SO_2R_{14}$, $NR_{15}SO_2R_{16}$, $NR_{17}COR_{18}$, $NR_{19}R_{20}$, $C_1$-$C_6$haloalkyl or a $C_1$-$C_6$alkyl, $C_3$-$C_6$cycloalkyl, $C_2$-$C_6$alkenyl or $C_2$-$C_6$alkynyl group each optionally substituted;

$R_3$, $R_4$, $R_9$, $R_{12}$, $R_{13}$ and $R_{18}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_5$, $R_7$, $R_{14}$ and $R_{16}$ are each independently a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted;

$R_6$, $R_8$, $R_{15}$ and $R_{17}$ are each independently H or an optionally substituted $C_1$-$C_6$alkyl group; and $R_{10}$, $R_{11}$, $R_{19}$ and $R_{20}$ are each independently H, $C_1$-$C_6$, haloalkyl, or a $C_1$-$C_6$alkyl, $C_3$-$C_6$cycloalkyl, $C_2$-$C_6$alkenyl, $C_2$-$C_6$alkynyl, benzyl, aryl or heteroaryl group each optionally substituted or $R_{10}$ and $R_{11}$ or $R_{19}$ and $R_{20}$ may be taken together with the atom to which they are attached to form an optionally substituted 5- to 7-membered ring optionally containing one or two additional heteroatoms selected from N, O or S; or a stereoisomer thereof, a tautomer thereof or a pharmaceutically acceptable salt thereof.

8. The method according to claim 7 having a formula I compound wherein $R_1$ is phenyl substituted with one or two halogen, CN or $C_1$-$C_6$haloalkyl groups.

9. The method according to claim 7 having a formula I compound wherein $R_1$ is an optionally substituted biphenyl group.

10. The method according to claim 7 having a formula I compound wherein $R_2$ is phenyl substituted with one or two halogen, CN or $C_1$-$C_6$haloalkyl groups.

11. The method according to claim 8 having a formula I compound wherein $R_2$ is phenyl substituted with one or two halogen, CN or $C_1$-$C_6$haloalkyl groups.

12. The method according to claim 8 having a formula I compound wherein $R_2$ is an optionally substituted biphenyl group.

13. The method according to claim 7 wherein the ectoparasite is selected from the group consisting of: *Diptera; Muscidae*; and Siphonáptera.

14. The method according to claim 7 wherein the endoparasite is Trematoda or Nematoda.

15. The method according to claim 7 wherein the homeothermic animal is selected from the group consisting of: cattle; sheep; horse; goat; pig; camel; water buffalo; donkey; rabbit; fallow deer; reindeer; mink; chinchilla; raccoon; chicken; geese; turkey; duck; dog; cat; and human.

16. The method according to claim 13 wherein the ectoparasite is selected from the group consisting of: fleas; lice; blow flies; face flies and horn flies.

17. The method according to claim 14 wherein the endoparasite is selected from the group consisting of: *Faciola hepatica; Trichostrongylus colubriformis*; and *Haemonchus contortus*.

* * * * *